United States Patent [19]

Mikoshiba et al.

[11] Patent Number: 5,310,634

[45] Date of Patent: May 10, 1994

[54] COLOR DEVELOPING AGENT AND IMAGE FORMING PROCESS

[75] Inventors: Hisashi Mikoshiba; Mitsugu Tanaka; Kei Sakanoue, all of Kanagawa, Japan

[73] Assignee: Fuji Photo Film Co., Ltd., Kanagawa, Japan

[21] Appl. No.: 790,094

[22] Filed: Oct. 30, 1991

Related U.S. Application Data

[63] Continuation of Ser. No. 509,530, Apr. 16, 1990, abandoned.

[30] Foreign Application Priority Data

Apr. 17, 1989 [JP] Japan .................... 1-96619

[51] Int. Cl.⁵ .............. G03C 5/30; G03C 7/32; G03C 1/42; G03C 1/494
[52] U.S. Cl. .................. 430/467; 430/442; 430/443; 430/484; 430/543; 430/566; 430/617; 430/351; 430/959; 560/15; 560/16; 560/24; 560/29; 564/49; 564/50
[58] Field of Search ............ 430/442, 443, 959, 484, 430/467, 376, 566; 560/15, 16, 24, 29; 564/49, 50

[56] References Cited

U.S. PATENT DOCUMENTS

| | | | |
|---|---|---|---|
| 3,723,117 | 3/1973 | Willems | 430/484 |
| 3,763,141 | 10/1973 | Weaver et al. | 560/24 |
| 4,113,491 | 9/1978 | Deguchi et al. | |
| 4,246,196 | 1/1981 | Arndt et al. | 564/50 |
| 4,770,981 | 9/1988 | Komamura et al. | 430/351 |
| 5,063,143 | 11/1991 | Hirose et al. | 430/467 |

FOREIGN PATENT DOCUMENTS

| | | | |
|---|---|---|---|
| 0255734 | 2/1988 | European Pat. Off. | |
| 2604804 | 8/1976 | Fed. Rep. of Germany | 430/442 |
| 56-016133 | 2/1981 | Japan | 430/566 |

OTHER PUBLICATIONS

Chemical Abstracts, vol. 95, No. 1, Jul. 6, 1981, "Heat-Resistance Polymers", p. 40, col. 1, Abstract No. 8258x.

Photographic Science and Engineering, vol. 8, No. 3 (1964).

Primary Examiner—Janis Dote
Attorney, Agent, or Firm—Sughrue, Mion, Zinn, Macpeak & Seas

[57] ABSTRACT

A p-phenylenediamine series color developing agent or a precursor thereof having a substituent A at the ortho-position; Substituent A:

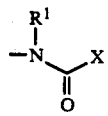

wherein $R^1$ represents a hydrogen atom or an alkyl group and X represents $-O-R^7$ or

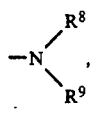

wherein $R^7$ represents an alkyl group, an aryl group, or a heterocyclic ring and $R^8$ and and $R^9$, which may be the same or different, each represents a hydrogen atom, an alkyl group, an aryl group, or a heterocyclic ring, $R^8$ and $R^9$ may combine with each other to form a heterocyclic ring, and a process for forming an image which comprises imagewise exposing a silver halide color photographic material and thereafter color developing the color photographic material in the presence of a p-phenylenediamine series color developing agent or a precursor thereof having the aforesaid substituent A.

18 Claims, No Drawings

COLOR DEVELOPING AGENT AND IMAGE FORMING PROCESS

This is a continuation of application Ser.No. 07/509,530 filed Apr. 16, 1990 now abandoned.

FIELD OF THE INVENTION

The present invention relates to a color developing agent for silver halide color photographic materials or a precursor for the color developing agent and to an image forming process using it. More particularly, the present invention relates to a p-phenylenediamine type color developing agent being used for forming color images together with couplers or a precursor for the color developing agent and to an image forming process using it.

BACKGROUND OF THE INVENTION

In general, color photographic images are formed by processing a silver halide color photographic material as follows. First, the color photographic material is imagewise exposed and developed by a developing composition containing a color developing agent. In this case, the silver halide at the exposed portions is reduced to silver and at the same time, the color developing agent is oxidized. The oxidized color developing agent thus formed causes coupling with couplers contained in the color photographic material to imagewise form dyes corresponding to developed silver. It is known that a p-phenylenediamine derivative is used as the color developing agent for obtaining color images by utilizing the oxidative power of the exposed silver halide.

A color developing composition being used for performing the aforesaid color development generally contains 1) a color developing agent, 2) a preservative for preventing the color developing agent from being deteriorated by air oxidation, such as sodium sulfite, hydroxylamine, etc., 3) a buffer for stabilizing the developing composition at high pH for obtaining a high developing activity, 4) an antifoggant, 5) benzyl alcohol for accelerating the coupling reaction, etc. Also, as the case may be, the color developing composition contains a polyethylene glycol, a surface active agent, an auxiliary developing agent, etc.

A color developing agent excluding benzyl alcohol which has hitherto been used for accelerating development has recently been particularly desired from the viewpoint of a pollution countermeasure. However, when a color photographic material is deeloped by a color developer containing a known color developing agent without using benzyl alcohol, the density of images formed is extremely reduced. Accordingly, it has been keenly desired to find a color developing agent which can give dyes having sufficiently high density regardless of the presence or absence of benzyl alcohol.

Also, in the color development step, all the silver halide grains having latent images do not always relate to the formation of dyes at color development. So-called "dead grains" are wasted in a color photographic development. Accordingly, a new color developing agent capable of forming a dye at a larger ratio to the amount of exposed silver halide than that attained by a conventional color developing agent has been required. If silver halide grains are effectively converted to silver and then a dye is effectively formed, the amount of silver being used may be less and the thickness of the photographic emulsion layers of a color photographic light-sensitive material can be reduced, which gives various advantages, that is, a quick development process can be applied and color images having high resolving power are obtained.

Also, for sufficiently increasing the density of dyes formed by development, it is most advantageous to increase the extinction coefficient of the dyes formed. If a new color developing agent giving a dye having a far larger extinction coefficient than that of a dye formed from a conventional color developing agent is obtained, it becomes possible to reduce the amount of couplers in a color photographic material and to reduce the thickness of the photographic emulsion layers of a color photographic material.

Also, in regard to the color reproduction of color images formed by development, the color images of dyes formed using a conventional color developing agent are insufficient in color reproduction since the absorption of the dye is boad and a side absorption exists in the color images. In particular, the absorption of a cyan dye formed from a cyan formed by coupler (cyan coupler) and a color developing agent is broad and hence the discovery of a new color developing agent giving a cyan dye having a sharp absorption has been desired.

On the other hand, a color developer is unstable and the composition of a color developer is liable to change during the storage thereof, whereby the management of a color developer is difficult. Accordingly, it has recently been proposed to incorporate a color developing agent in a silver halide color photographic material. By incorporating a color developing agent in a color photographic material, the composition of a color developer is simplified and the management of the color developer becomes easy. Also, in this case, the color photographic material can be developed by an alkaline bath only, which is very useful for the simplification and quickening of processing.

However, when a p-phenylenediamine series developing agent is incorporated in a color photographic material, there occur problems that the color photographic material is liable to cause desensitization, fog, or stains during the storage thereof. Thus, a system of incorporating a precursor for the color developing agent in a color developing material for increasing the stability of the color developing agent in the color photographic material during the storage thereof has been proposed.

For example, Schiff base type precursors for color developing agents are disclosed in U.S. Pat. No. 3,342,599 and JP-A-56-106241, JP-A-56-107236 and JP-A-56-123534 (the term "JP-A" as used herein refers to a "published unexamined Japanese patent application"). Also, sulfonylethylurethane type precursors are disclosed in JP-B-58-14671 (the term "JP-B" as used herein refers to an "examined Japanese patent publication"), cyanoethylurethane type precursors are disclosed in JP-B-58-14672, arylurethane type precursors are disclosed in JP-A-58-95344, JP-A-61-113059, and JP-A-61-114238, and arylurea type precursors are disclosed in JP-A-59-53931.

By the aforesaid techniques, it becomes possible to incorporate a p-phenylenediamine series color developing agent in a color photographic material but there remains a large problem that has not yet been solved.

That is, the color developing agent precursors used in these conventional techniques are all the precursors for conventionally known color developing agents and these precursors have the problems of the conventionally known color developing agents as they are. For example, there are problems that when the color photographic material contains such a precursor with an activator solution witnout containing benzyl alcohol, the density of color images formed is greatly reduced, the ratio of dyes formed to the exposed silver halide is yet low, the extinction coefficient of dyes formed is yet low, and the absorption of a dye formed is broad. Thus, it has been keenly desired to discover precursors for color developing agents having no such problems of the conventionally known color developing agents.

Also, a system of incorporating a color developing agent in a light-sensitive material and obtaining color images through a heat development step is known in JP-A-59-12431. JP-A-59-116642, JP-A-59-116643 and JP-A-59-116740.

The heat developable light-sensitive material can be composed of 1) a color developing agent, 2) a light-sensitive silver halide, and 3) a dye providing material but, if desired, an organic silver salt can be used. In this case, a dye is formed or released from the dye providing material as a function of the reduction of the light-sensitive silver halide and/or the organic silver salt.

In the aforesaid system, a system shown below has been actively investigated recently.

That is, a heat developable light-sensitive material in the system is composed of 1) an organic silver oxidizing agent stable to light, 2) a color developing agent, 3) a silver halide which becomes a catalyst for an oxidation reduction reaction of the organic silver oxidizing agent and the color developing agent at heat development when the silver halide is light exposed, 4) a material providing a dye by causing a reaction with the oxidation product of the color developing agent, 5) a binder, and 6) a support.

In general, the aforesaid heat developable light-sensitive material forms color images by the following manner. When the exposed heat developable light-sensitive material is heat developed, an oxidation reduction reaction occurs between the organic silver salt oxidizing agent and the color developing agent with the exposed light-sensitive silver halide as a catalyst to form silver images at the exposed portions. In this case, the color developing agent is simultaneously converted into the oxidation product thereof and the oxidation product causes a coupling reaction with the dye providing material to form color images as a function of the reduction of the organic silver salt oxidizing agent.

In the color developing agent which is used for the aforesaid heat developable light-sensitive material, there also exists the same problems as in the case of the color developing agent which is used for the aforesaid color developing composition. That is, a color developing agent giving a larger ratio of the dye formed to the organic silver salt oxidizing agent or to the exposed silver halide than that of a conventionally used color developing agent has been required.

Furthermore, for sufficiently increasing the density of color images formed, the discovery of a color developing agent giving a dye having a far larger extinction coefficient than dyes formed by using conventional color developing agents has been strongly desired.

Also, in regard to the color reproduction of color images formed by development, the discovery of a color developing agent giving a dye having a sharper absorption has been strongly desired.

Now, color developing agents capable of being developed by a developer containing no benzyl alcohol from the viewpoint of avoiding the occurrence of pollution are disclosed in JP-A-52-134432, JP-A-52-76032, JP-A-51-95849, and JP-A-50-131526. However, it cannot be said that a sufficient dye density is obtained by using these color developing agents. Also, the ratio of the dye density formed at color developing latent images to the density of developed silver formed simultaneously is yet low. One of the reasons is that the extinction coefficient of the dye formed by coupling is low. Furthermore, these conventional color developing agents have a disadvantage that the absorption of dyes formed is broad.

Moreover, since conventionally known precursors for color developing agents which can be used in a color photographic light-sensitive material are precursors for conventionally known color developing agents only, these precursors have the aforesaid problems of the conventionally known color developing agents as they are.

Furthermore, the similar problems exist in the case of using these color developing agents for a heat developable light-sensitive material. For example, heat developable light-sensitive materials using p-phenylenediamine derivative series color developing agents are disclosed in JP-A-59-57237, JP-A-56-146133, JP-A-59-116740, and JP-A-63-301037 but in the case of using these color developing agents or the precursors thereof, a sufficient dye density is not obtained. Also, in these cases, there are various problems that the ratio of a dye formed by color development to the organic silver salt oxidizing agent or the exposed silver halide is yet low, the extinction coefficient of the dye formed is small, an the absorption of the dye formed is broad.

SUMMARY OF THE INVENTION

An object of the present invention is to provide a novel and excellent color developing agent.

Another object of the present invention is to provide a novel color developing agent capable of giving a sufficiently high density without need of using benzyl alcohol in the case of using the color developing agent or the precursor thereof in a color developer or in the case of incorporating the color developing agent or the precursor in a color photographic light-sensitive material and subjecting the light-sensitive material to an activate processing (e.g., a processing using only an alkaline bath).

Yet another object of the present invention is to provide a novel color developing agent and the precursor for the developing agent capable of giving a much larger ratio of a dye density obtained by color developing latent images, in the case of using the color developing agent or the precursor in the color developer or in the case of subjecting the color photographic light-sensitive material containing the color developing agent or the precursor to activate processing, to the density of developed silver simultaneously formed than the value obtained in the case of using a conventional color developing agent.

A further object of the present invention is to provide a novel color developing agent and the precursor thereof giving a very large ratio of a dye formed by color development to an organic silver salt oxidizing agent or the exposed silver halide in the case of using the color developing agent or the precursor in a heat developable light-sensitive material than the value obtained in the case of using a conventionally known color developing agent.

Other object of the present invention is to provide a novel color developing agent and the precursor thereof giving a dye having a large extinction coefficient by coupling with a coupler.

A still other object of the present invention is to provide a novel color developing agent and the precursor thereof giving a dye having a sharp absorption by coupling with a coupler.

A still further object of the present invention is to provide a silver halide color photographic material having greatly improved photographic characteristics (e.g., Dmax) and an image forming process using the color photographic material.

Other objects of the present invention will become apparent from the following descriptions.

It has been discovered that the aforesaid objects can be attained by the present invention described below.

That is, according to an embodiment of the present invention there is provided a p-phenylenediamine series color developing agent or a precursor thereof having a substituent A shown below at the ortho-position:

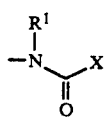

wherein $R^1$ represents a hydrogen atom or an alkyl group and X represents $-O-R^7$ or

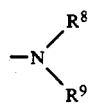

(wherein $R^7$ represents an alkyl group, an aryl group, or a heterocyclic ring and $R^8$ and $R^9$, which may be the same or different, each represents a hydrogen atom, an alkyl group, an aryl group, or a heterocyclic ring, $R^8$ and $R^9$ may combine with each other to form a heterocyclic ring).

According to another embodiment of the present invention, there is provided a process for forming an image, which comprises imagewise exposing a silver halide color photographic material and thereafter color developing the color photographic material in the presence of a p-phenylenediamine series color developing agent or a precursor thereof having the aforesaid substituent A at the ortho-position.

DETAILED DESCRIPTION OF THE INVENTION

Then, the present invention is described in detail.

The p-phenylenediamine derivative (p-phenylenediamine series color developing agent) having the aforesaid substituent A at the ortho-position thereof is preferably a compound represented by formula (I):

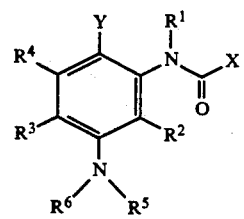

wherein $R^1$ represents a hydrogen atom or an alkyl group (preferably having from 1 to 12 carbon atoms); X represents $-O-R^7$ or

(wherein $R^7$ represents an alkyl group, an aryl group, or a heterocyclic ring and $R^8$ and $R^9$, which may be the same or different, each represents a hydrogen atom, an alkyl group, an aryl group, or a heterocyclic ring, $R^8$ and $R^9$ may combine with each other to form a heterocyclic ring); $R^2$, $R^3$, and $R^4$, which may be the same or different, each represents a hydrogen atom, an alkyl group, an amino group, a hydroxy group, an alkoxy group, an acylamino group, a sulfonamide group, an alkoxycarbonylamino group, an aminocarbonylamino group, a sulfonyl group, a carbamoyl group, a sulfamoyl group, a cyano group, a halogen atom, an alkoxycarbonyl group, an acyl group, an acyloxy group, a sulfo group, or a carboxy group; $R^3$ and $R^4$ may combine with each other to form a ring structure; $R^1$ or $R^2$ and X may combine with each other to form a heterocyclic ring; $R^5$ and $R^6$ each represents a hydrogen atom or an alkyl group, $R^5$ and $R^6$, $R^3$ and $R^6$, and/or $R^2$ and $R^5$ may combine with each other to form a ring structure, and $R^2$ and X may combine with each other to form a heterocyclic ring; and Y represents

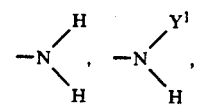

or $-N=Y^2$ [wherein $Y^1$ represents $-SO_3H$, $-SO_3Na$, $-SO_2R^{11}$,

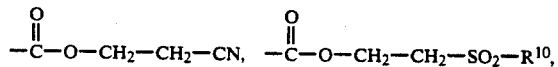

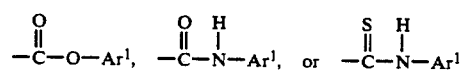

(wherein $R^{10}$ and $R^{11}$ each represents an alkyl group (preferably having from 1 to 12 carbon atoms) or an aryl group (preferably having from 6 to 14 carbon atoms) which may be substituted, and $Ar^1$ represents an aryl group which may be substituted) and $Y^2$ represents

(wherein Ar² represents an aryl group (preferably having from 6 to 14 carbon atoms) which may be substituted)].

Then, the compound represented by formula (I) is explained in detail.

In formula (I), R¹ represents a hydrogen atom or an alkyl group and represents preferably a hydrogen atom.

In —O—R⁷ represented by X in formula (I), R⁷ is preferably an alkyl group having from 1 to 4 carbon atoms and the alkyl group may be unsubstituted or substituted. As substituents for the alkyl group, there are preferably a hydroxy group, an amino group, an alkoxy group, an aminocarbonyloxy group, an acylamino group, a sulfonylamino group, or a halogen atom. The alkyl group represented by R⁷ is preferably substituted.

In

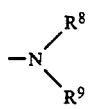

represented by X, R⁸ and R⁹ each is preferably an alkyl group having from 1 to 4 carbon atoms and in the alkyl group represented by R⁸ or R⁹, the preferred alkyl group is the same as the alkyl group for R⁷. Also, R⁸ and R⁹ may combine with each other to form a heterocyclic ring.

As X, —O—R⁷ is better than

In formula (I), R², R³ and R⁴ each is preferably a hydrogen atom or an alkyl group having 1 or 2 carbon atoms and is most prefrably a hydrogen atom.

R⁵ and R⁶ each represents an alkyl group having, preferably, from 1 to 6 carbon atoms. The alkyl group may be unsubstituted or substituted and as a substituent for the alkyl group, there are preferably a hydroxy group, an amino group, an alkoxy group, an aminocarbonyloxy group, an alkoxycarbonyl group, a sulfonylamino group, a halogen atom, a sulfo group, a carboxy group, an acyloxy group, an alkoxycarbonyloxy group, a cyano group, an acylamino group, and a sulfonyl group.

Y represents

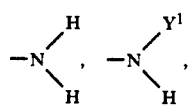

or —N=Y² [wherein Y¹ represents —SO₃H, —SO₃Na, —SO₂R¹¹,

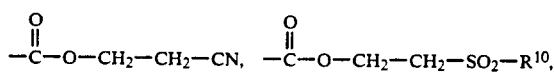

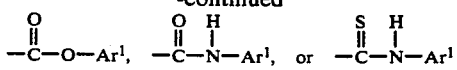

(wherein R¹⁰ and R¹¹ each represents an alkyl group having preferably from 1 to 10 carbon atoms or an aryl group having from 6 to 10 carbon atoms and Ar¹ represents an aryl group which may be substituted. As substituents for the aryl group, there are preferably a hydroxy group, an amino group, an alkoxy group, an aminocarbonylamino group, an alkyl group, an acylamino group, a sulfonamide group, an alkoxycarbonylamino group, a sulfonyl group, a carbamoyl group, a sulfamoyl group, a cyano group, a halogen atom, an alkoxycarbonyl group, an acyl group, an acyloxy group, a sulfo group, and a carboxy group. These substituents may be further substituted. Y² represents $$=\overset{H}{\underset{|}{C}}-Ar^2$$

(wherein Ar² has the same meaning as Ar¹ described above)].

When the color developing agent of the present invention is used in a color developer, Y has preferably a structure represented by

Also, when the color developing agent is used in a color photographic material being subjected to an activator processing or in a heat developable light-sensitive material, Y has preferably a structure represented by

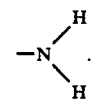

The p-phenylenediamine derivative of the present invention is used for color development of a color photographic material.

When the novel color developing agent of the present invention is used in a color developer, the developing agent is preferably used as a free base or, as a case may be, a salt of an organic acid such as oxalic acid, methanesulfonic acid, benzenesulfonic acid, p-toluenesulfonic acid, and 1,5-naphthalenedisulfonic acid or an inorganic acid such as hydrochloric acid, sulfuric acid, and perchloric acid.

Then, specific examples of the color developing agent of the present invention are illustrated below but the present invention is not limited to these compounds. The following compounds are shown as the form of free bases.

When the novel color developing agent of the present invention or the precursor thereof for the developing agent is used in a color photographic light-sensitive material, it is used as a free developing agent, a salt of an organic or inorganic acid, or a precursor.

Specific compounds are as follows.

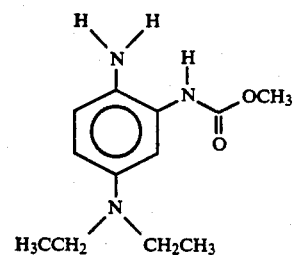 (1)
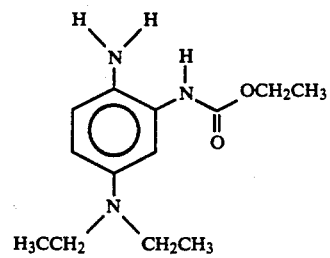 (2)
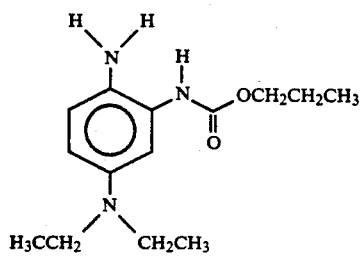 (3)
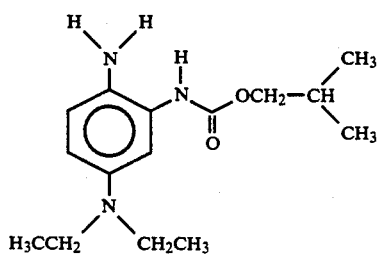 (4)
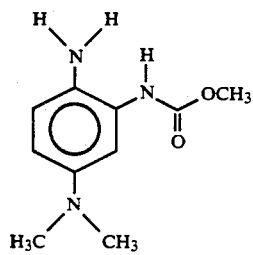 (5)
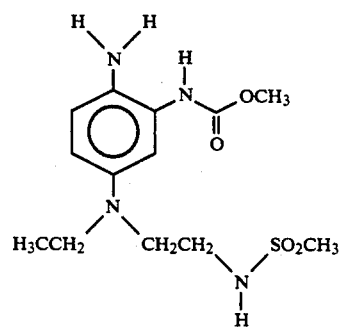 (6)
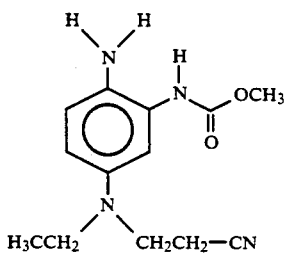 (7)
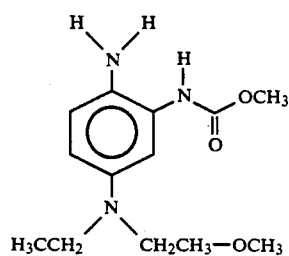 (8)
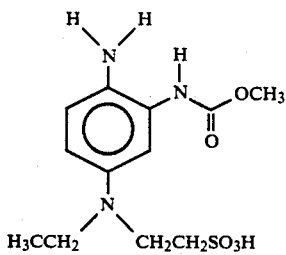 (9)
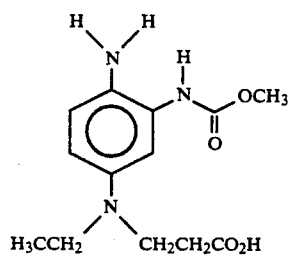 (10)
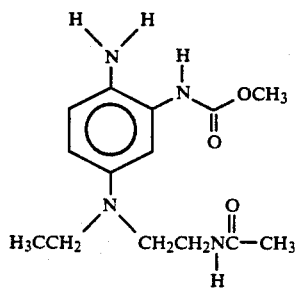 (11)
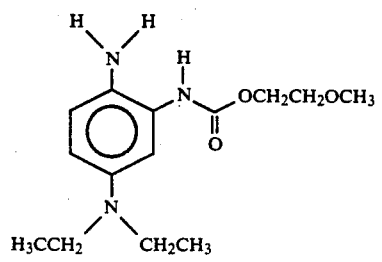 (12)

-continued
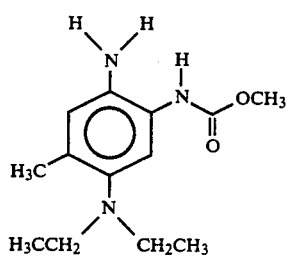 (13)
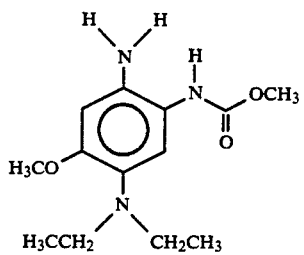 (14)
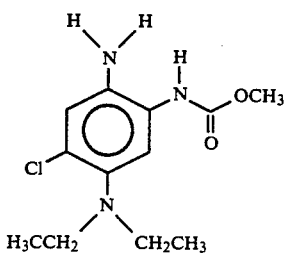 (15)
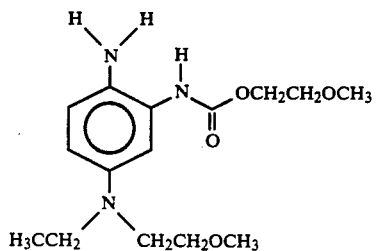 (16)
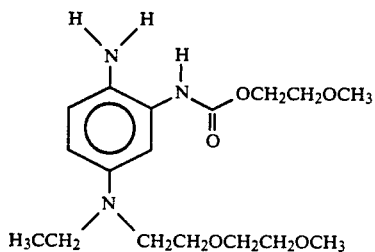 (17)
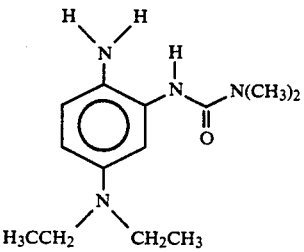 (18)
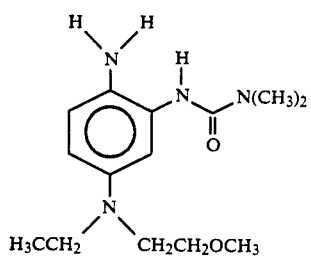 (19)
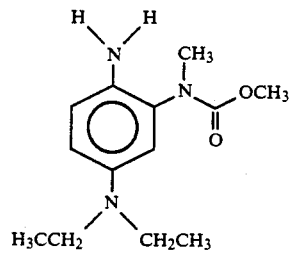 (20)
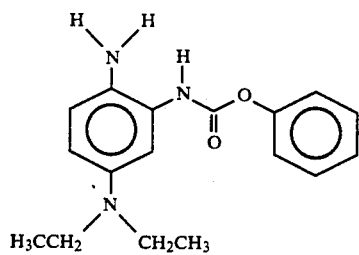 (21)
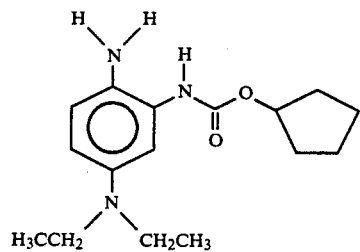 (22)
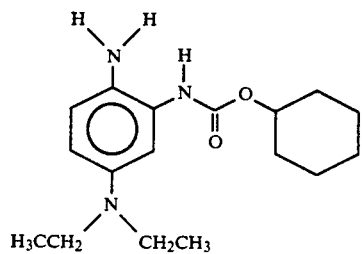 (23)
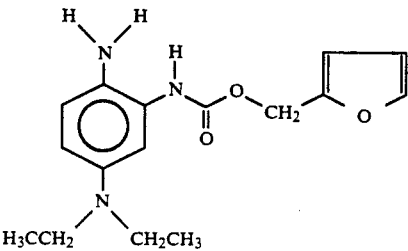 (24)

-continued
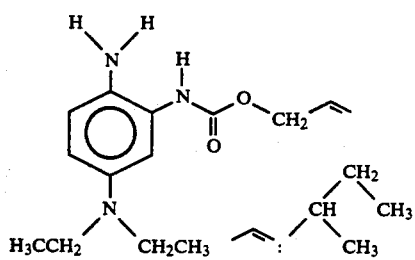 (25)
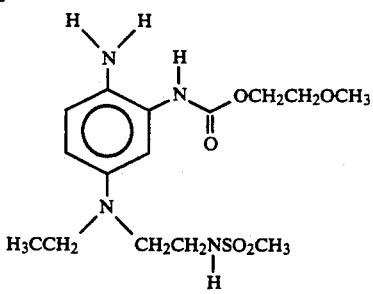 (26)
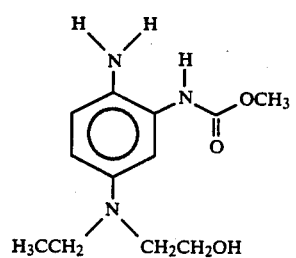 (27)
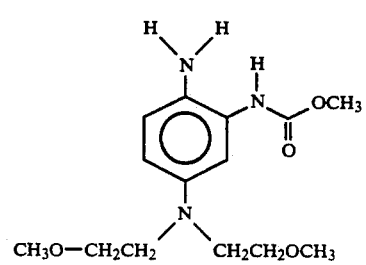 (28)
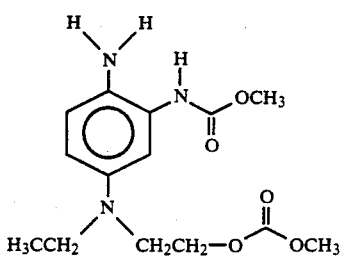 (29)
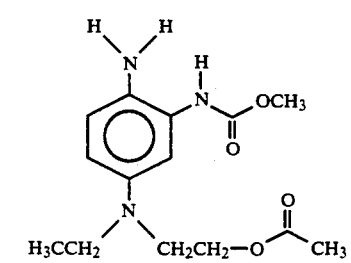 (30)
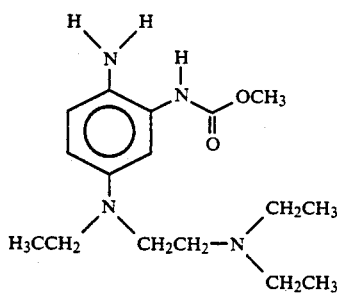 (31)
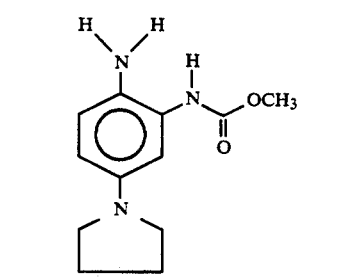 (32)
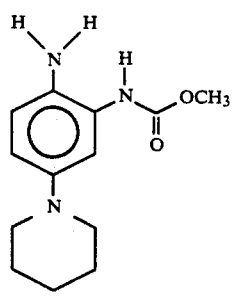 (33)
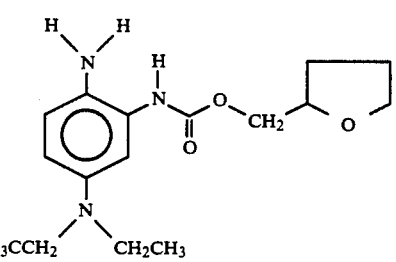 (34)
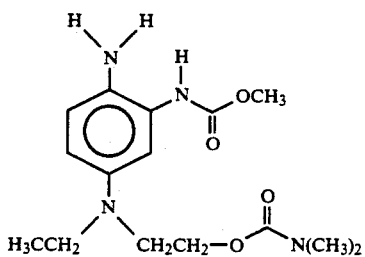 (35)
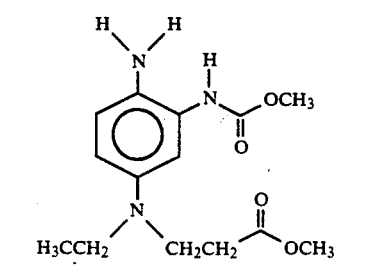 (36)

-continued
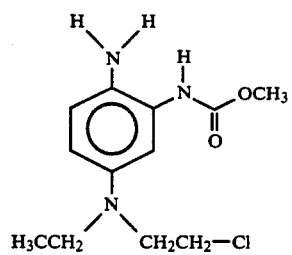 (37)
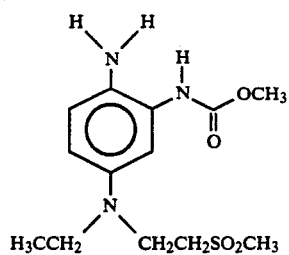 (38)
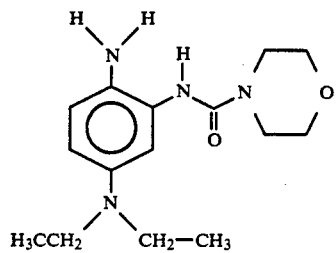 (39)
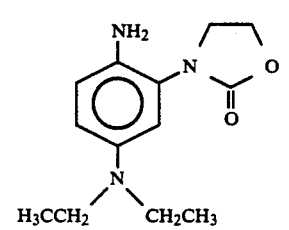 (40)
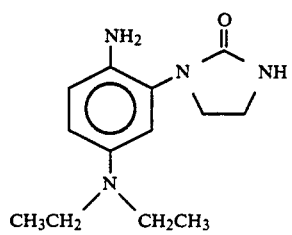 (41)
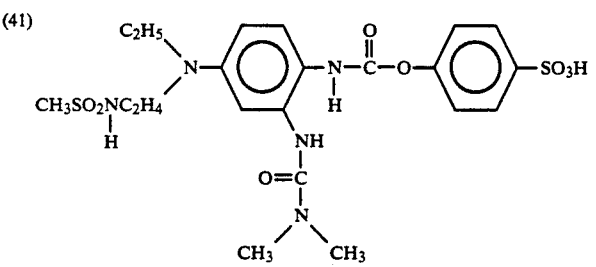 (42)
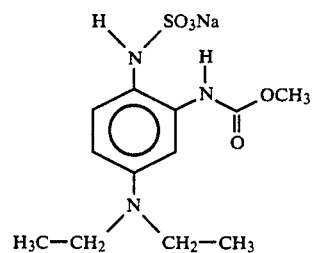 (43)
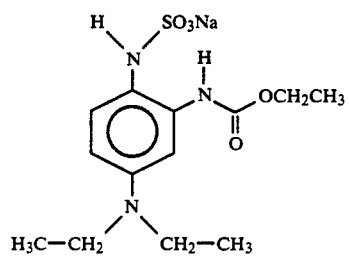 (44)
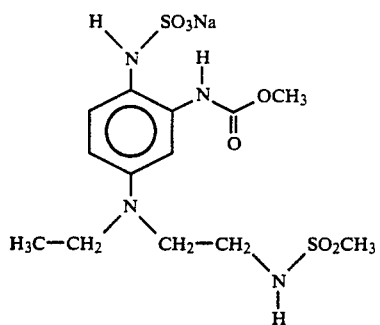 (45)
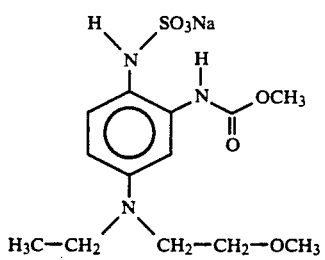 (46)
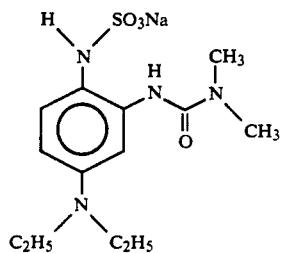 (47)
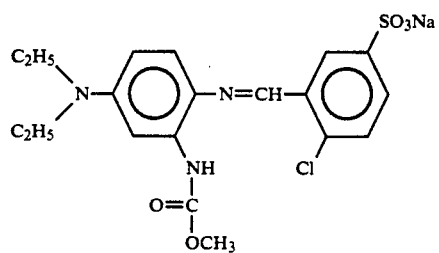 (48)

-continued
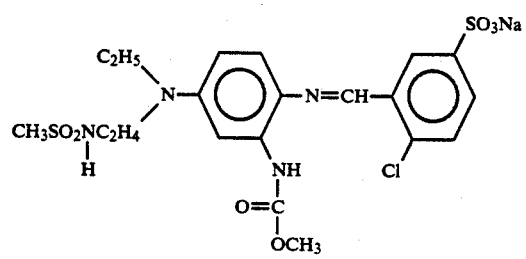 (49)
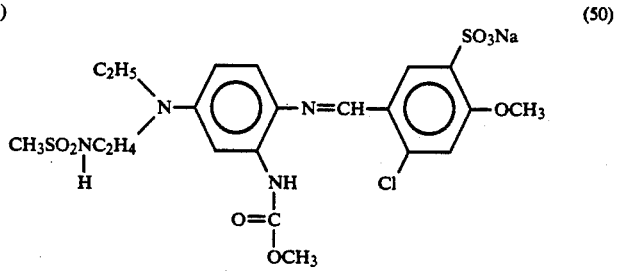 (50)
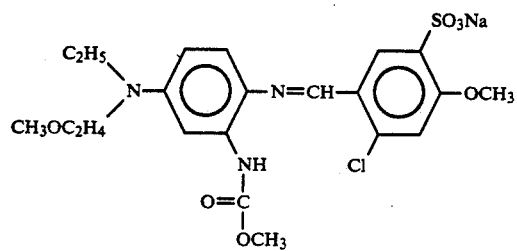 (51)
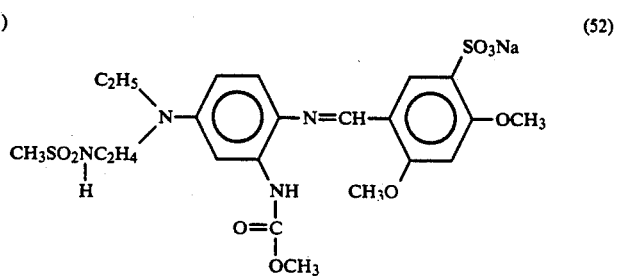 (52)
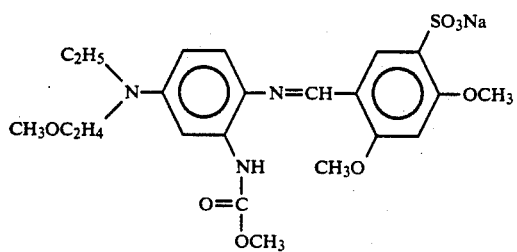 (53)
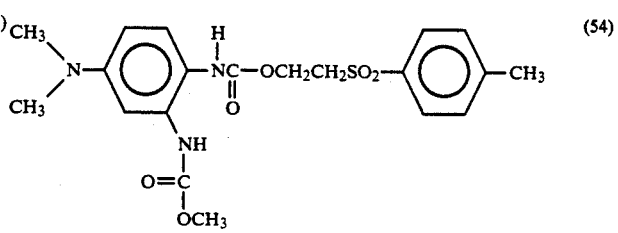 (54)
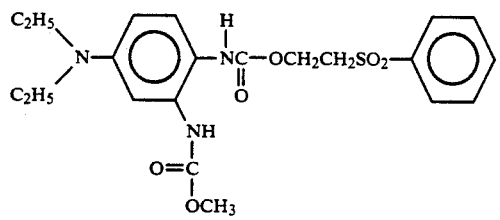 (55)
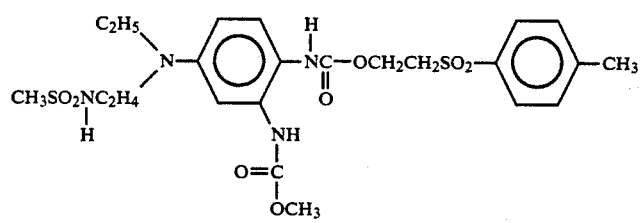 (56)
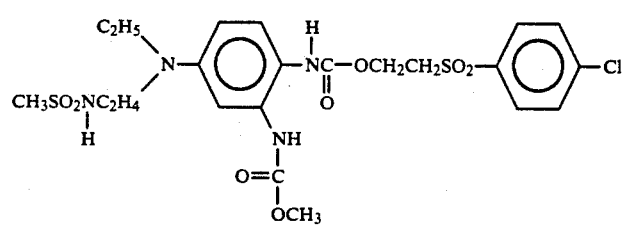 (57)

-continued
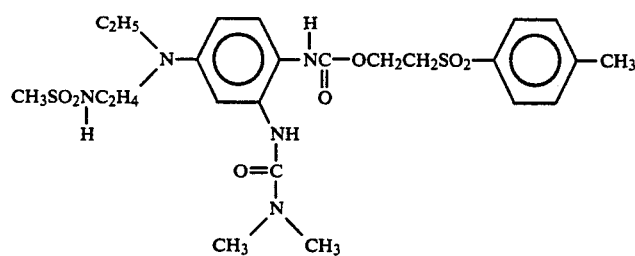 (58)
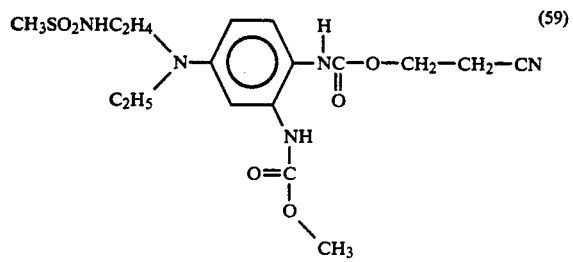 (59)
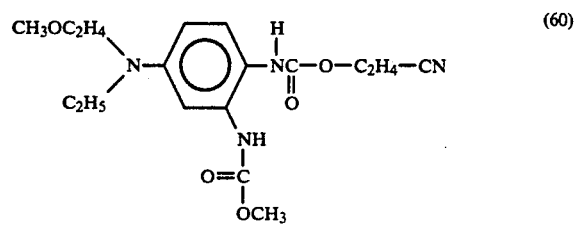 (60)
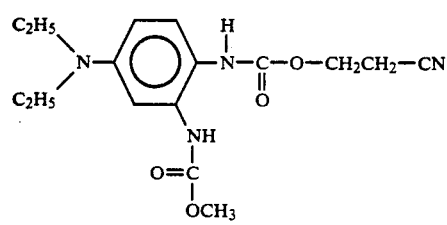 (61)
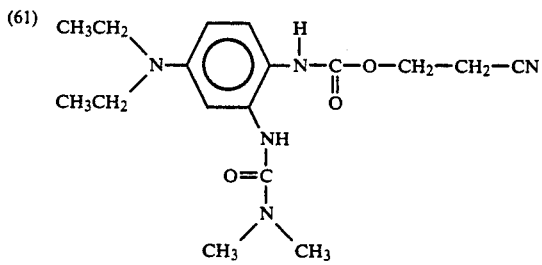 (62)
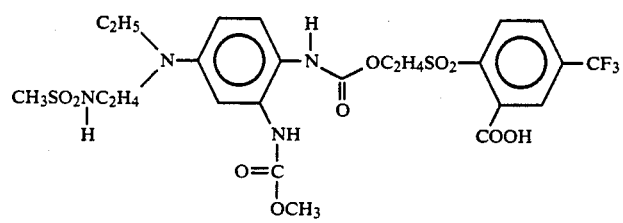 (63)
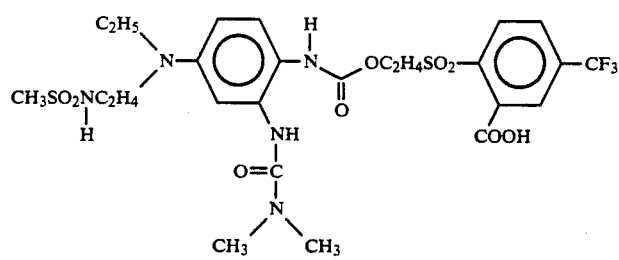 (64)
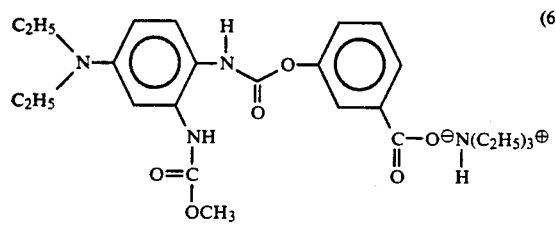 (65)
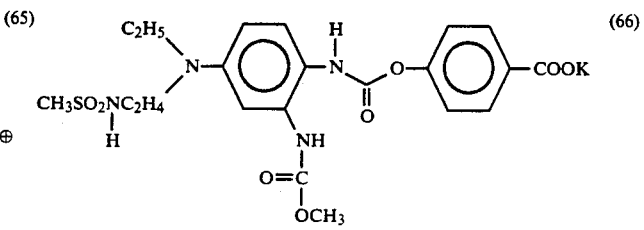 (66)

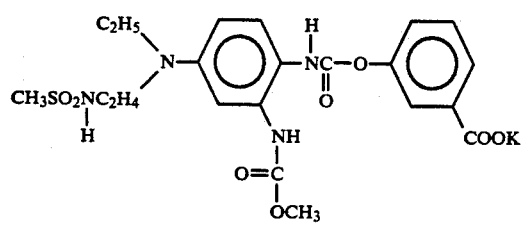 (67)

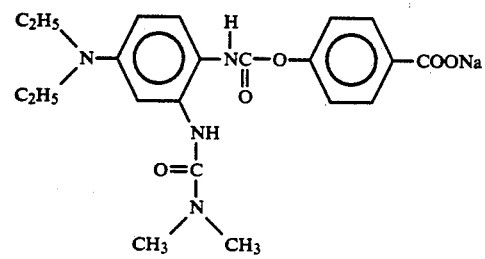 (69)

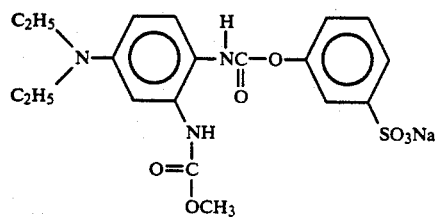 (71)

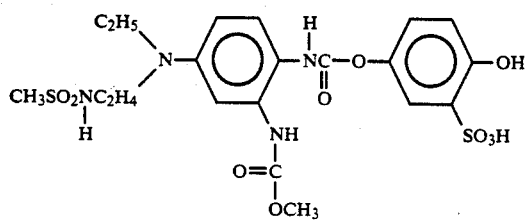 (73)

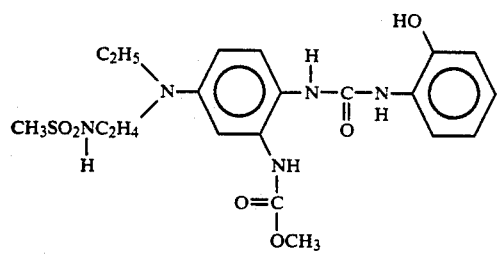 (75)

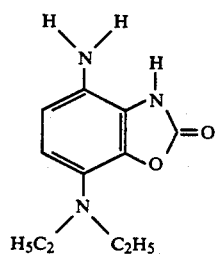 (77)

-continued

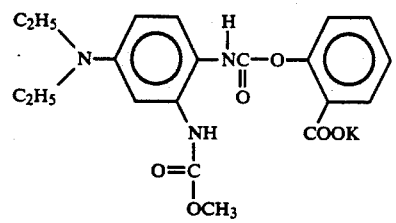 (68)

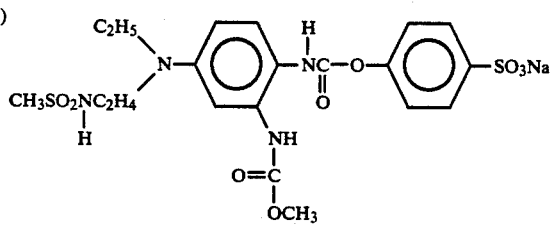 (70)

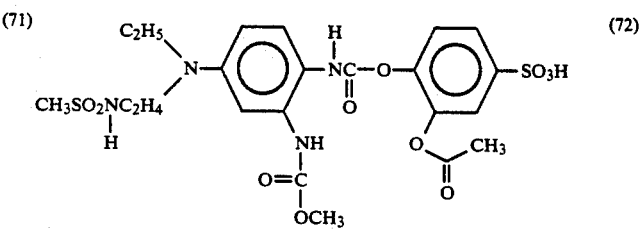 (72)

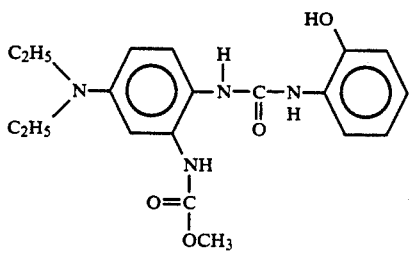 (74)

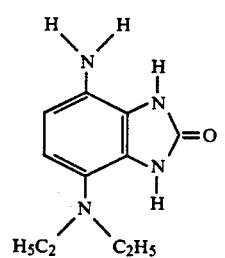 (76)

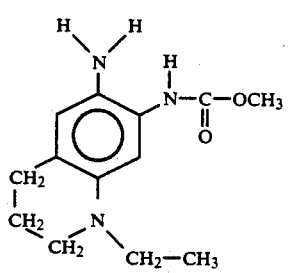 (78)

SYNTHESIS EXAMPLES

Then, a synthesis example of the compound of the present invention represented by formula (I) is described below.

(1) 3-(Methoxycarbonylamino)nitrobenzene

A mixture of 10 g of 3-nitroaniline and 100 ml of N,N-dimethylacetamide was stirred under ice cooling and 8.2 g of methyl chloroformate was added dropwise to the mixture. After stirring the mixture for 30 minutes, 300 ml of water was added to the reaction mixture and then the reaction mixture was neutralized by the addition of sodium bicarbonate to deposit crystals, which were recovered by filtration, washed with water, and dried. The amount of the product was 13.1 g (yield: 93%).

(2) 3-(Methoxycarbonylamino)aniline

After refluxing a mixture of 37 g of iron powder, 1.9 g of ammonium chloride, 33 g of water, 13 g of 3-(methoxycarbonylamino)nitrobenzene, and 260 g of 2-propanol for 30 minutes, the reaction mixture was filtered under suction using sellaite. After extracting the product formed from the filtrate with ethyl acetate followed by washing with water, the product was dried by Glauber's salt. The solvent was distilled off from the product using an evaporator to provide 10.5 g (yield: 95%) of a black oily product.

(3) 3-(Methoxycarbonylamino)-N,N-diethylaniline

A mixture of 4.5 g of 3-(methoxycarbonylamino)-aniline, 21.6 g of ethyl iodide, 14.4 g of sodium carbonate, and 90 ml of N,N-diethylacetamide was stirred for 1 hour at 110° C. The reaction mixture obtained was poured into 300 ml of water followed by stirring well and extracted with ethyl acetate. The extract was washed with water, dried by Glauber's salt, and the solvent was distilled off using a rotary evaporator to provide 6.0 g (yield: 100%) of an oily product.

(4) 3-(Methoxycarbonylamino)-4-nitroso-N,N-diethylaniline

While stirring a mixture of 6.0 g of 3-(methoxycarbonylamino)-N,N-diethylaniline, 10 ml of water, and 2.0 ml of concentrated hydrochloric acid at 0° C, 2.0 g of sodium nitrite was added to the mixture. When the first crystals were deposited in the mixture, 50 ml of water was further added to the mixture followed by stirring for 30 minutes. Thereafter, the reaction mixture obtained was poured into 300 ml of water followed by stirring well, neutralized by the addition of sodium bicarbonate, and extracted with ethyl acetate. After washing with water, the extract was dried by Glauber's salt and the solvent was distilled off using an evaporator to provide a yellow-green oily product. The crude product was purified by silica gel chromatography to provide 6.7 g (yield: 98%) of a product as a green solid.

(5) 3-(Methoxycarbonylamino)-4-amino-N,N-diethylaniline, di-p-toluenesulfonate (Compound (1))

In an autoclave were placed 4.0 g of 3-(methoxycarbonylamino)-4-nitroso-N,N-diethylaniline, 80 ml of ethanol, and 0.2 g of palladium carbon and hydrogen was charged therein at 20° C. and a pressure of 20 kg/cm$^2$. After 2 hours, the reaction mixture was filtered under suction using sellaite. Then, a solution of 6.0 g of p-toluenesulfonic acid hydrate in 100 ml of ethanol was immediately added to the product and the solvent was distilled off using an evaporator to provide 9.8 g (yield: 100%) of the desired product.

Schiff base precursors for a color developing agent as Compound (48) which is the precursor for Compound (1) can be synthesized from various kinds of arylaldehydes and aromatic primary amine developing agents according to the synthesis method described in JP-A-56-106241.

Arylsulfonylethylurethane type precursors for color developing agent as Compound (54) which is the precursor for Compound (5) can be synthesized from various kinds of arylsulfinic acids and aromatic primary amine developing agents according to the synthesis method described in JP-B-58-14671.

Cyanoethylurethane type precursors for color developing agent as Compound (59) which is the precursor for Compound (6) can be synthesized from various kinds of aromatic primary amine developing agents according to the synthesis method described in JP-B-58-14672.

Also, precursors for color developing agents of the types as Compounds (74) and (75) which are precursors for Compounds (1) and (6) can be synthesized from color developing agents, phosgene, and aniline derivatives according to the synthesis method described in JP-A-59-53831.

Other compounds illustrated above can be easily synthesized according to methods similar to the aforesaid methods.

Then, the embodiment of using the p-phenylenediamine derivative of the present invention for silver halide color photography is explained in detail.

The compound (p-phenylenediamine derivative) of the present invention can be used as a color developing agent or a precursor thereof in the case of carrying out color development in the presence of color couplers. When the compound of the present invention is used in a color developer, the compound can be used as a main component for an alkaline aqueous solution.

The content of the color developing agent in a color developer is preferably from $1 \times 10^{-3}$ to $1 \times 10^{-1}$ mol/liter, and more preferably from $5 \times 10^{-3}$ to $5 \times 10^{-2}$ mol/liter.

A color developer generally contains an alkali metal carbonate, a pH buffer such as a borate and a phosphate, and a development inhibitor or an antifoggant such as bromides, iodides, benzimidazoles, benzothiazoles, and mercapto compounds in addition to a color developing agent.

Also, if desired, the color developer may further contain a preservative such as hydroxylamine, diethylhydroxylamine, sulfites, hydrazines, phenyl semicarbazides, triethanolamine, catecholsulfonic acids, triethylenediamine(1,4-diazabicyclo[2,2,2]octanes); an organic solvent such as ethylene glycol and diethylene glycol; a development accelerator such as benzyl alcohol, polyethylene glycol, quaternary ammonium salts, and amines; a dye forming coupler; a competing coupler; a fogging agent such as sodium boron hydride; an auxiliary developing agent such as 1-phenyl-3-pyrazolidone; a tackifier, a chelating agent such as aminopolycarboxylic acid, aminopolysulfonic acid, alkylphosphonic acid, and phosphonocarboxylic acid (e.g., ethylenediaminetetraactic acid, nitrilotriacetic acid, diethylenetriaminepentaacetic acid, cyclohexanediaminetetraacetic acid, hydroxyethyliminodiacetic acid, 1-hydroxyethylidene-1,1-diphosphonic acid, nitrilo-N,N,N-trimethylenephosphonic acid, ethylenediamine-N,N,,N,-tetramethylenephosphonic acid, ethylenediamine-di(o-hydroxyphenylacetic acid) and the salts thereof).

In addition, when the color developing agent of the present invention is used, benzyl alcohol can be substantially omitted (e.g., less than 1 ml/liter) or preferably omitted from the color developer, which is preferred in the point of reducing a load for pollution.

In the case of carrying out reversal processing, color development is usually carried out after carrying out a black-and-white development. For the black-and-white eeveloper, known black-and-white developing agents such as dihydroxybenzenes (e.g., hydroquinone, 3-pyrazolidones (e.g., 1-phenyl-3-pyrazolidone), and aminophenols (e.g., N-methyl-p-aminophenol) can be used singly or as a combination thereof.

The pH of the color developer and the black-and-white developer is generally from 9 to 12. Also, the amount of replenishers for these developers are generally less than 3 liters per square meter of a color photographic material although the amount differs according to the kind of the color photographic material being processed, and also the amount can be reduced not more than 500 ml by reducing the bromide ion concentration in the replenisher. When the amount of the replenisher is reduced, it is preferred to inhibit the occurrence of the evaporation of the developer and the air oxidation of the developer by reducing the contact area of the developer in the processing bath with air. Also, the amount of the replenisher can be reduced by using a means of restraining the accumulation of bromide ions in the developers.

After color development, the photographic emulsion layers are usually bleached. The bleach process may be carried out simultaneously with blix processing or separately from a fix process. Furthermore, for quickening processing, a processing process of carrying out a blix process after the bleach process may be employed. Furthermore, a system of processing with blix baths composed of two baths continuously connected, a system of fixing before a blix process, or a system of bleaching after a blix process can be optionally employed according to the purpose.

As the bleaching agent, there are, for example, compounds of multivalent metal such as iron(III), cobalt-(III), chromium(VI), copper(II), etc., peroxides, quinones and nitro compounds.

Typical examples of the bleaching agent include ferricyanides; bichromates; organic complex salts of iron-(III) or cobalt(III); complex salts of aminopolycarboxylic acids (e.g., ethylenediaminetetraacetic acid, diethylenetriaminepentaacetic acid, cyclohexanediaminetetraacetic acid, methyliminodiacetic acid, 1,3-diaminopropanetetraacetic acid, and glycoletherdiaminetetraacetic acid) or citric acid, tartaric acid, malic acid, etc.; persulfates; bromates; permanganates; and nitrobenzenes. Among bleaching agents, aminopolycarboxylic acid iron(III) complex salts such as ethylenediaminetetraacetic acid iron(III) complex salt, etc., and persulfates are preferred from the viewpoints of quick processing and the prevention of environmental contamination.

Furthermore, aminopolycarboxylic acid iron(III) complex salts are particularly useful in a bleach solution and a blix solution.

The pH of the blech solution or blix solution using the aminopolycarboxylic acid iron(III) complex salt is usually from 5.5 to 8 but for quickening the processing, a bleach solution or blix solution having a lower pH can be employed.

For the bleach solution, the blix solution and prebaths thereof, a bleach accelerator can be, if desired, used. Practical examples of the bleach accelerator include compounds having a mercapto group or a disulfide bond described in U.S. Pat. No. 3,893,858, West German Patent 1,290,812, JP-A-53-95630, *Research Disclosure*, No. 17129 (July, 1978), etc.; thiazolidine derivatives described in JP-A-50-140129; thiourea derivatives described in U.S. Pat. No. 3,706,561; iodides described in JP-A-58-16235; polyoxyethylene compounds described in West German Patent 2,748,430; polyamine compounds described in JP-B-45-8836; and bromide ions. In these compounds, the compounds having a mercapto group or a disulfide bond are preferred from the viewpoint of giving a large acceleration effect and the compounds described in U.S. Pat. No. 3,893,858, West Germah Patent 1,290,812 and JP-A-53-95630 are particularly preferred. Furthermore, the compounds described in U.S. Pat. No. 4,552,834 are also preferred.

These beach accelerators may be incorporated in color photographic light-sensitive materials. The use of these bleach accelerators is particularly effective when a color photographic light-sensitive material for photography is blixed.

As a fixing agent, there are thiosulfates, thiocyanates, thioether series compounds, thioureas, and a large amount of an iodide. However, a thiosulfate is generally used and, in particular, ammonium thiosulfate is most widely used.

As preservatives for a blix solution, there are sulfites, hydrogensulfites, sulfinic acids, and carbonylhydrogensulfite addition products.

The silver halide color photographic material for use in the present invention is generally washed and/or stabilized after the desilvering process. The amount of water in the wash step can be widely selected according to the characteristics (e.g., materials such as couplers, etc.) and the use of the color photographic material, the temperature of the wash water, the number (stage number) of wash tanks, the replenishing system such as countercurrent system and cocurrent system, and other various conditions. Among them, the relation between the number of wash tanks and the amount of water in the multistage countercurrent system can be obtained by the method described in *Journal of the Society of Motion Picture and Television Engineers*, Vol. 64, pp. 248 to 253 (May, 1955).

By the multistage countercurrent system described in the aforesaid literature, the amount of wash water can be greatly reduced but the increase of the residence time causes a problem of growing bacteria and floats attaching to light-sensitive materials. In the process for color photographic materials of the present invention, the method of reducing calcium ions and magnesium ions as described in JP-A-62-288838 can be very effectively used for solving the aforesaid problem. Also, chlorine series antibacterial agents such as isothiazolone compounds, thiabendazoles, chlorinated sodium isocyanurate, etc., described in JP-A-57-8542, benzotriazole, and antibacterial agents described in Hiroshi Horiguchi, *Bokin Bobai Zai no Kagaku (Chemistry of Antibacterial and Antifungal Agents), Biseibutsu no Mekkin, Sakkin, Bobai Gijutsu (Antibacterial and Antifungal Techniques of Microorqanisms)*, edited by Eiseigijutsu Kai, and *Bokin Bobai Zai Jiten (Antibacterial and Antifungal Agents Handbook)*, edited by the Antibacterial and Antifungal Society of Japan can be used.

The pH of wash water in the processing process for color photographic materials in the present invention is generally from 4 to 9 and preferably from 5 to 8. The temperature of the wash water and the washing time can be variously selected according to the characteristics and use of the color photographic material being processed but are generally selected in the range of from 15° to 45° C. and from 20 seconds to 10 minutes and preferably from 25° to 45° C. and from 30 seconds to 5 minutes.

Furthermore, the color photographic material can be processed directly by a stabilization solution in place of the aforesaid wash process. In such a stabilization process, known processes described in JP-A-57-8543, JP-A-58-14834 and JP-A-60-220345 can be used.

Also, as the case may be, the stabilization process is applied after the aforesaid wash process, and as an example thereof a stabilization bath containing formalin and a surface active agent is used as the final bath for processing color photographic materials for photography. The stabilization bath can contain a chelating agent and an antifungal agent.

The overflow solution caused with the supply of the replenisher for the aforesaid wash water and/or stabilization solution can be reused for the desilvering step, etc.

The silver halide color photographic material being processed by the process of the present invention can contain color developing agents for simplifying and quickening processing thereof. For the purpose of incorporation in the color photographic material, a precursor for a color developing agent is preferably used.

The silver halide color photographic material being processed by the process of the present invention may further contain various kinds of 1-phenyl-3-pyrazolidones for accelerating the color development and typical examples of these compounds are described in JP-A-56-64339, JP-A-57-144547 and JP-A-58-115438.

Various processing solutions in the present invention are used at a temperature of from 10° C. to 50° C. A standard processing temperature is usually from 33° C. to 38° C. but a higher processing temperature may be employed for quickening processing to shorten the processing time or a lower processing temperature may be employed for improving the image quality or the stability of the processing solutions. Furthermore, for silver saving of color photographic materials, a process using a cobalt intensification or a hydrogen peroxide intensification described in West German Patent 2,226,770 and U.S. Pat. No. 3,674,499 may be applied.

The color developer using the color developing agent of the present invention can be used for a processing step in any wet system. For example, the color developer can be applied for processing color photographic papers, color reversal photographic papers, color positive photographic films, color negative photographic films, color reversal photographic films, color direct positive photographic materials, etc. Among them, the application for color photographic papers, color negative photographic films, and color reversal photographic films are particularly preferred.

For silver halide emulsions of the color photographic materials being processed by the process of the present invention, various halogen compositions such as silver iodobromide, silver bromide, silver chlorobromide, silver chloride, etc., can be used.

In the case of performing quick processing or low replenishing processing in the present invention, a silver chlorobromide emulsion containing at least 60 mol% silver chloride or a silver chloride emulsion is preferably used and further a silver halide emulsion containing from 80 to 100 mol% silver chloride is particularly preferred. Also, if it is necessary to increase the sensitivity of the photographic material and also reduce the occurrence of fog at the production, storage, and/or processing of the photographic material, a silver chlorobromide emulsion containing at least 50 mol% silver bromide or a silver bromide emulsion is preferred and the silver halide emulsion containing at least 70 mol% silver bromide is more preferred. When the content of silver bromide is higher than 90 mol%, the application of quick processing becomes difficult but if a means for accelerating the development, such as a means of acting on a development accelerator such as a silver halide solvent, a fogging agent, a developing agent, etc., at processing is used, the developing rate can be increased to some extent without being restrained by the content of silver bromide.

In any case, a large content of silver iodide is undesirable and is preferably not more than 3 mol%. These silver halide emulsions are preferably used for mainly light-sensitive materials for print, such as color photographic papers, etc.

For color photographic materials for photography (negative photographic films, reversal photographic films, etc.), a silver iodobromide emulsion or a silver chloroiodobromide emulsion is preferably used and in these emulsions, the content of silver iodide is preferably from 3 to 15 mol%.

The silver halide grains for use in the present invention may have a different phase between the inside thereof and the surface layer (core/shell grains), may have a multiphase structure as the case of having a junction structure, or may have a uniform phase throughout the whole grains. These structures may exist as a mixture thereof.

The mean grain size (the diameter of the grain when the grain is a sphere or near sphere, the mean value based on the projected area of the edge length as the grain sizes when the grain is a cubic grain, or the sphere converted value when the grain is a tabular grain) of the aforesaid silver halide grains is preferably from 0.1 μm to 2 μm, and particularly preferably from 0.15 μm to 1.5 μm.

The grain size distribution may be narrow or broad but a so-called monodispersed silver halide emulsion having the value obtained by dividing the standard deviation value in the grain distribution curve of a silver halide emulsion by the mean grain size thereof (coefficient of variation) of less than 20%, and particularly preferably less than 15% is preferably used in the present invention. Also, for satisfying the gradation required for the color photographic material, two or more kinds of monodispersed silver halide emulsions (monodispersed emulsions having the aforesaid coefficient of variation are preferred) each having different mean grain size can be used in the same emulsion layer as a mixture thereof or as separate emulsion layers in emulsion layer(s)) having substantially same color sensitivity. Furthermore, a combination of two or more kinds of polydispersed silver halide emulsions or a combination of a monodispersed emulsion and a polydispersed emulsion can be used as a mixture or for multilayers.

The form of the aforesaid silver halide grains may be a regular crystal form such as cubic, octahedral, rhombic dodecahedral, tetradecahedral, etc.; a mixture thereof, an irregular crystal form such as spherical, etc., or a composite form of these crystal forms. Also, the silver halide grains may be tabular grains and in this case, a tabular grain silver halide emulsion wherein tabular silver halide grains having an aspect ratio of at least 5, and particularly at least 8, account for at least 50% of the total projected area of the silver halide grains can be used in the present invention. A mixture of these silver halide emulsions each containing silver halide grains having different crystal form may also be used. The silver halide emulsion may be of a surface latent image type for forming latent images mainly on the surface thereof or of an internal latent image type for forming latent images mainly in the inside of the grains.

The silver halide photographic emulsions of color photographic materials which are developed by a color developer containing the color developing agent or a precursor thereof of the present invention can be prepared by the methods described in Research Disclosure (RD), Vol. 176, Item No. 17643, Paragraphs I, II and III (December, 1978).

The aforesaid silver halide emulsions are usually physically ripened, chemically ripened, and spectrally sensitized at use. Additives being used in such steps are described in Research Disclosure, Vol. 176, No. 17643 (December, 1978) and ibid., Vol. 187, No. 18716 (November, 1979) and the portions thereof are shown in the following table.

Also, photographic additives for color photographic materials being developed by the color developer using the color developing agent or the precursor thereof of the present invention are described in the aforesaid two Research Disclosures and these portions are also shown in the following table.

| Additive | RD 17643 | RD 18716 |
| --- | --- | --- |
| 1. Chemical Sensitizers | Page 23 | Page 648, right column |
| 2. Sensitivity Increasing Agents | " | " |
| 3. Spectral Sensitizers | Pages 23–24 | Page 648, right column to page 649, right column |
| 4. Super Sensitizers | " | |
| 5. Brightening Agents | Page 24 | — |
| 6. Antifoggants and Stabilizers | Pages 24–25 | Page 649, right column |
| 7. Couplers | Page 25 | " |
| 8. Organic Solvents | Page 25 | " |
| 9. Light Absorbents and Filter Dyes | Pages 25–26 | Page 649, right column to page 650, left column |
| 10. Ultraviolet Absorbers | " | Page 649, right column to page 650, left column |
| 11. Stain Inhibitors | Page 25, | Page 650, left to right column |
| 12. Color Image Stabilizers | Page 25 | Page 650, left to right column |
| 13. Hardening Agents | Page 26 | Page 651, left column |
| 14. Binders | Page 26 | " |
| 15. Plasticizers, Lubricants | Page 27 | Page 650, right column |
| 16. Coating Aids, Surface Active Agents | Pages 26–27 | " |
| 17. Antistatic Agents | Page 27 | " |

For the color photographic materials being processed in the present invention can be used various kinds of color couplers. A color coupler is a compound capable of forming a dye by causing a coupling reaction with the oxidation product of an aromatic primary amine developing agent of the present invention. Typical examples of useful color couplers include naphtholic or phenolic compounds, pyrazolone or pyrazoloazole series compounds, and open chain or heterocyclic ketomethylene compounds.

Typical examples of cyan, magenta, and yellow couplers which can be used in the present invention are described in the patents cited in Research Disclosure, No. 17643, VII-D (December, 1978) and ibid., No. 18717 (November, 1979).

It is preferred that the color couplers being incorporated in the color photographic materials for use in the present invention are nondiffusible by having a ballast group or by being polymerized. 2-Equivalent couplers where the releasing group is substituted are preferred as compared with 4-equivalent couplers wherein the coupling active site has a hydrogen atom, since the amount of silver coated can be reduced. Furthermore, couplers giving colored dyes having a proper diffusibility, colorless couplers, DIR couplers releasing a development inhibitor with a coupling reaction, or couplers releasing a development accelerator with a coupling can be used.

Typical yellow couplers for use in the present invention are oil protected type acylacetamide series couplers and practical examples thereof are described in U.S. Pat. Nos. 2,407,210, 2,875,057 and 3,265,506.

In the present invention, 2-equivalent yellow couplers are preferably used and typical examples thereof are oxygen atom releasing type yellow couplers described in U.S. Pat. Nos. 3,408,194, 3,447,928, 3,933,501 and 4,022,620 and nitrogen atom releasing type yellow couplers described in JP-B-55-10739, U.S. Pat. Nos. 4,401,752 and 4,326,024, Research Disclosure, No. 18052 (April, 1979), British Patent 1,425,020, and West German Patent Applications (OLS) 2,219,917, 2,261,361, 2,329,587 and 2,433,812. The α-pivaloylacetanilide type couplers are excellent in the fastness of the colored dyes formed, in particular, in the light fastness thereof, and the α-benzoylacetanilide series couplers form dyes of high color density.

As magenta couplers being used in the present invention, there are oil protected type indazolone or cyanoacetyl series couplers, preferably 5-pyrazolone series couplers and pyrazoloazole series couplers such as pyrazolotriazoles.

The 5-pyrazolone series couplers having an arylamino group or an acylamino group at the 3-position thereof are preferred from the viewpoint of the hue of the colored dyes and the coloring density and typical examples thereof are described in U.S. Pat. Nos. 2,311,082, 2,343,703, 2,600,788, 2,908,573, 3,062,653, 3,152,896, and 3,936,015. Preferred releasing groups for the 2-equivalent 5-pyrazolone series magenta couplers include nitrogen atom releasing groups described in U.S. Pat. No. 4,310,619 and arylthio groups described in U.S. Pat. No. 4,351,897. Also, 5-pyrazolone series magenta couplers having a ballast group described in European Patent 73,636 give high coloring density.

Pyrazoloazole series magenta couplers include pyrazolobenzimidazoles described in U.S. Pat. No. 3,369,879, preferably pyrazolo[5,1-c][1,2,4]triazoles described in U.S. Pat. No. 3,725,067, pyrazolotetrazoles described in Research Disclosure, No. 24220 (June, 1984), and pyrazolopyrazoles described in ibid., No. 24230 (June, 1984). From the viewpoint of less yellow side absorption and high light fastness of colored dyes, imidazo[1,2,-b]pyrazoles described in European Patent 119,741 are preferred and pyrazolo[1,5-b][1,2,4]triazoles described in European Patent 119,860 are particularly preferred.

Cyan couplers for use in the present invention include oil protected type naphtholic and phenolic couplers.

Typical examples of the naphtholic cyan couplers are the naphtholic cyan couplers described in U.S. Pat. No. 2,474,293, and preferably oxygen atom releasing type 2-equivalent naphtholic cyan couplers described in U.S. Pat. Nos. 4,052,212, 4,146,396, 4,228,233 and 4,296,200. Also, typical examples of phenolic cyan couplers are described in U.S. Pat. Nos. 2,369,929, 2,801,171, 2,772,162 and 2,895,826.

Cyan couplers having high fastness to humidity and temperature are preferably used in the present invention and typical examples thereof are phenolic cyan couplers having an alkyl group having 2 or more carbon atoms at the meta-position of the phenol nucleus described in U.S. Pat. No. 3,772,002, 2,5-diacylamino-substituted phenolic cyan couplers described in U.S. Pat. Nos. 2,772,162, 3,758,308, 4,126,396, 4,334,011, and 4,327,173, West German Patent Application (OLS) 3,329,729 and JP-A-59-166956, and phenolic cyan couplers having a phenylureido goup at the 2-position and an acylamino group at the 5-position described in U.S. Pat. Nos. 3,446,622, 4,333,999, 4,451,559, and 4,427,767.

In the present invention, the graininess of color images formed can be improved by using a coupler giving a colored dye having a proper diffusibility together with the aforesaid coupler(s). About such couplers giving diffusible dyes, specific examples of the magenta couplers are described in U.S. Pat. No. 4,366,237 and British Patent 2,125,570, and specific examples of the yellow, magenta, and cyan couplers are described in European Patent 96,570 and West German Patent Application (OLS) 3,234,533.

The dye forming couplers and the specific couplers described above may form a dimer or a higher polymer. Typical examples of the polymerized dye forming couplers are described in U.S. Pat. Nos. 3,451,820 and 4,080,211. Also, specific examples of the polymerized magenta couplers are described in British Patent 2,102,173 and U.S. Pat. No. 4,367,282.

The various couplers for use in the present invention can be used for one light-sensitive emulsion layer as a mixture of two or more such couplers for meeting the properties required for the color photographic material or the same kind of coupler may be incorporated in two or ore photographic emulsion layers.

The couplers for use in the present invention can be introduced into silver halide emulsions by various dispersion methods such as the oil-drop-in-water dispersion method. Examples of a high boiling point organic solvent which is used for the oil-drop-in-water dispersion method are described in U.S. Pat. No. 2,322,027.

Also, typical examples of the step and the effect of a latex dispersion method, which is one of polymer dispersion methods, and typical examples of a latex for impregnation are described in U.S. Pat. No. 4,199,363 and West German Patent Applications (OLS) 2,541,274 and 2,541,230 and examples of a dispersion method by an organic solvent-soluble polymer are described in PCT Application No. JP 87/00492.

Examples of the high boiling point organic solvent being used for the aforesaid oil-drop-in-water dispersion method are phthalic acid alkyl esters (dibutyl phthalate, dioctyl phthalate, etc.), phosphoric acid esters (e.g., diphenyl phosphate, triphenyl phosphate, tricresyl phosphate, and dioctylbutyl phosphate), citric acid esters (e.g., tributyl acetylcitrate), benzoic acid esters (e.g., octyl benzoate), alkylamides (e.g., diethyllaurylamide), fatty acid esters (e.g., dibutoxyethyl succinate and diethyl azerate), and trimesic acid esters (e.g., tributyl trimesate).

Also, the high boiling point organic solvent may be used together with a low boiling point organic solvent having a boiling point of from 30° C. to 150° C., such as a lower alkyl acetate (e.g., ethyl acetate, butyl acetate), ethyl propionate, secondary butyl alcohol, methyl isobutyl ketone, $\beta$-ethoxyethyl acetate, methyl cellosolve acetate, etc.

A standard amount of the color coupler is in the range of from 0.001 mol to 1 mol per mol of the light-sensitive silver halide, with from 0.01 mol to 0.5 mol of a yellow coupler, from 0.003 mol to 0.3 mol of a magenta coupler, and from 0.002 mol to 0.3 mol of a cyan coupler, per mol of the light-sensitive silver halide being preferred.

The silver halide photographic emulsions for use in the present invention are coated on a flexible support, which is usually used for photographic light-sensitive materials, such as plastic films (e.g., films of cellulose nitrate, cellulose acetate, and polyethylene terephthalate) and papers or a rigid support such as glass, etc. Such supports and coating methods are described in Research Disclosure, Vol. 176, Item 17643, XV (page 27) and XVII (page 28) (December, 1978).

In the case of applying the present invention to color photographic papers, a reflective support is preferably used. The "reflective support" is a support having increased reflection for making clear dye images formed in the silver halide emulsion layers. The reflective support includes a support coated with a hydrophobic resin layer having dispersed therein a light-reflective material such as titanium oxide, zinc oxide, calcium carbonate, calcium sulfate, etc., and a support composed of a hydrophobic resin having dispersed therein the aforesaid light-reflective material.

The color developing agent or the precursor thereof of the present invention can be applied for a system of being incorporated in a color photographic light-sensitive material and obtaining color images through a color development step by processing with an alkali solution.

This system is explained in detail.

The color developing agent or the precursor thereof of the present invention can exist in an optical layer containing a hydrophilic colloid of a color photographic material. As such a layer, there are a surface protective layer, a light-sensitive layer (silver halide emulsion layer, etc.), an interlayer between a surface protective layer and a light-sensitive layer, another interlayer, and an image receiving layer (containing an oxidizing agent) for a color diffusion transfer process, but it is preferred that the compound of the present invention is incorporated in two hydrophilic colloid layers having a light-sensitive layer sandwiched between them.

The color developing agent or the precursor thereof of the present invention is incorporated in an aqueous solution of a hydrophilic colloid as follows.

That is, when the color developing agent or the precursor thereof of the present invention is water-soluble, an aqueous solution of the color developing agent or the precursor thereof can be added to an aqueous solution of a hydrophilic colloid. When the compound of the present invention is sparingly soluble in water (hydrophobic), a latex dispersion method or an oil-drop-in-water type emulsification dispersion method is effective. These dispersion methods are well known. For example, a latex dispersion method is described in JP-A-49-74538 and JP-A-51-59943. An oil-drop-in-water type emulsification dispersion method is a conventional method which has hitherto been used for dispersing a hydrophobic additive such as a coupler, etc. Accordingly, in the case of applying the emulsification dispersion method, as an oil for dissolving the compound of the present invention, a coupler solvent shown below can be used.

For dispersing an oil phase having dissolved therein the compound of the present invention in an aqueous phase, a surface active agent is usually used. Examples of the surface active agent are anionic surface active agents having an acid group such as a carboxylic acid group, a sulfonic acid group, a phosphoric acid group, a sulfuric acid ester group, a phosphoric acid ester group, etc., and nonionic, cationic, and amphoteric surface active agents. Practical examples thereof are well known in the field of art.

As a hydrophilic colloid which is used for the color photographic materials, gelatin as well as other polymers which are known as photographic binders can be used and a latex, etc., may be added thereto. Examples thereof are described in U.S. Pat. No. 3,518,088 and *Research Disclosure*, No. 148148, 50 (August, 1976).

Also, the coating composition containing the color developing agent or the precursor thereof of the present invention can contain a photographic antioxidant or a stabilizer, such as reductants (e.g., hydroquinone derivatives and ascorbic acid), hydroxylamines, sulfonyl compounds, active methylene compounds, etc.

The coating amount of the color developing agent or the precursor thereof of the present invention which is contained in the color photographic material is from 0.1 to 10 mol times, and preferably from 0.25 to 5 mol times the whole silver amount of the color photographic material per unit area.

The developing process for processing the color photographic material using the color developing agent or the precursor thereof of the present invention differs from a conventional color developing process in only the point that an alkali activator bath can be used in place of a color development bath. Thus, after the color development by the activator bath, the color photographic material can be processed by conventional processing steps as they are. In other words, the steps after the color development step are fundamentally a desilvering step composed of a bleach step and a fix step, these steps may be carried out separately or simultaneously.

In a practical processing process, auxiliary step(s) for keeping a good photographic and physical quality of images or improving the storage stability of images are employed in addition to the aforesaid fundamental steps of color development and desilvering. For example, there are steps using a hardening bath for preventing the photographic layers of the color photographic material from being extremely softened during processing, a stopping bath for effectively stopping the development reaction, an image stabilizing bath for stabilizing images, and a bath for removing a backing layer from a support.

The activator bath which is used for processing the color photographic material containing the color developing agent or the precursor thereof of the present invention corresponds fundamentally to a conventional color developer from which a color developing agent is omitted. Accordingly, material known as an additive for a conventional color developer can be used for the activator bath in the present invention. Practical examples of them are described in JP-A-52-27638 and JP-A-50-145125. In a color diffusion transfer process, it is preferred to add a black-and-white developing agent such as phenidone, etc., to the activator bath.

It is preferred that when the precursor of the present invention is used, the pH of the activator bath is relatively higher than that of a conventional color developer to quickly decompose the precursor by an alkali. Practically, the pH is preferably in the range of from about 10 to 14. The activator bath can be used in the range of from 20° C. to 70° C., and preferably from 30° C. to 60° C.

As ordinary nondiffusible color couplers for use in the color photographic materials containing the color developing agent or the precursor for color developing agent of the present invention, there are conventionally known couplers described hereinbefore. So-called DIR couplers, i.e., couplers releasing a development inhibitor at the coupling reaction and compounds releasing a development inhibitor at coupling reaction can also be used for the color photographic materials.

Examples of these couplers are described in U.S. Pat. Nos. 3,148,062, 3,227,554, 3,253,924, 3,617,291, 3,622,328, 3,705,201, 3,297,445, 3,379,529 and 3,639,417 and British Patent 1,201,110.

The aforesaid couplers, etc., can be used for the same emulsion layer as a mixture of two or more kinds or the same coupler or compound can be used for two or more different emulsion layers for meeting the characteristics required for the color photographic materials.

The couplers can be dispersed in an aqueous solution of a hydrophilic colloid by a latex dispersing method or an oil-drop-in-water type emulsification dispersing method.

It is preferred that the couplers are soluble in a coupler solvent (preferably, an oil having a proper polarity) and insoluble in water. Typical examples of the useful solvent include tri-o-cresyl phosphate, trihexyl phosphate, dioctylbutyl phosphate, dibutyl phthalate, diethyllaurylamide, 2,4-diallylphenol, and the compounds described in *Product Licensing Index*, Vol. 83, pp. 26 to 29 (March, 1971) as the name of "Color Image Stabilizing Solvents for Improved Type Photography".

The silver halide emulsions which are used for the color photographic materials using the color developing agents or the color developing agent precursors of the present invention can be produced by conventionally known methods. That is, there is no particular restriction on the materials such as silver halide and binder, which are used at the production of the silver halide emulsions, photographic additives such as chemical sensitizers, spectral sensitizers, etc., and the methods and supports for coating the silver halide emulsions, and conventional ones can be used as they are. Practical examples thereof are described in JP-A-52-27638 and JP-A-50-145125.

Furthermore, the silver halide emulsions for use in the present invention may be of a surface latent image type or an internal latent image type. Also, when the silver halide emulsion for use in the present invention is a direct positive silver halide emulsion, the emulsion may be of the type being previously fogged before image exposure or of the type being fogged after image exposure.

The color photographic materials for use in the present invention may be, for example, color photographic negative films, color photographic positive films, color photographic papers, color diffusion transfer photographic film units, etc.

Then, the color developing agent or the precursor for color developing agent of the present invention can be applied to a system of incorporating the compound in a color photographic material and obtaining color images through a heat development step.

The compounds (the color developing agents or the color developing agent precursors) of the present invention which are used for a heat developable color photographic material can be used singly or as a combination of two or more. Also, the amount thereof depends upon the kind of a silver salt oxidizing agent (organic silver salt, etc.) being used, the kind of light-sensitive silver halide, and the kind of other additives being used, if desired, but is usually in the range of from 0.05 mol to 10 mols, and preferably from 0.1 mol to 3 mols, per mol of the silver salt oxidizing agent in the heat developable color photographic material.

The addition mthod of the compound of the present invention is optional. For example, in the case of using a hydrophilic binder, the compound of the present invention may be added to an aqueous solution of the hydrophilic colloid as a solution in a hydrophilic solvent or may be dispersed therein as a solution in a solvent immiscible with water by a method known in the field of art. On the other hand, in the case of using a hydrophobic binder, the compound can be added to a solution of the binder in a nonaqueous solvent as a solution thereof in a solvent which has a miscibility with the binder solvent and does not deposit the binder in the binder solution or if the compound is soluble in only a solvent immiscible with the solvent of the binder solution, the compound may be dispersed in the binder solution as a solution thereof in the solvent.

As dye providing materials which are used in the case of applying the color developing agent or the color developing agent precursor of the present invention for a heat developable color photographic material, there are those described in JP-A-62-44737, couplers forming nondiffusible dyes described in JP-A-62-129852 and JP-A-62-169158, leuco dyes described in U.S. Pat. No. 475,441, and azo dyes for a heat developable dye bleach process described in U.S. Pat. No. 4,235,957 but diffusible dye providing materials forming or releasing a diffusible dye are preferably used and compounds forming a diffusible dye by a coupling reaction are particularly preferred. The diffusible dye providing materials, negative type dye providing materials and the using methods thereof are described in JP-A-62-44737.

Also, light-sensitive silver halide emulsions which are used for the heat developable color photographic materials and the chemical sensitizing methods and spectral sensitizing methods of the silver halide emulsions are described in JP-A-63-301037. Also, organic silver salts which are used, if desired, for improving the sensitivity of the silver halide emulsions and the amounts thereof are described in said JP-A-63-301037.

Furthermore, a color developing agent which is usually used in the field of a heat developable light-sensitive material can be used together with the color developing agent or the color developing agent precursor of the present invention. Practical examples of such developing agent are described in JP-A-63-301037.

Also, binders and supports which are used for the heat developable color photographic materials in the present invention are practically described in the aforesaid JP-A-63-301037.

In the case of the heat developable color photographic material or in the case wherein the heat developable color photographic material is of a transfer type and has an image receiving member, it is preferred that various kinds of heat solvents are added to the heat developable color photographic material and/or the image receiving member. A heat solvent is a compound capable of accelerating the heat development and/or the heat transfer.

Practical examples of the heat solvent are described in U.S. Pat. Nos. 3,347,675 and 3,667,959, JP-A-63-301037 and Research Disclosure, No. 17643, XII.

When the present invention is applied to a heat developable color photographic material of a transfer system, an image receiving member is formed as described above. The image receiving layer of the image receiving member which is effectively used in this case may have a function capable of receiving dyes of the heat developable light-sensitive emulsion layers released or formed by heat development. For the image receiving layer, for example, a polymer containing a tertiary amine or a quaternary ammonium salt described in U.S. Pat. No. 3,709,690 is preferably used. A typical image receiving layer for diffusion transfer is formed by coating a mixture of the polymer containing a quaternary ammonium salt or a tertiary amine and gelatin or other binder such as polyvinyl alcohol on a support. As other useful dye image receiving material for use in the present invention, there is a heat resisting organic high molecular compound having a glass transition temperature of from 40° C. to 250° C. described in JP-A-57-207250.

The aforesaid polymer or high molecular compound may be carried on a support as an image receiving layer or may be used as the support by itself.

The heat developable color photographic material containing the compound of the present invention may be a so-called monotone type heat developable light-sensitive material having a light-sensitive layer and an image receiving layer on the same support as described in Research Disclosure, No. 15108 and JP-A-57-198458, JP-A-57-207250, and JP-A-61-80148.

It is preferred that a protective layer is formed on the heat developable color photographic material in the present invention.

The following examples are intended to illustrate the present invention but not to limit it in any way.

EXAMPLE 1

On a paper support both surfaces of which were coated with polyethylene was formed the following layers to provide a multilayer color photographic paper.

The coating compositions for the layers were prepared as follows.

Preparation of Coating Composition for the First Layer

In 27.2 ml of ethyl acetate, 4.1 g of a solvent (Solv-3), and 4.1 g of a solvent (Solv-6) were dissolved 19.1 g of a yellow coupler (ExY), 4.4 g of a color image stabilizer (Cpd-1), and 1.8 g of a color image stabilizer (Cpd-7) and the solution was dispersed by emulsification in 185 ml of an aqueous solution containing 8 ml of 10 wt % sodium dodecylbenzenesulfonate. On the other hand, a silver chlorobromide emulsion (a mixture of a silver chlorobromide having silver bromide content of 80.0 mol%, cubic form, a mean grain size of 0.85 μm, and a variation coefficient of 0.08 and a silver chlorobromide having a silver bromide content of 80.0 mol%, a cubic form, a mean grain size of 0.62 μm, and a variation coefficient of 0.07 at a ratio of ⅓ by mol ratio of silver) was sulfur sensitized and added with a blue-sensitive sensitizing dye shown below at $5.0 \times 10^{-1}$ mol per mol of silver. The aforesaid emulsified dispersion was mixed with the silver halide emulsion and the composition of the mixture was adjusted as shown below to provide the coating composition for the First Layer. The solvents, coupler, and color image stabilizers used are shown below.

The coating composition for the Second Layer to the Seventh Layer were also prepared by the same manner as in the case of the coating composition for the First Layer. For each layer was used 1-oxy-3,5-dichloro-s-triazine sodium salt as a gelatin hardening agent.

Also, the following dyes were used as a spectral sensitizing dye for each layer.

Blue-Sensitive Emulsion Layer:

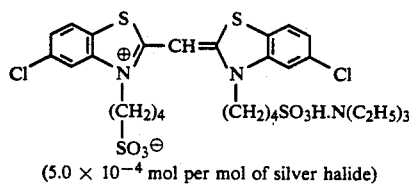

($5.0 \times 10^{-4}$ mol per mol of silver halide)

Green-Sensitive Emulsion Layer:

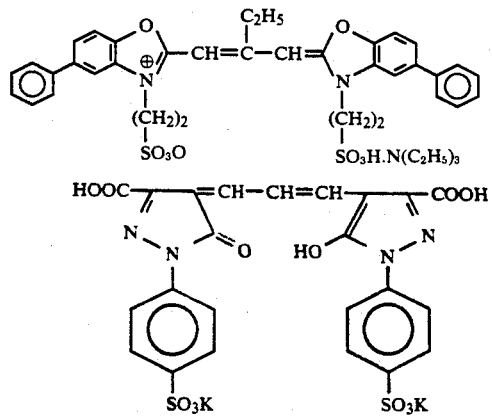

($4.0 \times 10^{-4}$ mol per mol of silver halide)

and

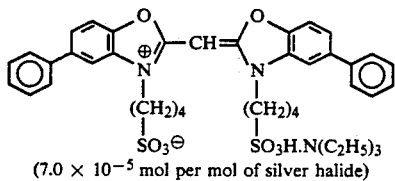

($7.0 \times 10^{-5}$ mol per mol of silver halide)

Red-Sensitive Emulsion Layer:

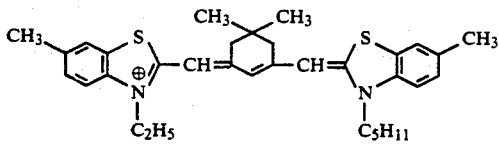

-continued ($0.9 \times 10^{-4}$ mol per mol of silver halide)

Also, to the red-sensitive emulsion layer was added the following compound in an amount of $2.6 \times 10^{-3}$ mol per mol of silver halide.

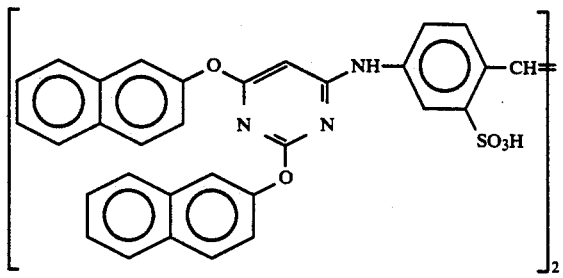

Also, to the blue-sensitive emulsion layer, the green-sensitive emulsion layer, and the red-sensitive emulsion layer was added 1-(5-methylureidophenyl)-5-mercaptotetrazole in an amount of $4.0 \times 10^{-6}$ mol, $3.0 \times 10^{-5}$ mol, and $1.0 \times 10^{-5}$ mol, respectively, per mol of silver halide and 2-methyl-5-t-octylhydroquinone in an amount of $8 \times 10^{-3}$ mol, $2 \times 10^{31\ 2}$, and $2 \times 10^{-2}$ mol, respectively, per mol of silver halide.

Further, to the blue-sensitive emulsion layer and the green-sensitive emulsion layer was added 4-hydroxy-6-methyl-1,3,3a,7-tetraazaindene in an amount of $1.2 \times 10^{-2}$ mol and $1.1 \times 10^{-2}$ mol, respectively, per mol of silver halide.

Furthermore, the following dyes were added to each silver halide emulsion layer for irradiation prevention.

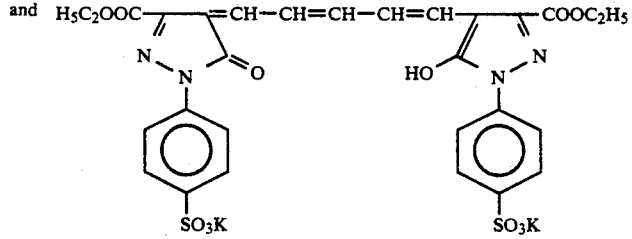

Layer Structure

The composition of each layer is shown below, wherein the numeral shows a coating amount (g/m²) but the coating amount of silver halide emulsion is shown as the calculated silver amount.

Support

A polyethylene-coated paper (containing a white pigment (TiO₂) and a bluish dye (ultramarine blue) in the polyethylene layer at the emulsion layer-carrying side)

| First Layer: Blue-Sensitive Emulsion Layer | |
|---|---|
| The Aforesaid Silver Chlorobromide Emulsion (AgBr: 80 mol %) | 0.26 |
| Gelatin | 1.83 |
| Yellow Coupler (ExY) | 0.83 |
| Color Image Stabilizer (Cpd-1) | 0.19 |
| Color Image Stabilizer (Cpd-7) | 0.08 |
| Solvent (Solv-3) | 0.18 |
| Solvent (Solv-6) | 0.18 |

-continued

| Second Layer: Color Mixing Inhibiting Layer | |
|---|---|
| Gelatin | 0.99 |
| Color Mixing Inhibitor (Cpd-6) | 0.08 |
| Solvent (Solv-1) | 0.16 |
| Solvent (Solv-4) | 0.08 |
| Third Layer: Green-Sensitive Emulsion Layer | |
| Silver Chlorobromide Emulsion (mixture of one having an AgBr content of 90 mol %, a cubic form, a mean grain size of 0.47 μm, and a variation coefficient of 0.12 and one having an AgBr content of 90 mol %, a cubic form, a mean grain size of 0.36 μm, and a variation coefficient of 0.09 at 1/1 by mol ratio of Ag) | 0.16 |
| Gelatin | 1.79 |
| Magenta Coupler (ExM) | 0.32 |
| Color Image Stabilizer (Cpd-3) | 0.20 |
| Color Image Stabilizer (Cpd-8) | 0.03 |
| Color Image Stabilizer (Cpd-4) | 0.01 |
| Color Image Stabilizer (Cpd-9) | 0.04 |
| Solvent (Solv-2) | 0.65 |
| Fourth Layer: Ultraviolet Absorption Layer | |
| Gelatin | 1.58 |
| Ultraviolet Absorbent (UV-1) | 0.47 |
| Color Mixing Inhibitor (Cpd-5) | 0.05 |
| Solvent (Solv-5) | 0.24 |
| Fifth Layer: Red-Sensitive Emulsion Layer | |
| Silver Chlorobromide Emulsion (mixture of one having an AgBr content of 70 mol %, a cubic form, a mean grain size of 0.49 μm, and a variation coefficient of 0.08 and one having an AgBr content of 70 mol %, a cubic form, a mean grain size of 0.34 μm, and a variation coefficient of 0.10 at 1/2 by mol ratio of Ag) | 0.23 |
| Gelatin | 1.34 |
| Cyan Coupler (ExC) | 0.30 |
| Color Image Stabilizer (Cpd-6) | 0.17 |
| Color Image Stabilizer (Cpd-7) | 0.40 |
| Solvent (Solv-6) | 0.20 |
| Sixth Layer: Ultraviolet Absorption Layer | |
| Gelatin | 0.53 |
| Ultraviolet Absorbent (UV-1) | 0.16 |
| Color Mixing Inhibitor (Cpd-5) | 0.02 |
| Solvent (Solv-5) | 0.08 |
| Seventh Layer: Protective Layer | |
| Gelatin | 1.33 |
| Acryl-Modified Copolymer (modification degree: 17%) of Polyvinyl Alcohol | 0.17 |
| Liquid Paraffin | 0.03 |

The compounds used for the aforesaid color photographic paper were as follows.

(Cpd-1) Color Image Stabilizer

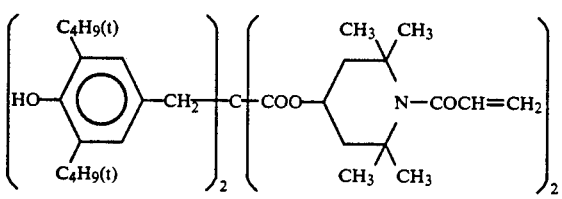

(Cpd-3) Color Image Stabilizer

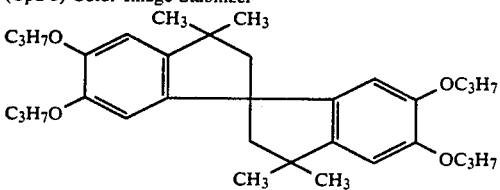

(Cpd-4) Color Image Stabilizer

-continued (Cpd-5) Color Mixing Inhibitor (Cpd-6) Color Image Stabilizer and

2/4/4 (by weight) mixture (Cpd-7) Color Image Stabilizer $+CH_2-CH\rightarrow_n$   Average molecular weight: 80,000
   |
   $CONHC_4H_9(t)$ (Cpd-8) Color Image Stabilizer (Cpd-9) Color Image Stabilizer (UV-1) Ultraviolet Absorbent -continued

[benzotriazole-phenol structure with C₅H₁₁(t) groups]

[chloro-benzotriazole-phenol structure with C₄H₉(t) groups] and

[benzotriazole-phenol structure with C₄H₉(sec) and C₄H₉(t)]

4/2/4 (by weight) mixture (Solv-1) Solvent

[phthalate structure with COOC₄H₉ groups]

(Solv-2) Solvent $$O=P\left(-OCH_2CH(C_2H_5)C_4H_9\right)_3 \text{ and}$$

$$O=P\left(-O-\text{[tolyl]}-CH_3\right)_3$$

2/1 (by weight) mixture (Solv-3) Solvent $$O=P\leftarrow O-C_9H_{19}(iso))_3$$

(Solv-4) Solvent $$O=P\left(-O-\text{[tolyl]}-CH_3\right)_3$$

(Solv-5) Solvent

COOC₈H₁₇
|
(CH₂)₈
|
COOC₈H₁₇

(Solv-6) Solvent

C₈H₁₇CHCH(CH₂)₇COOC₈H₁₇
        \O/

(ExY) Yellow Coupler

-continued

[pivaloylacetanilide structure]

CH₃   Cl
 \\   /
CH₃-C-CO-CH-CONH-[phenyl]
 /         |
CH₃        R
                  C₅H₁₁(t)
                  /
           NHCOCHO-[phenyl]-C₅H₁₁(t)
                |
                C₂H₅

R = [benzyl-hydantoin with OC₂H₅] and

R = [oxazolidinedione with CH₃, CH₃]

1/1 (by mol) mixture (ExM) Magenta Coupler

[pyrazolotriazole with CH₃, Cl, and phenyl-OCH₂CH₂OC₂H₅, NHSO₂ groups, OC₈H₁₇, C₈H₁₇(t)]

and

[pyrazolotriazole with CH₃, Cl, OCH₂CH₂OC₆H₁₃, NHSO₂, C₈H₁₇(t)]

1/1 (by mol) mixture (ExC) Cyan Coupler

[dichloro-ethyl-hydroxyphenyl-NHCOCHO-phenyl with C₅H₁₁(t), C₄H₉] and

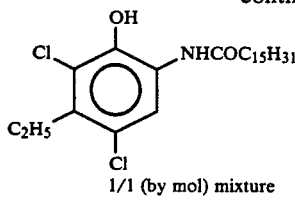

1/1 (by mol) mixture

The sample prepared as described above was imagewise exposed. Five such imagewise exposed samples were prepared, each sample was processed by each of five developers, i.e., Developers (A) to (C) shown below using the color developing agents of the present invention and Comparative Developers (D) and (E) using two kinds of comparative developing agents, and thereafter they were blixed and washed to provide five kinds of samples each having color images.

The processing was carried out using Fuji Color Paper Processor FPRP115 (trade name, manufactured by Fuji Photo Film Co., Ltd.). Thus, a continuous processing (running test) was carried out in the following processing steps until the amount of the replenisher replenished became twice the tank volume of the color developer.

| Processing Step | Temperature (°C.) | Time | Replenished Amount* (ml) | Tank Volume (liter) |
|---|---|---|---|---|
| Color Development | 37 | 3 min 30 sec | 200 | 60 |
| Blix | 33 | 90 sec | 55 | 40 |
| Wash (1) | 24–34 | 1 min | — | 20 |
| Wash (2) | 24–34 | 1 min | — | 20 |
| Wash (3) | 24–34 | 1 min | 10 | 20 |
| Drying | 70–80 | 1 min | | |

*Per square meter of the sample
(Three tank cascade of Wash (3) to Wash (1))

The composition of each processing solution was as follows.

| Color Developer: | Tank Solution | Replenisher |
|---|---|---|
| Water | 800 ml | 800 ml |
| Diethylenetriaminepentaacetic Acid | 1.0 g | 1.0 g |
| Nitrilotriacetic Acid | 2.0 g | 2.0 g |
| Benzyl Alcohol | 15 ml | 23 ml |
| Diethylene Glycol | 10 ml | 10 ml |
| Sodium Sulfite | 2.0 g | 3.0 g |
| Potassium Bromide | 1.2 g | — |
| Potassium Carbonate | 30 g | 25 g |
| Color Developing Agent (shown below) | 14 mmol | 24 mmol |
| Hydroxylamine Sulfate | 3.0 g | 4.5 g |
| Optical Brightening Agent (Whitex 4B, trade name, made by Sumitomo Chemical Co., Ltd.) | 1.0 g | 2.0 g |
| Water to make | 1,000 ml | 1,000 ml |
| pH (25° C.) | 10.20 | 10.80 |

Color Developing Agent

Developer (A):
 The p-toluenesulfonate of Compound (1) of the present invention
Developer (B):
 The 1,5-naphthalenedisulfonate of Compound (1) of the present invention
Developer (C):
 The p-toluenesulfonate of Compound (8) of the present invention
Developer (D):
 The sulfate of N-ethyl-N-[2-methylsulfonamido)-ethyl]-3-methyl-4-aminoaniline
Developer (E):
 The p-toluenesulfonate of N-ethyl(2-methoxyethyl)-3-methyl-4-aminoaniline

| Blix Solution: | Tank Solution | Replenisher |
|---|---|---|
| Water | 400 ml | 400 ml |
| Ammonium Thiosulfate (70 wt %) | 150 ml | 300 ml |
| Sodium Sulfite | 13 g | 26 g |
| Ethylenediaminetetraacetic Acid Iron (III) Ammonium | 55 g | 110 g |
| Ethylenediaminetetraacetic Acid Disodium | 5 g | 10 g |
| Water to make | 1,000 ml | 1,000 ml |
| pH (25° C.) | 6.70 | 6.30 |

The densities of yellow, magenta, and cyan were measured on each sample thus processed and also dyes formed were extracted from each sample, and absorption spectrum of each dye was measured, and a half value width was obtained from the result.

The results obtained are shown in Table 1 below.

TABLE 1

| | Yellow | | Magenta | | Cyan | |
|---|---|---|---|---|---|---|
| Developer | Dmax | Half Value Width (nm) | Dmax | Half Value Width (nm) | Dmax | Half Value Width (nm) |
| (A) | 2.27 | 81 | 2.65 | 60 | 2.50 | 90 |
| (B) | 2.28 | 81 | 2.65 | 60 | 2.51 | 90 |
| (C) | 2.22 | 81 | 2.61 | 61 | 2.48 | 92 |
| (D)* | 1.86 | 85 | 2.05 | 69 | 2.20 | 125 |
| (E)* | 2.40 | 90 | 2.20 | 69 | 2.30 | 121 |

Dmax: Maximum Density
*Comparison

From the results shown in Table 1, it can be seen that the maximum densities of yellow, magenta, and cyan of the samples obtained using Developers (A) to (C) containing the color developing agent precursors of the present invention are remarkably high as compared with the samples obtained using Comparative Developers (D) and (E) containing the comparative color developing agents. Also, the half value width is lower in the samples processed by the developers using the color developing agent precursors of the present invention than that of the comparative samples, which shows the absorption is sharp in the samples of the present invention.

EXAMPLE 2

By following the same procedure as in Example 1 except that benzyl alcohol was removed from the five kinds of color developers, the photographic performance of yellow, magenta and cyan were measured.

TABLE 2

| | Maximum Density | | |
|---|---|---|---|
| Developer | Yellow | Magenta | Cyan |
| (A) | 2.10 | 2.45 | 2.20 |
| (B) | 2.11 | 2.45 | 2.20 |
| (C) | 2.08 | 2.43 | 2.15 |
| (D)* | 1.60 | 1.75 | 1.85 |
| (E)* | 1.60 | 1.87 | 2.00 |

*Comparison

From the results shown in Table 2, it can be seen that the maximum densities of yellow, magenta, and cyan are greatly higher in the samples processed using Developers (A) to (C) containing the color developing agent precursors of the present invention than those of the comparative samples processed using Comparative Developers (D) and (E).

EXAMPLE 3

A multilayer color photographic paper having the following layers on a paper support both surfaces of which were coated with polyethylene was prepared. The coating compositions for the layers were prepared as follows.

Preparation of Coating Composition for the First Layer

In 27.2 ml of ethyl acetate and 8.2 g of a solvent (Solv-3) were dissolved 19.1 g of a yellow coupler (ExY), 4.4 g of a color image stabilizer (Cpd-1), and 0.7 g of a color image stabilizer (Cpd-7) and the solution was dispersed by emulsification in 18.5 ml of an aqueous solution of 10% gelatin containing 8 ml of an aqueous solution of 10% sodium dodecylbenzenesulfonate. On the other hand, a silver chlorobromide emulsion (a mixture of silver chlorobromide having a cubic form and a mean grain size of 0.88 μm and silver chlorobromide having a cubic form and a mean grain size of 0.70 μm at 3/7 by mol ratio of silver, the silver halides having a variation coefficient of grain size distribution of 0.08 and 0.10, respectively, and each silver halide containing 0.2 mol% of silver bromide localized at the surface of the grains) was added with the blue-sensitive sensitizing dye shown below in an amount of $2.0 \times 10^{-4}$ mol for the large grain size emulsion and $2.5 \times 10^{-4}$ mol for the small grain size emulsion per mol of silver and then subjected to a sulfur sensitization. The aforesaid emulsified dispersion was mixed with the silver halide emulsion and the composition of the resultant mixture was adjusted as shown below to provide a coating composition for the First Layer.

The coating compositions for the Second to Seventh Layers were also prepared by similar manner to the above. Also, 1-oxy-3,5-dichloro-s-triazine sodium salt was used for each layer as a gelatin hardening agent.

Furthermore, the following dyes were used for the emulsion layers as spectral sensitizing dyes.

Blue-Sensitive Emulsion Layer:

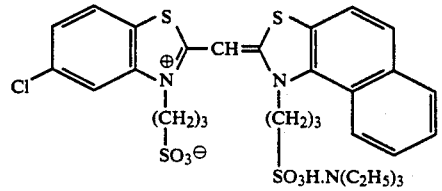

and

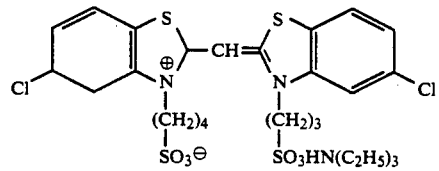

(the amount of each dye being $2.0 \times 10^{-4}$ mol for the large grain size emulsion and $2.5 \times 10^{-4}$ mol for the small grain size emulsion per mol of silver halide)

Green-Sensitive Emulsion Layer:

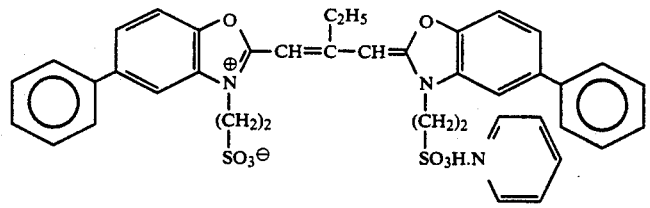

(the amount being $4.0 \times 10^{-4}$ mol for the large grain size emulsion and $5.6 \times 10^{-4}$ mol for the small grain size emulsion per mol of silver halide)

and

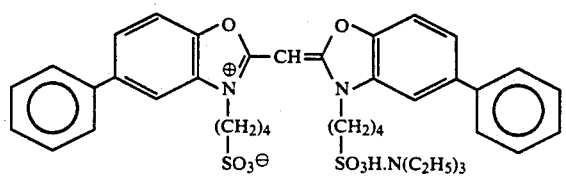

(the amount being $7.0 \times 10^{-5}$ mol for the large grain size emulsion and -continued 1.0 × 10$^{-5}$ mol for the small grain size emulsion per mol of silver halide)

Red-Sensitive Emulsion Layer:

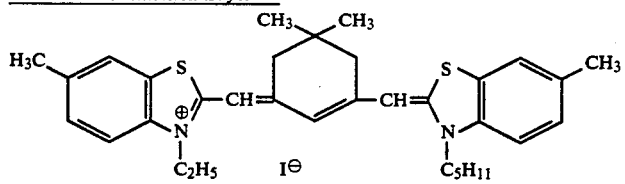

(the amount being 0.9 × 10$^{-4}$ mol for the large grain size emulsion and 1.1 × 10$^{-4}$ mol for the small grain size emulsion per mol of silver halide)

Also, the following composition was added to the red-sensitive emulsion layer at 2.6×10$^{-3}$ mol per mol of silver halide.

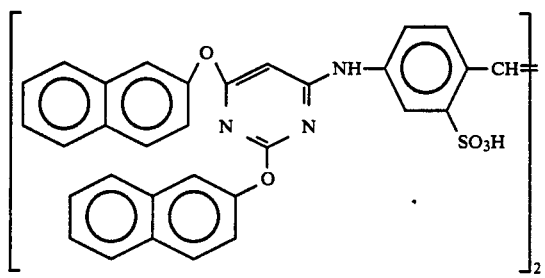

Also, to the blue-sensitive emulsion layer, the green-sensitive emulsion layer, and the red-sensitive emulsion layer was added 1-(5-methylureidophenyl)-5-mercaptotetrazole in an amount of 8.5×10$^{-5}$ mol, 7.7×10$^{-4}$ mol, and 2.5×10$^{-4}$ mol, respectively, per mole of silver halide.

Furthermore, the following dyes were added to each emulsion layer for irradiation prevention.

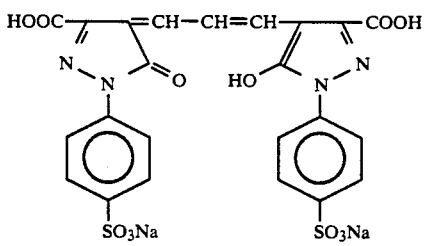

and

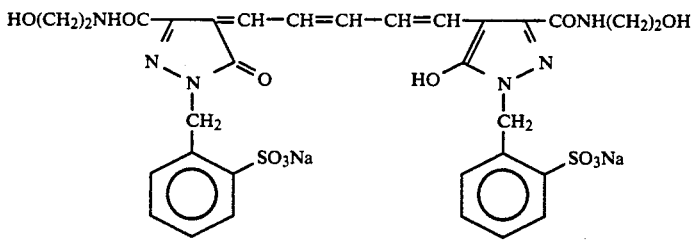

Layer Structure

The composition of each layer is shown below, wherein the numeral shows a coating amount (g/m$^2$) but the coating amount of silver halide emulsion is shown as the calculated silver amount.

Support

A polyethylene coated paper (containing a white pigment (TiO$_2$) and a bluish dye (ultramarine blue) in the polyethylene layer at the emulsion layer-carrying side)

| First Layer: Blue-Sensitive Emulsion Layer | |
|---|---|
| The Aforesaid Silver Chlorobromide Emulsion | 0.30 |
| Gelatin | 1.86 |
| Yellow Coupler (ExY) | 0.82 |
| Color Image Stabilizer (Cpd-1) | 0.19 |
| Solvent (Solv-3) | 0.35 |
| Color Image Stabilizer (Cpd-7) | 0.06 |
| Second Layer: Color Mixing Inhibition Layer | |
| Gelatin | 0.99 |
| Color Mixing Inhibitor (Cpd-5) | 0.08 |
| Solvent (Solv-1) | 0.16 |
| Solvent (Solv-4) | 0.08 |
| Third Layer: Green-Sensitive Emulsion Layer | |
| Silver Chlorobromide Emulsion (mixture of one having a cubic form and a mean grain size of 0.55 μm and one having a cubic form and a mean grain size of 0.39 μm at 1/3 by mol ratio of Ag, variation coefficients of grain size distributions of them being 0.10 and 0.08, respectively, and each silver halide containing 0.8 mol % AgBr localized at the surface of the grains) | 0.12 |
| Gelatin | 1.24 |
| Magenta Coupler (ExM) | 0.20 |
| Color Image Stabilizer (Cpd-3) | 0.15 |

| -continued | |
|---|---|
| Color Image Stabilizer (Cpd-4) | 0.02 |
| Color Image Stabilizer (Cpd-6) | 0.03 |
| Solvent (Solv-2) | 0.40 |
| Fourth Layer: Ultraviolet Absorption Layer | |
| Gelatin | 1.58 |
| Ultraviolet Absorbent (UV-1) | 0.47 |
| Color Mixing Inhibitor (Cpd-5) | 0.05 |
| Solvent (Solv-5) | 0.24 |
| Fifth Layer: Red-Sensitive Emulsion Layer | |
| Silver Chlorobromide Emulsion (mixture of one having a cubic form and a mean grain size of 0.58 μm and one having a cubic form and a mean grain size of 0.45 μm at 1/4 by mol ratio of Ag, variation coefficients of grain size distributions of them being 0.09 and 0.11, respectively, and each silver halide containing 0.6 mol % AgBr localized at the surface of the grains) | 0.23 |
| Gelatin | 1.34 |

| -continued | |
|---|---|
| Cyan Coupler (ExC) | 0.32 |
| Color Image Stabilizer (Cpd-6) | 0.17 |
| Color Image Stabilizer (Cpd-8) | 0.04 |
| Color Image Stabilizer (Cpd-7) | 0.40 |
| Solvent (Solv-6) | 0.15 |
| Sixth Layer: Ultraviolet Absorption Layer | |
| Gelatin | 0.53 |
| Ultraviolet Absorbent (UV-1) | 0.16 |
| Color Mixing Inhibitor (Cpd-5) | 0.02 |
| Solvent (Solv-5) | 0.08 |
| Seventh Layer: Protective Layer | |
| Gelatin | 1.33 |
| Acryl-Modified Copolymer (modification degree: 17%) of Polyvinyl Alcohol | 0.17 |
| Liquid Paraffin | 0.03 |

The compounds used for the aforesaid color photographic paper were as follows.

(ExY) Yellow Coupler

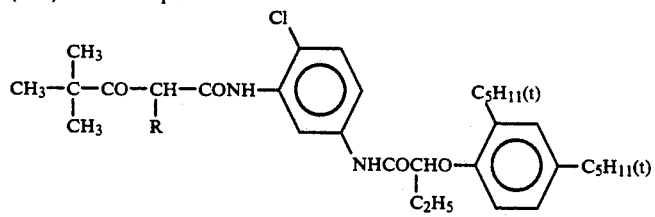

1/1 (by mol) mixture (ExM) Magenta Coupler

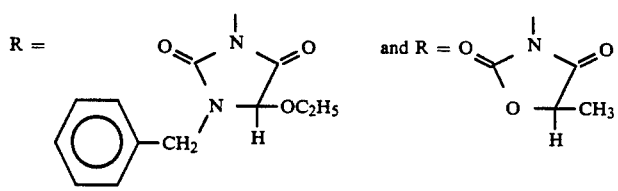

(ExC) Cyan Coupler

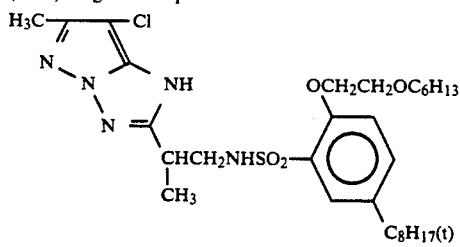

$R = C_2H_5$ and $C_4H_9$ and

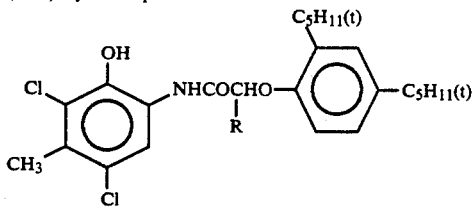

2/4/4 (by weight) mixture (Cpd-1) Color Image Stabilizer

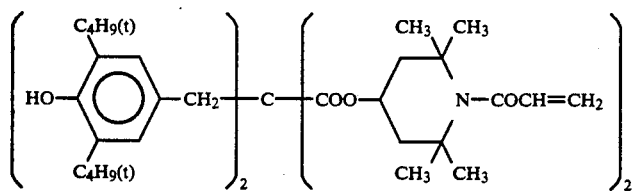
(Cpd-3) Color Image Stabilizer
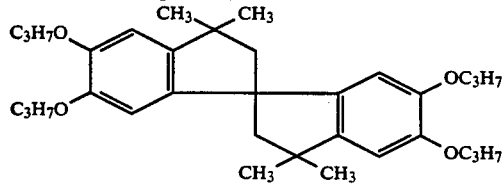
(Cpd-4) Color Image Stabilizer
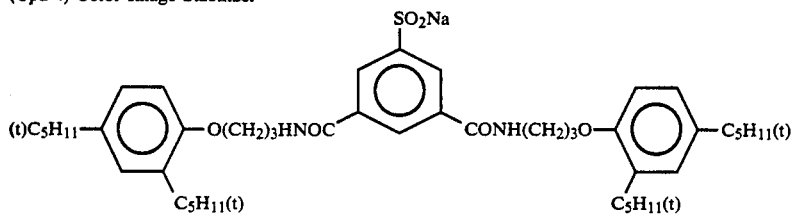
(Cpd-5) Color Mixing Inhibitor
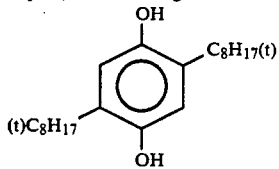
(Cpd-6) Color Image Stabilizer
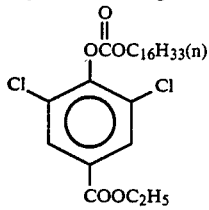
(Cpd-7) Color Image Stabilizer
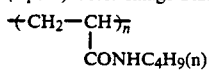
Average molecular weight: 60,000
(Cpd-8) Color Image Stabilizer
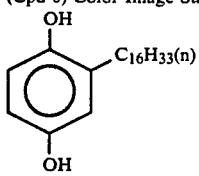
(UV-1) Ultraviolet Absorber
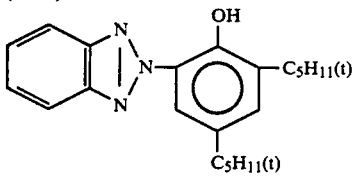

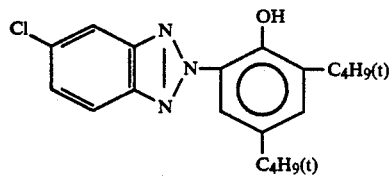

and

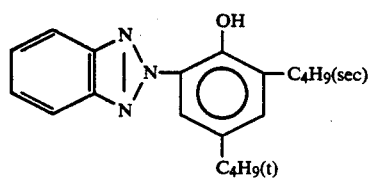

4/2/4 (by weight) mixture (Solv-1) Solvent

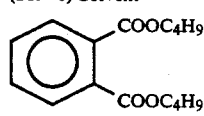

(Solv-2) Solvent

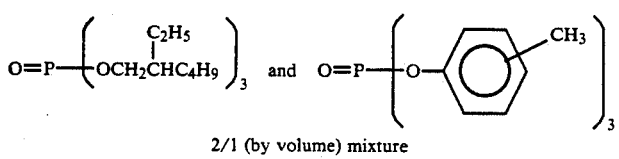

2/1 (by volume) mixture (Solv-3) Solvent
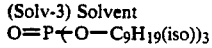
O=P(―O―C$_9$H$_{19}$(iso))$_3$ (Solv-4) Solvent

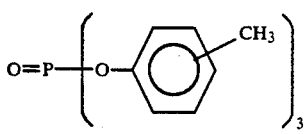

(Solv-5) Solvent
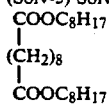
COOC$_8$H$_{17}$
|
(CH$_2$)$_8$
|
COOC$_8$H$_{17}$ (Solv-6) Solvent

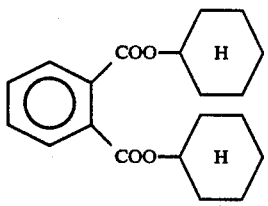

The color photographic paper thus prepared was imagewise exposed.

Five such imagewise exposed samples were prepared and each of the samples was developed by each of Developers (F) to (H) using the color developing agent precursors of the present invention shown below and Comparative Developers (I) and (J) using comparative color developing agent precursors shown below, blixed, and stabilized to provide five kinds of samples having color images.

| Processing Step | Temperature (°C.) | Time (sec) |
|---|---|---|
| Color Development | 35 | 45 |
| Blix | 30–36 | 45 |
| Stabilization (1) | 30–37 | 20 |
| Stabilization (2) | 30–37 | 20 |
| Stabilization (3) | 30–37 | 20 |
| Stabilization (4) | 30–37 | 30 |
| Drying | 70–85 | 60 |

(Four tank countercurrent system of from Stabilization (4) to Stabilization (1))

The compositions of the processing solutions were as follows.

| Color Developer: | |
| --- | --- |
| Water | 800 ml |
| Ethylenediaminetetraacetic Acid | 2.0 g |
| Triethanolamine | 8.0 g |
| Sodium Chloride | 1.4 g |
| Potassium Carbonate | 25 g |
| Color Developing Agent shown below | 14 mmol |
| N,N-Diethylhydroxylamine | 4.2 g |
| 5,6-Dihydroxybenzene-1,2,4-trisulfonic Acid | 0.3 g |
| Optical Brightening Agent (4,4'-diaminostilbene series) | 2.0 g |
| Water to make | 1,000 ml |
| pH (25° C.) | 10.10 |
| Color Developing Agent | |
| Developer (F): | |
| The p-toluenesulfonate of Compound (1) of the present invention | |
| Developer (G): | |
| The 1,5-naphthalenedisulfonate of Compound (1) of the present invention | |
| Developer (H): | |
| The p-toluenesulfonate of Compound (8) of the present invention | |
| Developer (I): | |
| The sulfate of N-ethyl-N-(2-methanesulfonamidoethyl)-3-methyl-4-aminoaniline | |
| Developer (J): | |
| The p-toluenesulfonate of N-ethyl-N-(2-methoxy-ethyl)-3-methyl-4-aminoaniline | |
| Blix Solution: | |
| Water | 400 ml |
| Ammonium Thiosulfate (70 wt %) | 100 ml |
| Sodium Sulfite | 18 g |
| Ethylenediaminetetraacetic Acid Iron (III) Ammonium | 55 g |
| Ethylenediaminetetraacetic Acid Disodium | 3 g |
| Glacial Acetic Acid | 8 g |
| Water to make | 1,000 ml |
| pH (25° C.) | 5.5 |
| Stabilization Solution: | |
| Formalin (37 wt %) | 0.1 g |
| Formalin-Sulfite Adduct | 0.7 g |
| 5-Chloro-2-methyl-4-isothiazolin-3-one | 0.02 g |
| 2-Methyl-4-isothiazolin-3-one | 0.01 g |
| Copper Sulfate | 0.005 g |
| Water to make | 1,000 ml |
| pH (25° C.) | 4.0 |

The maximum densities of yellow, magenta, and cyan were measured on each sample thus processed. The results obtained are shown in Table 3.

TABLE 3

| Developer | Maximum Density | | |
| --- | --- | --- | --- |
| | Yellow | Magenta | Cyan |
| (F) | 2.09 | 2.55 | 2.41 |
| (G) | 2.10 | 2.54 | 2.40 |
| (H) | 2.04 | 2.50 | 2.30 |
| (I)* | 1.80 | 2.12 | 2.01 |
| (J)* | 1.93 | 2.05 | 2.06 |

*Comparison

From the results shown in Table 3, it can be seen that the maximum densities of yellow, magenta, and cyan are very high in the samples developed by Developers (F) to (H) containing the compounds of the present invention as compared to the samples processed by Comparative Developers (I) and (J) containing the comparative color developing agents.

EXAMPLE 4

The color photographic papers prepared as in Example 3 were imagewise exposed by an ordinary manner. Each of the imagewise exposed samples was developed by each of the five kinds of the color developers as used in Example 3, and processed by a blix solution having a low pH for quickening the desilvering rate and then by a stabilization solution to provide five kinds of samples having color images.

| Processing Step | Temperature (°C.) | Time (sec) |
| --- | --- | --- |
| Color Development | 35 | 45 |
| Blix | " | 45 |
| Stabilization (1) | " | 20 |
| Stabilization (2) | " | 20 |
| Stabilization (3) | " | 20 |
| Stabilization (4) | " | 30 |
| Drying | 70–85 | 60 |

(Four tank countercurrent system of from Stabilization (4) to Stabilization (1))

The composition of the processing solutions were as follows.

| Color Developer: | |
| --- | --- |
| Same as the developer in Example 3. | |
| Blix Solution: | |
| Water | 400 ml |
| Sodium Thiosulfate (70 wt %) | 100 ml |
| Sodium Sulfite | 18 g |
| Ethylenediaminetetraacetic Acid Iron (III) Ammonium | 55 g |
| Ethylenediaminetetraacetic Acid Disodium | 3 g |
| Water to make | 1,000 ml |
| pH (25° C.) | 4.5 |

The pH was adjusted by adding glacial acetic acid.

Stabilization Solution

Same as in Example 3.

The maximum density of cyan was measured on each sample thus processed and the results obtained are shown in Table 4.

TABLE 4

| Developer | Maximum Density of Cyan |
| --- | --- |
| (F) | 2.37 |
| (G) | 2.36 |
| (H) | 2.25 |
| (I)* | 1.71 |
| (J)* | 1.80 |

*Comparison

From the results shown in Table 4, it can be seen that the samples processed by Developers (F) to (H) using the compounds of the present invention show less reduction of the maximum density of cyan even by using the blix solution having the low pH as compared to the samples processed by Developers (I) and (J) using the comparative color developing agents. Thus, it can be also seen that in the case of using the color developing agents of the present invention, the occurrence of fading of cyan color images at the reduction of pH in the blix solution is less.

EXAMPLE 5

A multilayer color photographic material having the following layers was prepared on a cellulose triacetate film support having a subbing layer.

Composition of the Layers

In the following layers, the coating amounts of a silver halide emulsion and colloidal silver are shown by a g/m² unit of silver, the coating amounts of couplers, additives, and gelatin are shown by a g/m² unit, and the coating amounts of sensitizing dyes are shown by mol number per mol of the silver halide in the same layer. In addition, the marks showing additives are as follows.

| | |
|---|---|
| UV: | Ultraviolet absorbent |
| Solv: | High boiling point organic solvent |
| ExF: | Dye |
| ExS: | Sensitizing dye |
| ExC: | Cyan coupler |
| ExM: | Magenta coupler |
| ExY: | Yellow coupler |
| Cpd: | Additive |
| H: | Hardening agent |

First Layer: Antihalation Layer

| | |
|---|---|
| Black Colloid Silver | 0.15 |
| Gelatin | 2.9 |
| UV-1 | 0.03 |
| UV-2 | 0.06 |
| UV-3 | 0.07 |
| Solv-2 | 0.08 |
| ExF-1 | 0.01 |
| ExF-2 | 0.01 |

Second Layer: Low Speed Red-Sensitive Emulsion Layer

| | |
|---|---|
| Silver Iodobromide Emulsion (AgI: 4 mol %, uniform AgI type, sphere corresponding diameter: 0.4 μm, variation coefficient of sphere corresponding diameters: 37%, tabular grain, aspect ratio: 3.0) | 0.4 |
| Gelatin | 0.8 |
| ExS-1 | $2.3 \times 10^{-4}$ |
| ExS-2 | $1.4 \times 10^{-4}$ |
| ExS-5 | $2.3 \times 10^{-4}$ |
| ExS-7 | $8.0 \times 10^{-6}$ |
| ExC-1 | 0.17 |
| ExC-2 | 0.03 |
| ExC-3 | 0.13 |

Third Layer: Middle Speed Red-Sensitive Emulsion Layer

| | |
|---|---|
| Silver Iodobromide Emulsion (AgI: 6 mol %, inside high AgI type of core/shell ratio of 2/1, sphere corresponding diameter: 0.65 μm, variation coefficient of sphere corresponding diameters: 25%, tabular grain, aspect ratio: 2.0) | 0.65 |
| Silver Iodobromide Emulsion (AgI: 4 mol %, uniform AgI type, sphere corresponding diameter: 0.4 μm, variation coefficient of sphere corresponding diameters: 37%, tabular grain, aspect ratio: 3.0) | 0.1 |
| Gelatin | 1.0 |
| ExS-1 | $2 \times 10^{-4}$ |
| ExS-2 | $1.2 \times 10^{-4}$ |
| ExS-5 | $2 \times 10^{-4}$ |
| ExS-7 | $7 \times 10^{-6}$ |
| ExC-1 | 0.31 |
| ExC-2 | 0.01 |
| ExC-3 | 0.06 |

Fourth Layer: High Speed Red-Sensitive Emulsion Layer

| | |
|---|---|
| Silver Iodobromide Emulsion (AgI: 6 mol %, inside high AgI type of core/shell ratio of 2/1, sphere corresponding diameter: 0.7 μm, variation coefficient of sphere corresponding diameters: 25%, tabular grain, aspect ratio: 2.5) | 0.9 |
| Gelatin | 0.8 |
| ExS-1 | $1.6 \times 10^{-4}$ |
| ExS-2 | $1.6 \times 10^{-4}$ |
| ExS-5 | $1.6 \times 10^{-4}$ |
| ExS-7 | $6 \times 10^{-4}$ |
| ExC-1 | 0.07 |
| ExC-4 | 0.05 |
| Solv-1 | 0.07 |
| Solv-2 | 0.20 |
| Cpd-7 | $4.6 \times 10^{-4}$ |

Fifth Layer: Interlayer

| | |
|---|---|
| Gelatin | 0.6 |
| UV-4 | 0.03 |
| UV-5 | 0.04 |
| Cpd-1 | 0.1 |
| Polyethylene Acrylate Latex | 0.08 |
| Solv-1 | 0.05 |

Sixth Layer: Low Speed Green-Sensitive Emulsion Layer

| | |
|---|---|
| Silver Iodobromide Emulsion (AgI: 4 mol %, uniform AgI type, sphere corresponding diameter: 0.4 μm, variation coefficient of sphere corresponding diameters: 37%, tabular grain, aspect ratio: 2.0) | 0.18 |
| Gelatin | 0.4 |
| ExS-3 | $2 \times 10^{-4}$ |
| ExS-4 | $7 \times 10^{-4}$ |
| ExS-5 | $1 \times 10^{-4}$ |
| ExM-5 | 0.11 |
| ExM-7 | 0.03 |
| ExY-8 | 0.01 |
| Solv-1 | 0.09 |
| Solv-4 | 0.01 |

Seventh Layer: Middle Speed Green-Sensitive Emulsion Layer

| | |
|---|---|
| Silver Iodobromide Emulsion (AgI: 4 mol %, surface high AgI type of core/shell ratio of 1/1, sphere corresponding diameter: 0.5 μm, variation coefficient of sphere corresponding diameters: 20%, tabular grain, aspect ratio: 4.0) | 0.27 |
| Gelatin | 0.6 |
| ExS-3 | $2 \times 10^{-4}$ |
| ExS-4 | $7 \times 10^{-4}$ |
| ExS-5 | $1 \times 10^{-4}$ |
| ExM-5 | 0.17 |
| ExM-7 | 0.04 |
| ExY-8 | 0.02 |
| Solv-1 | 0.14 |
| Solv-4 | 0.02 |

Eighth Layer: High Speed Green-Sensitive Emulsion Layer

| | |
|---|---|
| Silver Iodobromide Emulsion (AgI: 8.7 mol %, multilayer structure grain of 3/4/2 in silver ratio, AgI content: 24 mol %, 0 mol %, and 3 mol % from inside, sphere corresponding diameter: 0.7 μm, variation coefficient of sphere corresponding diameters: 25%, tabular grain, aspect ratio: 1.6) | 0.7 |
| Gelatin | 0.8 |
| ExS-4 | $5.2 \times 10^{-4}$ |
| ExS-5 | $1 \times 10^{-4}$ |
| ExS-8 | $0.3 \times 10^{-4}$ |
| ExM-5 | 0.1 |
| ExM-6 | 0.03 |
| ExY-8 | 0.02 |
| ExC-1 | 0.02 |
| ExC-4 | 0.01 |
| Solv-1 | 0.25 |
| Solv-2 | 0.06 |
| Solv-4 | 0.01 |
| Cpd-7 | $1 \times 10^{-4}$ |

Ninth Layer: Interlayer

| | |
|---|---|
| Gelatin | 0.6 |
| Cpd-1 | 0.04 |
| Polyethylene Acrylate Latex | 0.12 |
| Solv-1 | 0.02 |

Tenth Layer: Donor Layer of Multilayer Effect for Red-Sensitive Emulsion Layer

| | |
|---|---|
| Silver Iodobromide Emulsion (AgI: 6 mol %, inside high AgI type of core/shell ratio of 2/1, sphere corresponding diameter: 0.7 μm, variation coefficient of sphere corresponding diameters: 25%, tabular grain, aspect ratio: 2.0) | 0.68 |
| Silver Iodobromide Emulsion (AgI: 4 mol %, uniform AgI type, sphere corresponding diameter: 0.4 μm, variation coefficient of sphere corresponding diameters: 37%, | 0.19 |

| | |
|---|---|
| tabular grain, aspect ratio: 3.0) | |
| Gelatin | 1.0 |
| ExS-3 | $6 \times 10^{-4}$ |
| ExM-10 | 0.19 |
| Solv-1 | 0.20 |
| Eleventh Layer: Yellow Filter Layer | |
| Yellow Colloid Silver | 0.06 |
| Gelatin | 0.8 |
| Cpd-2 | 0.13 |
| Solv-1 | 0.13 |
| Cpd-1 | 0.07 |
| Cpd-6 | 0.002 |
| H-1 | 0.13 |
| Twelfth Layer: Low Speed Blue-Sensitive Emulsion Layer | |
| Silver Iodobromide Emulsion (AgI: 4.5 mol %, uniform AgI type, sphere corresponding diameter: 0.7 μm, variation coefficient of sphere corresponding diameters: 15%, tabular grain, aspect ratio: 7.0) | 0.3 |
| Silver Iodobromide Emulsion (AgI: 3 mol %, uniform AgI type, sphere corresponding diameter: 0.3 μm, variation coefficient of sphere corresponding diameters: 30%, tabular grain, aspect ratio: 7.0) | 0.15 |
| Gelatin | 1.8 |
| ExS-6 | $9 \times 10^{-4}$ |
| ExC-1 | 0.06 |
| ExC-4 | 0.03 |
| ExY-9 | 0.14 |
| ExY-11 | 0.89 |
| Solv-1 | 0.42 |
| Thirteenth Layer: Interlayer | |
| Gelatin | 0.7 |
| ExY-12 | 0.20 |
| Solv-1 | 0.34 |
| Fourteenth Layer: High Speed Blue-Sensitive Emulsion Layer | |
| Silver Iodobromide Emulsion (AgI: | 0.5 |
| 10 mol %, inside high AgI type, corresponding diameter: 1.0 μm, variation coefficient of sphere corresponding diameter: 25%, multilayer twin tabular grain, aspect ratio: 2.0) | |
| Gelatin | 0.5 |
| ExS-6 | $1 \times 10^{-4}$ |
| ExY-9 | 0.01 |
| ExY-11 | 0.20 |
| ExC-1 | 0.02 |
| Solv-1 | 0.10 |
| Fifteenth Layer: First Protective Layer | |
| Fine Grain Silver Iodobromide Emulsion (AgI: 2 mol %, uniform AgI type, sphere corresponding diameter: 0.07 μm) | 0.12 |
| Gelatin | 0.9 |
| UV-4 | 0.11 |
| UV-5 | 0.16 |
| Solv-5 | 0.02 |
| H-1 | 0.13 |
| Cpd-5 | 0.10 |
| Polyethylene Acrylate Latex | 0.09 |
| Sixteenth Layer: Second Protective Layer | |
| Fine Grain Silver Iodobromide Emulsion (AgI: 2 mol %, uniform AgI type, sphere corresponding diameter: 0.07 μm) | 0.36 |
| Gelatin | 0.55 |
| Polymethyl Methacrylate Particles diameter: 1.5 μm) | 0.2 |
| H-1 | 0.17 |

In addition to the aforesaid components, a stabilizer, Cpd-3 (0.07 g/m²) for the emulsion layers and a surface active agent, Cpd-4 (0.03 g/m²) as a coating aid were added to the coating compositions for the aforesaid layers.

The compounds used above were as follows.

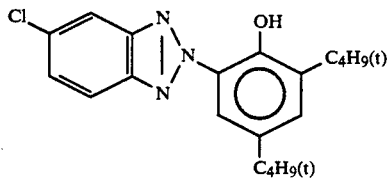

UV-1

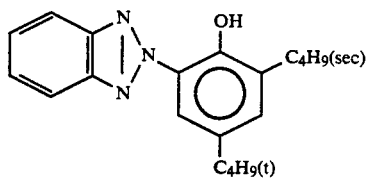

UV-2

UV-3

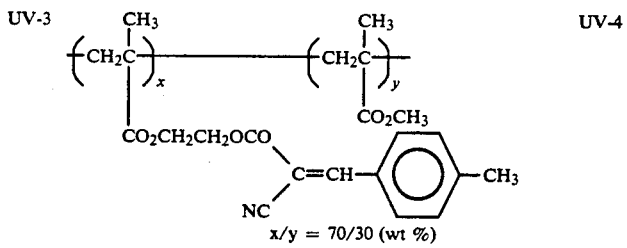

UV-4

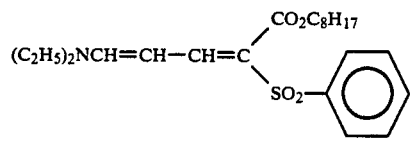

UV-5

Tricresyl phosphate

Solv-1

Dibutyl phthalate

Solv-2

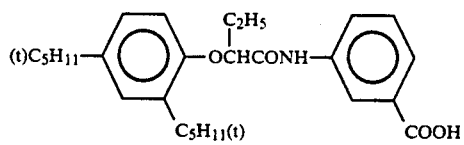

Solv-4

Trihexyl phosphate
-continued
Solv-5
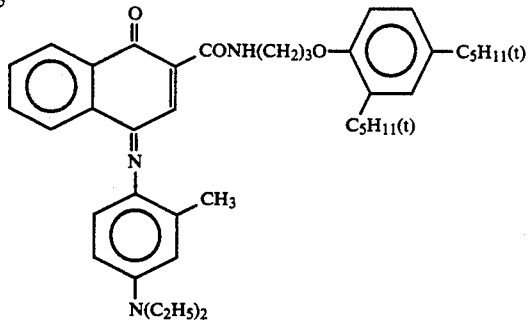
ExF-1
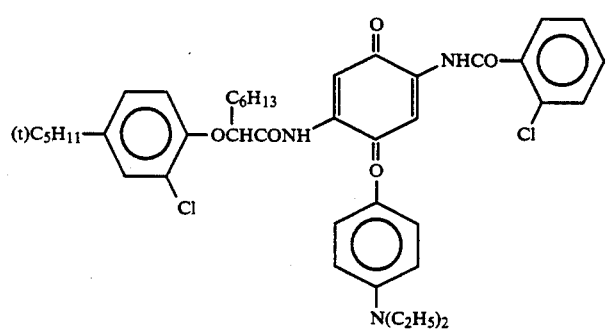
ExF-2
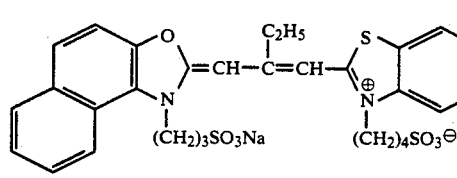
ExS-1
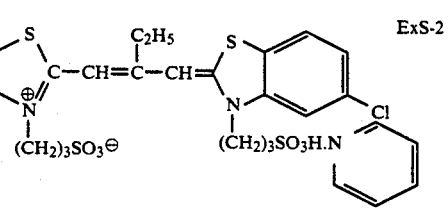
ExS-2
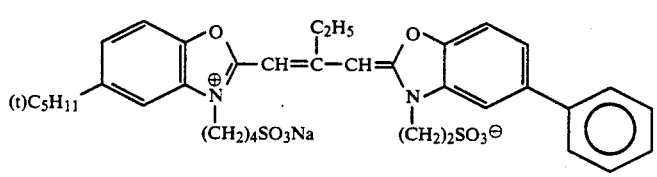
ExS-3
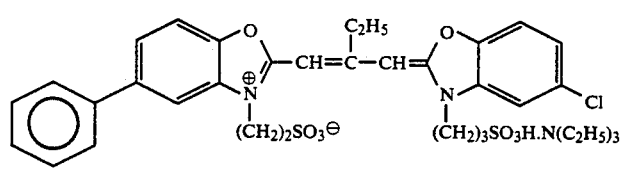
ExS-4
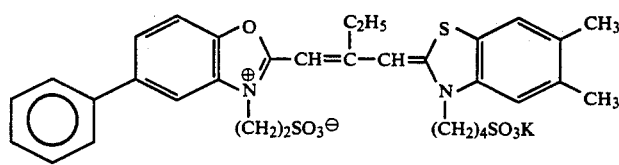
ExS-5
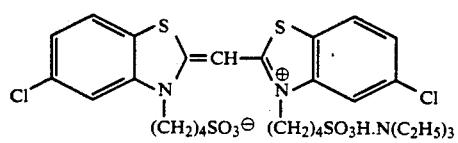
ExS-6
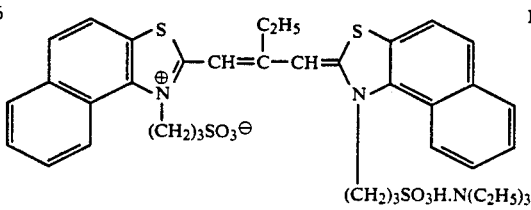
ExS-7

-continued
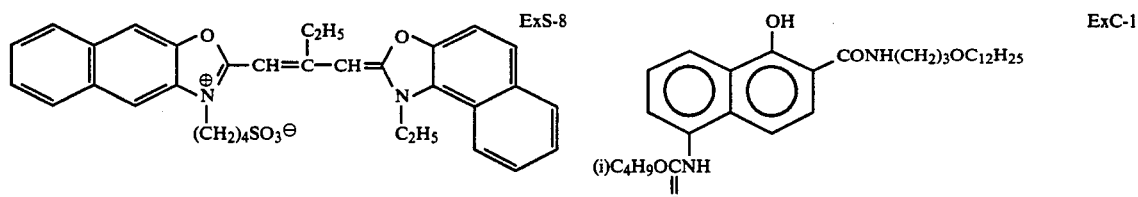
ExS-8
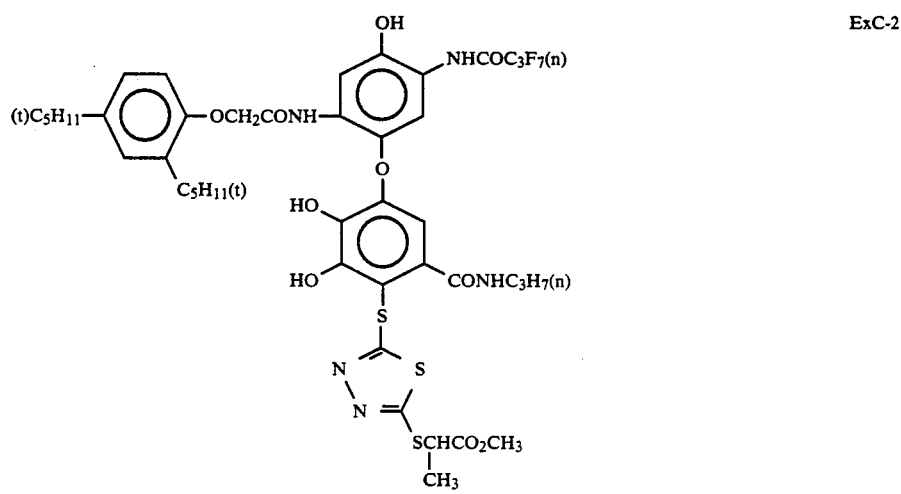
ExC-1
ExC-2
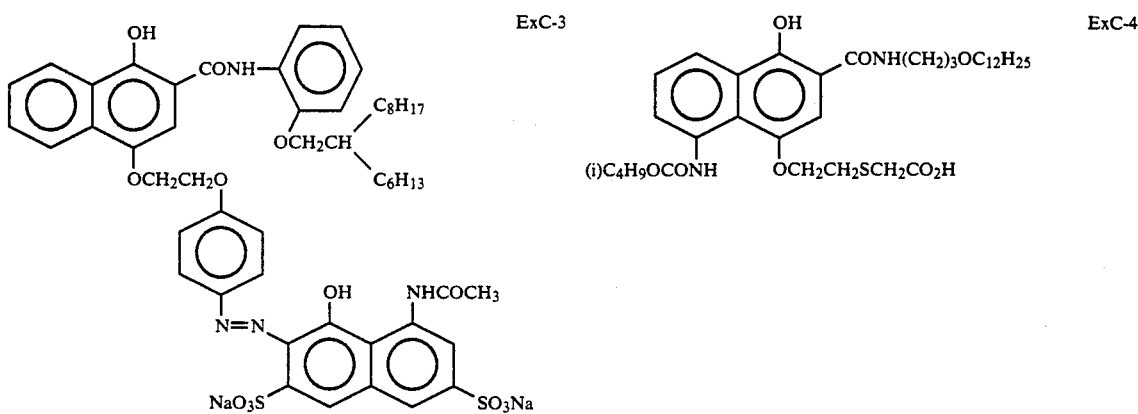
ExC-3
ExC-4
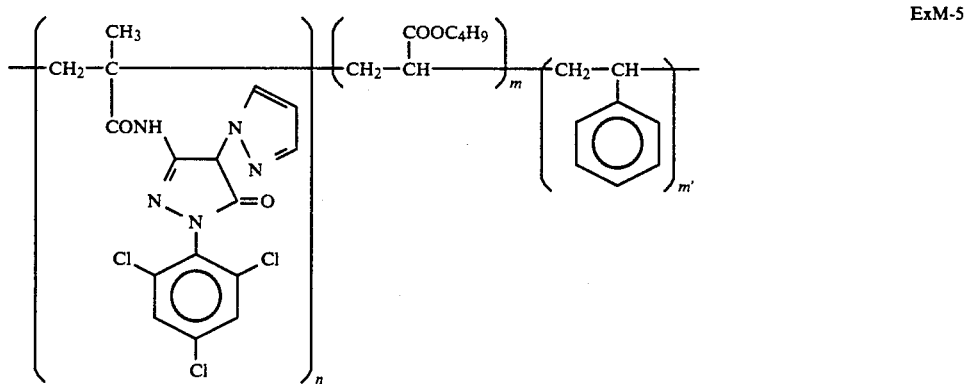
ExM-5
n = 50, m = 25, m' = 25, molecular weight = about 20,000

-continued
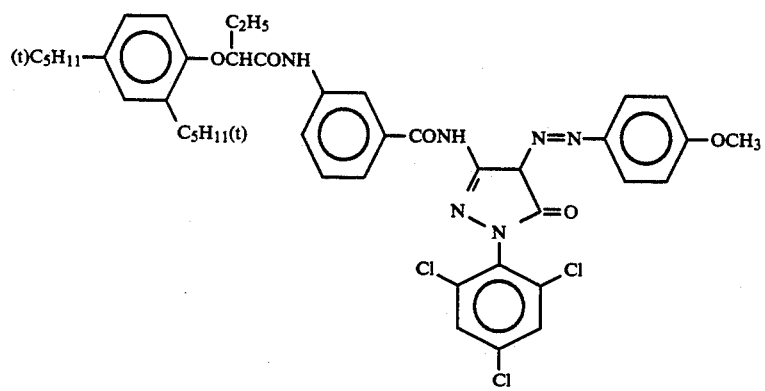
ExM-6
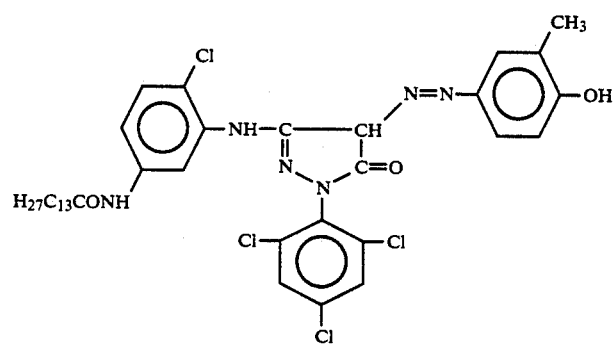
ExM-7
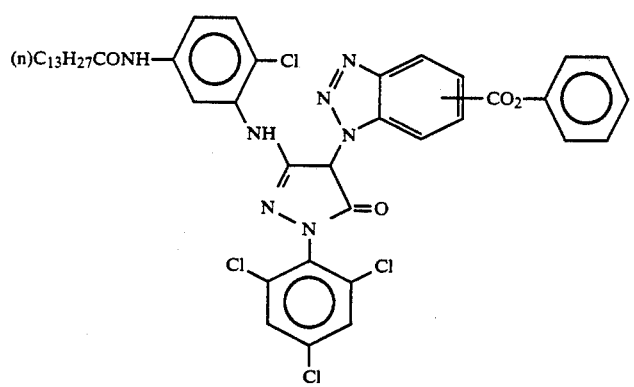
ExM-10
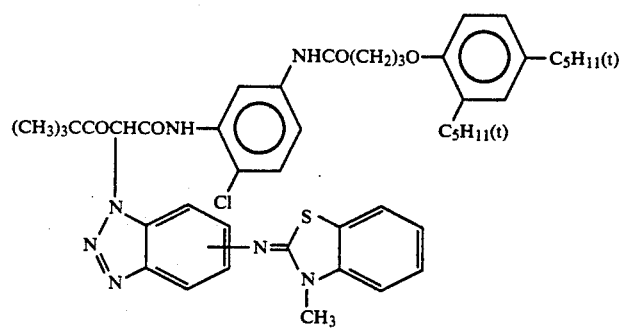
ExY-8

 ExY-9
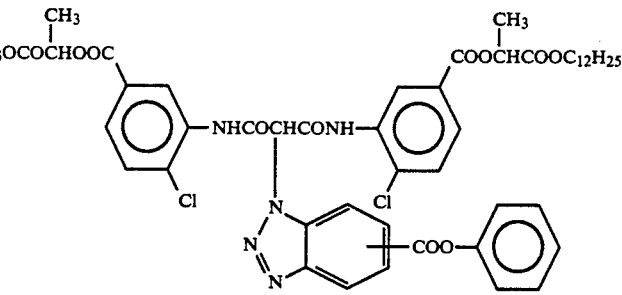 ExY-11
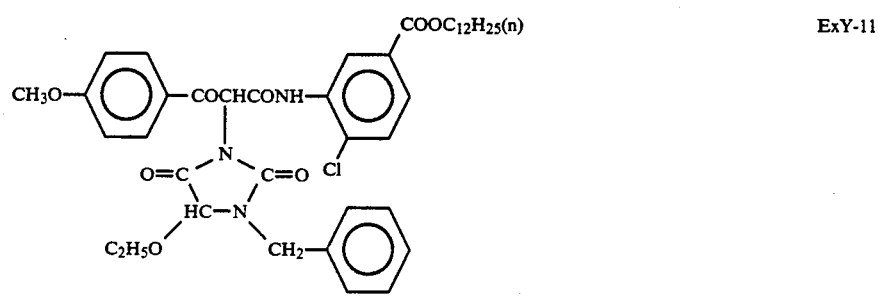 ExY-12
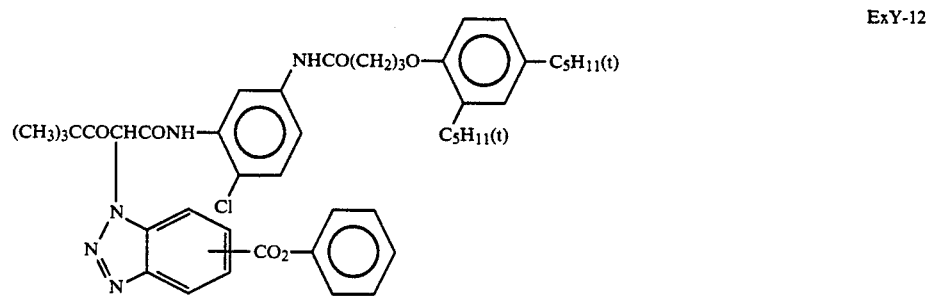
Cpd-7                     Cpd-1
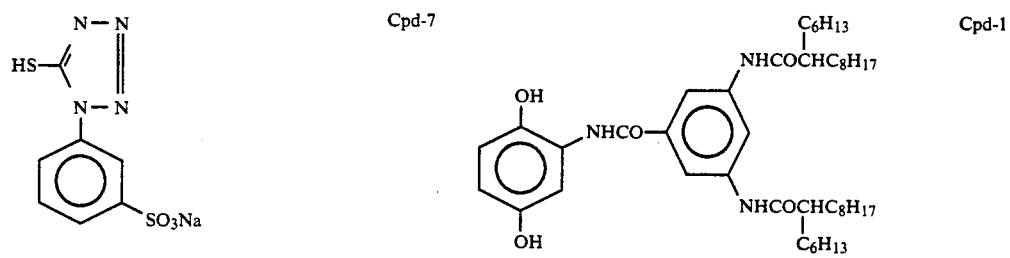 Cpd-2
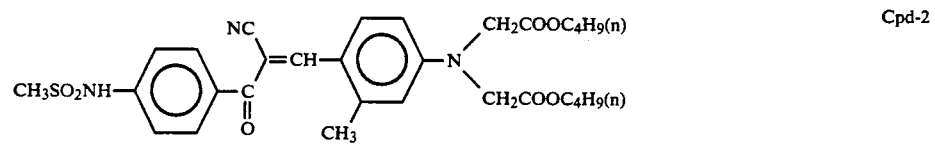
Cpd-6                     Cpd-5
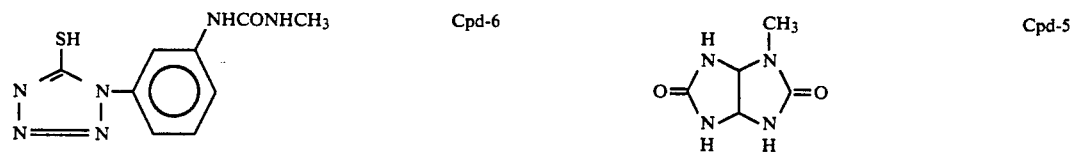
Cpd-3                     Cpd-4
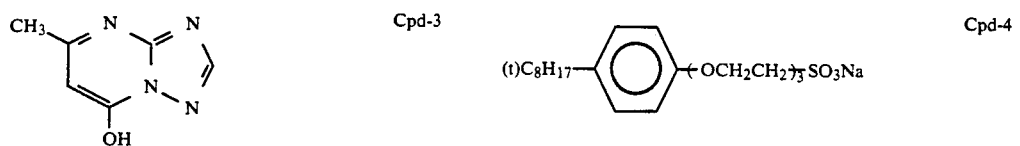

-continued

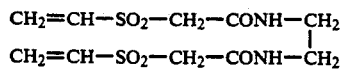    H-1

The color photographic film thus prepared was imagewise exposed by an ordinary manner.

Four such imagewise exposed samples were prepared. Each of the samples was developed by each of Developers (K) and (L) containing the color developing agents of the present invention and Developers (M) and (N) containing the following comparative color developing agents, and then bleached, fixed, and stabilized to provide four kinds of samples having color images.

| Processing Steps | Time | Temperature (°C.) |
|---|---|---|
| Color Development | 3 min 15 sec | 38 |
| Bleach | 6 min 30 sec | 38 |
| Wash | 2 min 10 sec | 24 |
| Fix | 4 min 20 sec | 38 |
| Wash (1) | 1 min 05 sec | 24 |
| Wash (2) | 1 min 00 sec | 24 |
| Stabilization | 1 min 05 sec | 38 |
| Drying | 4 min 20 sec | 55 |

The compositions of the processing solutions are shown below.

| Color Developer: | |
|---|---|
| Diethylenetriaminepentaacetic Acid | 1.0 g |
| 1-Hydroxyethylidene-1,1-diphosphonic Acid | 3.0 g |
| Sodium Sulfite | 4.0 g |
| Potassium Carbonate | 30.0 g |
| Potassium Bromide | 1.4 g |
| Potassium Iodide | 1.5 mg |
| Hydroxylamine Sulfate | 2.4 g |
| Color Developing Agent (shown below) | 15 mmols |
| Water to make | 1,000 ml |
| pH | 10.05 |
| Bleach Solution: | |
| Ethylenediaminetetraacetic Acid Ferric Sodium Trihydrate | 100.0 g |
| Ethylenediaminetetraacetic Acid Disodium Salt | 10.0 g |
| Ammonium Bromide | 140.0 g |
| Ammonium Nitrate | 30.0 g |
| Aqueous Ammonia (27 wt %) | 6.5 ml |
| Water to make | 1,000 ml |
| pH | 6.0 |
| Color Developing Agent | |
| Developer (K): | |
| The p-toluenesulfonate of Compound (1) of the present invention | |
| Developer (L): | |
| The p-toluenesulfonate of Compound (8) of the present invention | |
| Developer (M): | |
| The sulfate of N-ethyl-N-(2-hydroxyethyl)-3-methyl-4-aminoaniline | |
| Developer (N): | |
| The p-toluenesulfonate of N-ethyl-N-(2-methoxyethyl)-3-methyl-4-aminoaniline | |
| Fix Solution: | |
| Ethylenediaminetetraacetic Acid Disodium Salt | 0.5 g |
| Sodium Sulfite | 7.0 g |
| Sodium Hydrogensulfite | 5.0 g |
| Aqueous Solution of Ammonium Thiosulfate (70 wt %) | 170.0 ml |

| -continued | |
|---|---|
| Water to make | 1,000 ml |
| pH | 6.7 |
| Stabilization Solution: | |
| Formalin (37 wt %) | 2.0 ml |
| Polyoxyethylene-p-mononoylphenyl Ether (average polymerization degree: 10) | 0.3 g |
| Ethylenediaminetetraacetic Acid Sodium Salt | 0.05 g |
| Water to make | 1,000 ml |
| pH | 5.0 to 8.0 |

The maximum densities of yellow, magenta, and cyan were measured on each sample thus processed and the results are shown in Table 5 below.

TABLE 5

| Developer | Maximum Density | | |
|---|---|---|---|
|  | Yellow | Magenta | Cyan |
| (K) | 3.61 | 2.86 | 2.31 |
| (L) | 3.52 | 2.79 | 2.24 |
| (M)* | 3.11 | 2.51 | 1.96 |
| (N)* | 3.20 | 2.70 | 2.13 |

*Comparison

From the results shown in Table 5, it can be seen that the maximum densities of yellow, magenta, and cyan were very high in the samples processed using Developers (K) to (L) containing the compounds of the present invention as compared to the samples processed by Comparative Developers (M) and (N).

EXAMPLE 6

A sample was prepared by forming the following layers on a cellulose triacetate film support having a subbing layer.

| First Layer: Antihalation Layer | |
|---|---|
| Black Colloid Silver | 0.25 g/m$^2$ |
| Ultraviolet Absorbent U-1 | 0.1 g/m$^2$ |
| Ultraviolet Absorbent U-2 | 0.1 g/m$^2$ |
| High Boiling Point Organic Solvent Oil-1 | 0.1 ml/m$^2$ |
| Gelatin | 1.9 g/m$^2$ |
| Second Layer: First Interlayer | |
| Cpd-1 | 10 mg/m$^2$ |
| High Boiling Point Organic Solvent Oil-3 | 40 mg/m$^2$ |
| Gelatin | 0.4 g/m$^2$ |
| Third Layer: Second Interlayer | |
| Fogged Fine Grain Silver Iodobromide Emulsion (mean grain size: 0.06 μm, AgI content: 1 mol %) | 0.05 g/m$^2$ |
| Gelatin | 0.4 g/m$^2$ |
| Fourth Layer: First Red-Sensitive Emulsion Layer | |
| Silver Iodobromide Emulsion EM-1 Spectrally Sensitized by Sensitizing Dyes S-1 and S-2 | 0.4 g/m$^2$ as Ag |
| Coupler C-1 | 0.2 g/m$^2$ |
| Coupler C-2 | 0.05 g/m$^2$ |
| High Boiling Point Organic Solvent Oil-2 | 0.1 ml/m$^2$ |
| Gelatin | 0.8 g/m$^2$ |
| Fifth Layer: Second Red-Sensitive Emulsion Layer | |
| Silver Iodobromide Emulsion EM-4 | 0.4 g/m$^2$ as Ag |

Spectrally Sensitized by Sensitizing
Dyes S-1 and S-2
| | |
|---|---|
| Coupler C-1 | 0.2 g/m² |
| Coupler C-3 | 0.2 g/m² |
| Coupler C-2 | 0.05 g/m² |
| High Boiling Point Organic Solvent Oil-1 | 0.1 ml/m² |
| Gelatin | 0.8 g/m² |

Sixth Layer: Third Red-Sensitive Emulsion Layer

| | |
|---|---|
| Silver Iodobromide Emulsion EM-7 | 0.4 g/m² as Ag |

Spectrally Sensitized by Sensitizing
Dyes S-1 and S-2

| | |
|---|---|
| Coupler C-3 | 0.7 g/m² |
| Coupler C-1 | 0.3 g/m |
| Gelatin | 1.1 g/m² |

Seventh Layer: Third Interlayer

| | |
|---|---|
| Dye D-1 | 0.02 g/m² |
| Gelatin | 0.6 g/m² |

Eighth Layer: Fourth Interlayer

| | |
|---|---|
| Fogged Silver Iodobromide Emulsion (mean grain size: 0.06 μm, AgI content: 0.3 mol %) | 0.2 g/m² |
| Compound Cpd-A | 0.2 g/m² |
| Gelatin | 1.0 g/m² |

Ninth Layer: First Green-Sensitive Emulsion Layer

| | |
|---|---|
| Silver Iodobromide Emulsion EM-1 | 0.5 g/m² as Ag |

Spectrally Sensitized by Sensitizing
Dyes S-3 and S-4

| | |
|---|---|
| Coupler C-4 | 0.10 g/m² |
| Coupler C-7 | 0.10 g/m² |
| Coupler C-8 | 0.10 g/m² |
| Compound Cpd-B | 0.03 g/m² |
| Compound Cpd-E | 0.1 g/m² |
| Compound Cpd-F | 0.1 g/m² |
| Compound Cpd-G | 0.05 g/m² |
| Compound Cpd-H | 0.05 g/m² |
| Gelatin | 0.5 g/m² |
| High Boiling Point Organic Solvent Oil-1 | 0.1 g/m² |

Tenth Layer: Second Green-Sensitive Emulsion Layer

| | |
|---|---|
| Silver Iodobromide Emulsion EM-4 | 0.4 g/m² as Ag |

Spectrally Sensitized by Sensitizing
Dyes S-3 and S-4

| | |
|---|---|
| Coupler C-4 | 0.10 g/m² |
| Coupler C-7 | 0.10 g/m² |
| Coupler C-8 | 0.10 g/m² |
| Compound Cpd-B | 0.03 g/m² |
| Compound Cpd-E | 0.1 g/m² |
| Compound Cpd-F | 0.1 g/m² |
| Compound Cpd-G | 0.05 g/m² |
| Compound Cpd-H | 0.05 g/m² |
| Gelatin | 0.6 g/m² |
| High Boiling Point Organic Solvent Oil-2 | 0.01 g/m² |

Eleventh Layer: Third Green-Sensitive Emulsion Layer

| | |
|---|---|
| Silver Iodobromide Emulsion EM-7 | 0.5 g/m² as Ag |

Spectrally Sensitized by Sensitizing
Dyes S-3 and S-4

| | |
|---|---|
| Coupler C-4 | 0.4 g/m² |
| Coupler C-7 | 0.2 g/m² |
| Coupler C-8 | 0.2 g/m² |
| Compound Cpd-B | 0.08 g/m² |
| Compound Cpd-E | 0.1 g/m² |
| Compound Cpd-F | 0.1 g/m² |
| Compound Cpd-G | 0.1 g/m² |
| Compound Cpd-H | 0.1 g/m² |
| Gelatin | 1.0 g/m² |
| High Boiling Point Organic Solvent Oil-1 | 0.02 g/m² |
| High Boiling Point Organic Solvent Oil-2 | 0.02 g/m² |

Twelfth Layer: Fifth Interlayer

| | |
|---|---|
| Dye D-2 | 0.05 g/m² |
| Gelatin | 0.6 g/m² |

Thirteenth Layer: Yellow Filter Layer

| | |
|---|---|
| Yellow Colloid Silver | 0.1 g/m² |
| Compound Cpd-A | 0.01 g/m² |
| Gelatin | 1.1 g/m² |

Fourteenth Layer: First Blue-Sensitive Emulsion Layer

| | |
|---|---|
| Silver Iodobromide Emulsion EM-1 | 0.6 g/m² as Ag |

Spectrally Sensitized by Sensitizing
Dyes S-5 and S-6

| | |
|---|---|
| Coupler C-5 | 0.6 g/m² |
| Gelatin | 0.8 g/m² |
| High Boiling Point Organic Solvent Oil-1 | 0.01 g/m² |

Fifteenth Layer: Second Blue-Sensitive Emulsion Layer

| | |
|---|---|
| Silver Iodobromide Emulsion EM-4 | 0.4 g/m² as Ag |

Spectrally Sensitized by Sensitizing
Dyes S-5 and S-6

| | |
|---|---|
| Coupler C-5 | 0.3 g/m² |
| Coupler C-6 | 0.3 g/m² |
| Gelatin | 0.9 g/m² |

Sixteenth Layer: Third Blue-Sensitive Emulsion Layer

| | |
|---|---|
| Silver Iodobromide Emulsion EM-7 | 0.4 g/m² as Ag |

Spectrally Sensitized by Sensitizing
Dyes S-5 and S-6

| | |
|---|---|
| Coupler C-6 | 0.7 g/m² |
| Gelatin | 1.2 g/m² |

Seventeenth Layer: First Protective Layer

| | |
|---|---|
| Ultraviolet Absorbent U-1 | 0.04 g/m² |
| Ultraviolet Absorbent U-3 | 0.03 g/m² |
| Ultraviolet Absorbent U-4 | 0.03 g/m² |
| Ultraviolet Absorbent U-5 | 0.05 g/m² |
| Ultraviolet Absorbent U-6 | 0.05 g/m² |
| Compound Cpd-C | 0.8 g/m² |
| Dye D-3 | 0.05 g/m² |
| Gelatin | 0.7 g/m² |

Eighteenth Layer: Second Protective Layer

| | |
|---|---|
| Fogged Silver Iodobromide Emulsion (mean grain size: 0.06 μm, AgI content: 1 mol %) | 0.1 g/m² as Ag |
| Gelatin | 0.4 g/m² |
| High Boiling Point Organic Solvent Oil-1 | 0.02 g/m² |

Nineteenth Layer: Third Protective Layer

| | |
|---|---|
| Polymethyl Methacrylate (mean grain size: 1.5 μm) | 0.1 g/m² |
| Copolymer of Methyl Methacrylate and Acrylic Acid at 4/6 (average particle size: 1.5 μm) | 0.1 g/m² |
| Silicone Oil | 0.03 g/m² |
| Fluorine-Containing Surface Active Agent W-1 | 3 g/m² |
| Gelatin | 0.4 g/m² |

To each layer were further added Gelatin Hardening Agent H-1 and a surface active agent.

Emulsions EM-1, EM-4 and EM-7 described above are shown below.

Silver Iodobromide Emulsion EM-1:
AgI content: 3.5 mol %
Average grain diameter: 0.25 μm
Variation coefficient of sphere corresponding diameter: 15%
Monodispersed tetradecahedral grain emulsion Silver Iodobromide Emulsion EM-4:
AgI content: 4.0 mol %
Average grain diameter: 0.30 μm
Variation coefficient of sphere corresponding diameter: 13%
Monodispersed cubic grain emulsion Silver Iodobromide Emulsion EM-7:
AgI content: 1.5 mol %
Average grain diameter: 0.80 μm
Variation coefficient of sphere corresponding diameter: 28%
Polydispersed tabular grain emulsion The compounds used for the aforesaid color photographic film were as follows.

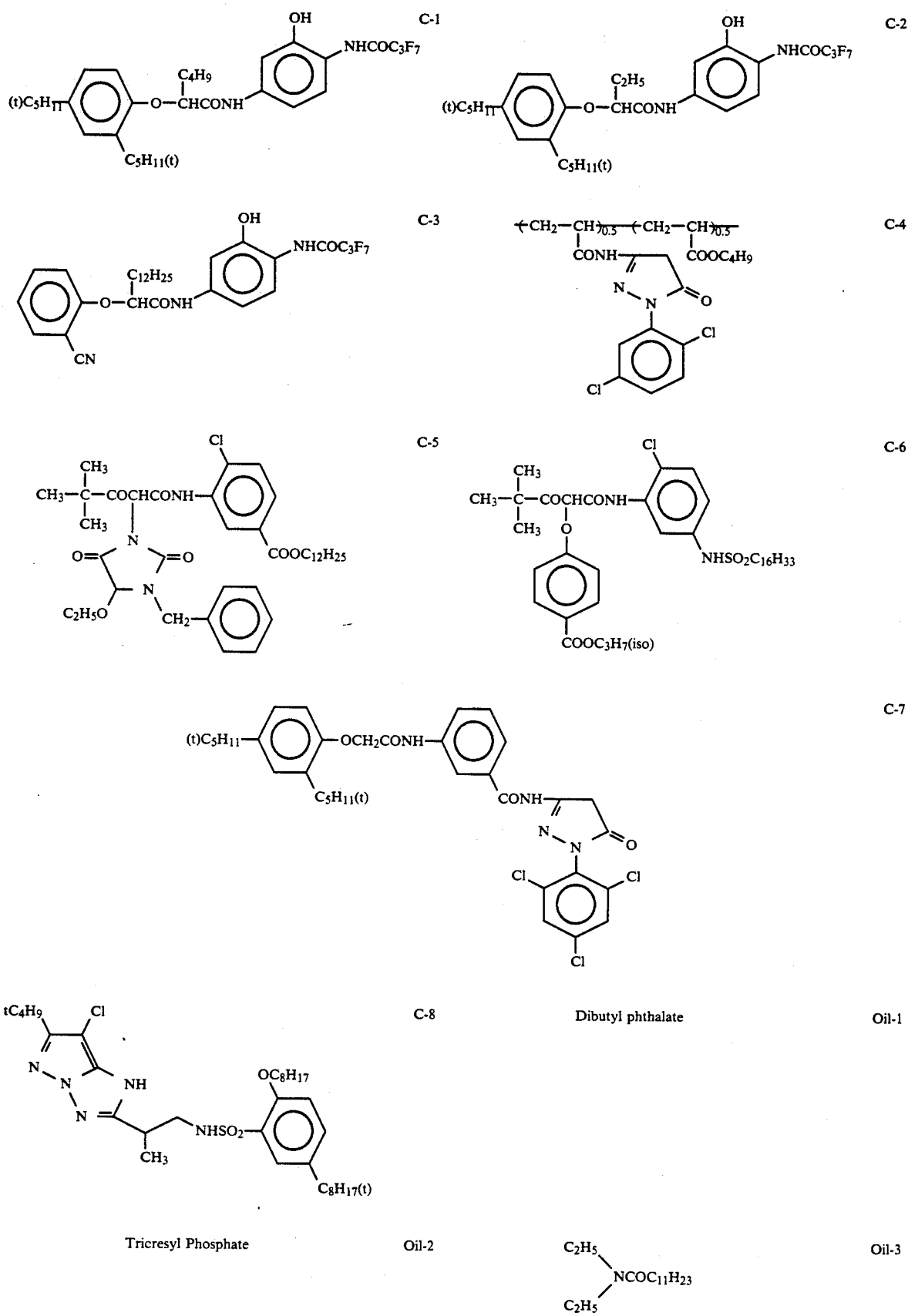

-continued
Cpd-A 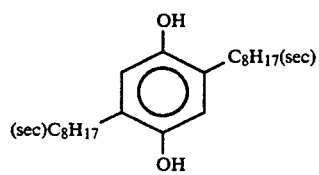
Cpd-B 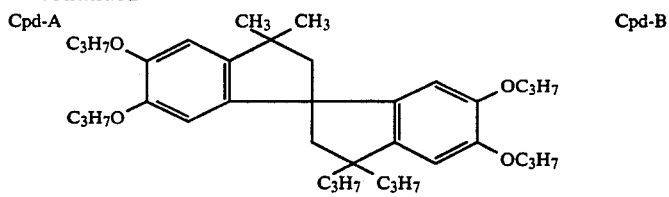
Cpd-C 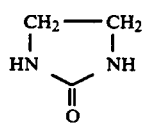
Cpd E 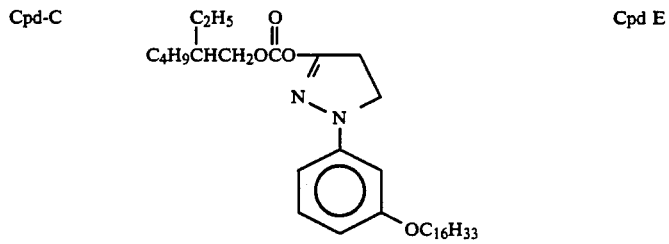
Cpd F 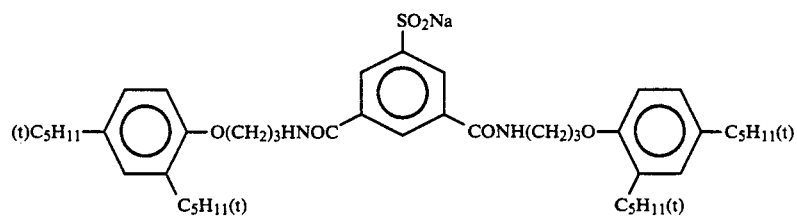
Cpd G 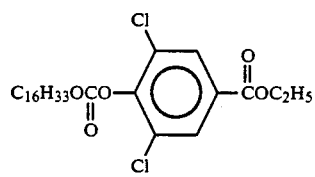
Cpd H 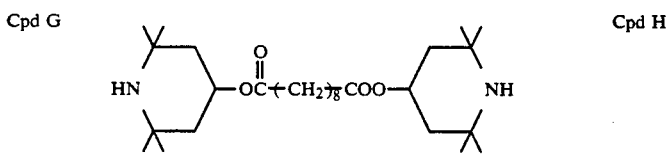
Cpd-D 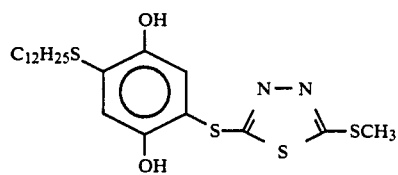
U-1 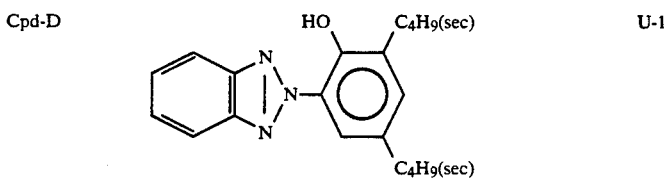
U-2 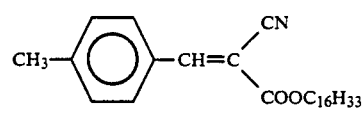
U-3 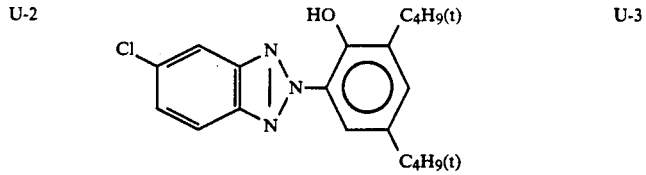
U-4 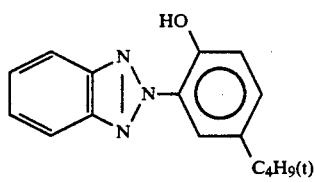
U-5 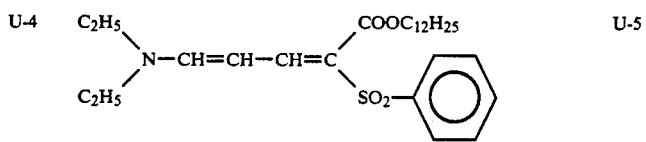
U-6 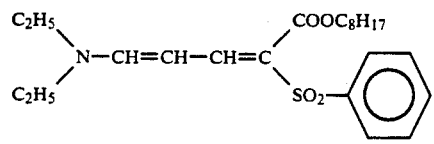
S-1 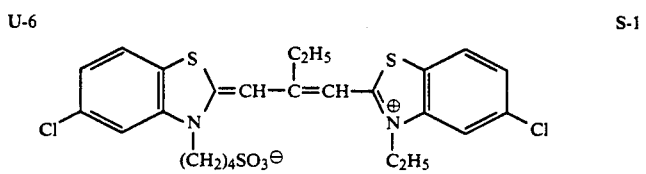

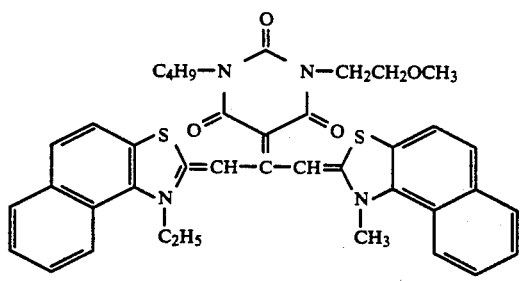  S-2

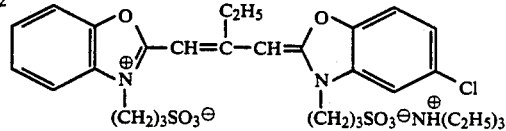  S-3

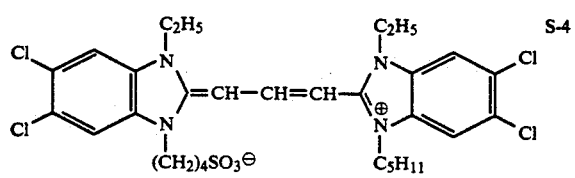  S-4

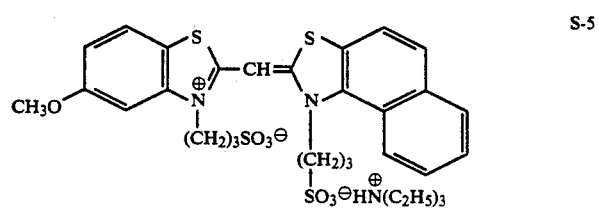  S-5

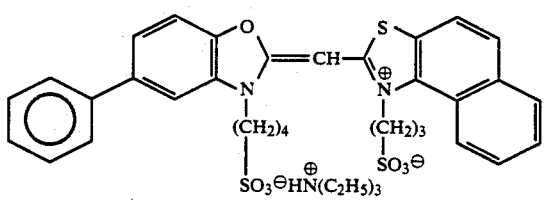  S-6

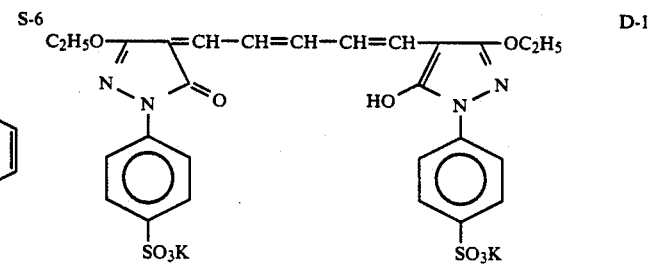  D-1

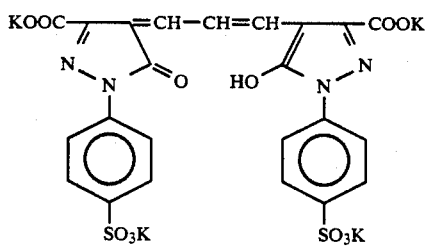  D-2

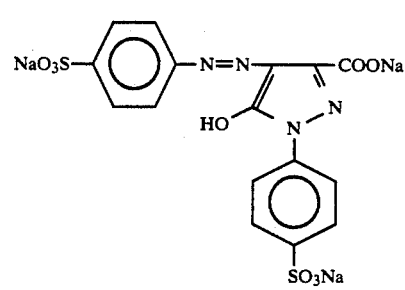  D-3

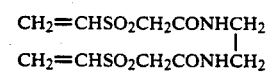  H-1

$CH_2=CHSO_2CH_2CONHCH_2$
$CH_2=CHSO_2CH_2CONHCH_2$

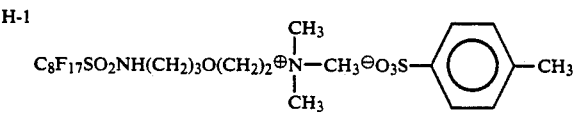  W-1

$C_8F_{17}SO_2NH(CH_2)_3O(CH_2)_2 \overset{\oplus}{N}(CH_3)_3 \cdot {}^{\ominus}O_3S$—⟨phenyl⟩—$CH_3$ The silver halide color photographic films thus prepared were imagewise exposed and processed by the following steps. In the color development step, each of the samples was processed by each of Developers (O) and (P) containing the color developing agent precursors of the present invention and Developers (Q) and (R) containing the following comparative color developing agent precursors.

Thus, four kinds of samples having color images were prepared.

| Processing Step | Time (min) | Temperature (°C.) |
|---|---|---|
| First Development | 6 | 38 |
| Wash | 2 | " |
| Reversal | 2 | " |
| Color Development | 6 | " |
| Control | 2 | " |
| Bleach | 6 | " |
| Fix | 4 | " |
| Wash | 4 | " |
| Stabilization | 1 | Normal Temperature (20° C.–35° C.) |
| Drying | | |

The compositions of the processing solutions used for the aforesaid processing steps were as follows.

| First Developer: | |
|---|---|
| Water | 700 ml |
| Nitrilo-N,N,N-trimethylenephosphonic Acid.Pentasodium Salt | 2 g |
| Sodium Sulfite | 20 g |
| Hydroquinone Monosulfonate | 30 g |
| Sodium Carbonate (monohydrate) | 30 g |
| 1-Phenyl-4-methyl-4-hydroxymethyl-3- | 2 g |

-continued

| | | |
|---|---|---|
| pyrazolidone | | |
| Potassium Bromide | 2.5 | g |
| Potassium Thiocyanate | 1.2 | g |
| Potassium Iodide (0.1 wt % solution) | 2 | ml |
| Water to make | 1,000 | ml |

Reversal Solution:

| | | |
|---|---|---|
| Water | 700 | ml |
| Nitrilo-N,N,N-trimethylenephosphonic Acid.Pentasodium Salt | 3 | g |
| Stannous Chloride (dihydrate) | 1 | g |
| p-Aminophenol | 0.1 | g |
| Sodium Hydroxide | 8 | g |
| Glacial Acetic Acid | 15 | ml |
| Water to make | 1,000 | ml |

Color Developer:

| | | |
|---|---|---|
| Water | 700 | ml |
| Nitrilo-N,N,N-trimethylenephosphonic Acid.Pentasodium Salt | 3 | g |
| Sodium Sulfite | 7 | g |
| Sodium Tertiary Phosphate (12H$_2$O) | 36 | g |
| Potassium Bromide | 1 | g |
| Potassium Iodide (0.1 wt % aq. soln.) | 90 | ml |
| Sodium Hydroxide | 3 | g |
| Color Developing Agent (shown below) | 30 | mmol |
| Citrazinic Acid | 1.5 | g |
| 3,6-Dithiaoctane-1,8-diol | 1 | g |
| Water to make | 1,000 | ml |

Color Developing Agent

Developer (O):
  The p-toluenesulfonate of Compound (1) of the present invention
Developer (P):
  The p-toluenesulfonate of Compound (8) of the present invention
Developer (Q):
  The sulfate of N-ethyl-N-[2-(methylsulfonamido)-ethyl]-3-methyl-4-aminoaniline
Developer (R):
  The p-toluenesulfonate of N-ethyl-N-(2-methoxyethyl)-3-methyl-4-aminoaniline Control Solution:

| | | |
|---|---|---|
| Water | 700 | ml |
| Sodium Sulfite | 12 | g |
| Ethylenediaminetetraacetic Acid Sodium (dihydrate) | 8 | g |
| Thioglycerol | 0.4 | ml |
| Glacial Acetic Acid | 3 | ml |
| Water to make | 1,000 | ml |

Bleach Solution:

| | | |
|---|---|---|
| Water | 800 | ml |
| Ethylenediaminetetraacetic Acid Sodium (dihydrate) | 2 | g |
| Ethylenediaminetetraacetic Acid Iron (III) Ammonium (dihydrate) | 120 | g |
| Potassium Bromide | 100 | g |
| Water to make | 1,000 | ml |

Fix Solution:

| | | |
|---|---|---|
| Water | 800 | ml |
| Sodium Thiosulfate | 80.0 | g |
| Sodium Sulfite | 5.0 | g |
| Sodium Hydrogensulfite | 5.0 | g |
| Water to make | 1,000 | ml |

Stabilization Solution:

| | | |
|---|---|---|
| Water | 800 | ml |
| Formalin (37 wt %) | 5.0 | ml |
| Fuji Driwel (trade name of a surface active agent, made by Fuji Photo film Co., Ltd.) | 5.0 | ml |
| Water to make | 1,000 | ml |

The maximum densities of yellow, magenta, and cyan were measured on each sample and the results obtained are shown in Table 6 below.

TABLE 6

| Developer | Maximum Density | | |
|---|---|---|---|
| | Yellow | Magenta | Cyan |
| (O) | 3.64 | 3.87 | 3.95 |
| (P) | 3.60 | 3.86 | 3.88 |
| (Q)* | 3.06 | 3.13 | 3.21 |
| (R)* | 3.18 | 3.16 | 3.24 |

*Comparison

From the results shown in Table 6, it can be seen that the maximum densities of yellow, magenta, and cyan are very high in the samples processed using Developers (O) and (P) containing the color developing agent of the present invention as compared to the samples processed by Comparative Developers (Q) and (R).

EXAMPLE 7

A color photographic paper was prepared by coating a silver bromide emulsion layer containing a yellow coupler emulsified dispersion, a silver chlorobromide emulsion layer (silver chloride content: 70 mol%) containing a magenta coupler emulsified dispersion, a silver chlorobromide emulsion layer (silver chloride content: 70 mol%) containing a cyan coupler emulsified dispersion, a precursor-containing layer, and a gelatin layer containing an ultraviolet absorbent in this order on a paper support coated with polyethylene.

Each coupler emulsion used for the color photographic paper was prepared by dissolving each coupler in a mixture of dibutyl phthalate and tricresyl phosphate and dispersing by emulsification the solution in an aqueous gelatin solution using sorbitan monolaurate and sodium dodecylbenzenesulfonate as emulsifying dispersants according to an ordinary an oil-in-water type emulsifying dispersion method.

As the cyan coupler, 2-[α-(2,4-di-t-amylphenoxy)-butanamido]-4,6-dichloro-5-methylphenol was used, as the magenta coupler, 1-(2,4,6-trichlorophenyl)-3-(2-chloro-5-tetradecanamido)anilino-2-pyrazolin-5-one, and as the yellow coupler, α-pivaloyl-α-(2,4-dioxo-5,5-dimethyloxazolidin-3-yl)-2-chloro-5-[α-(2,4-di-t-amylphenoxy)butane]amido. Further, the color developing agent precursors shown below were used. Also, as the ultraviolet absorbent, Compound 5 (0.5 g/m$^2$) described in JP-B-45-9586 was used. Furthermore, 2,4-dichloro-6-hydroxy-1,3,5-triazine sodium salt was used for each layer as a hardening agent at 0.4 g per 1,000 g of gelatin.

The coating amounts of the coupler and the silver salt in each emulsion layer of the color photographic paper were as follows.

| | Coating Amount of Coupler (g/m$^2$) | Coating Amount of Silver Salt (Ag-g/m$^2$) |
|---|---|---|
| Red-Sensitive Layer | 0.4 | 0.30 |
| Green-Sensitive Layer | 0.4 | 0.45 |
| Blue-Sensitive Layer | 0.5 | 0.40 |

The color developing agent precursors used for the samples were as follows.

Sample (S): Compound (56) of the present invention

Sample (T): Comparative sample

-continued

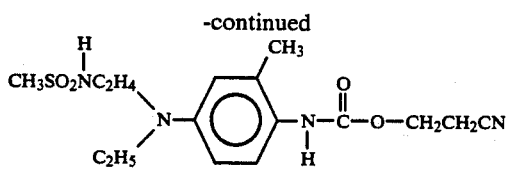

The layer containing each color developing agent precursor is formed by coating the emulsified dispersion such that the amount of each precursor became an equimolar amount to the total silver amount on the same area. The emulsified dispersion was prepared as follows.

Emulsified Dispersion

In 5 ml of a mixture of dibutyl phthalate and tricresyl phosphate was dissolved 3 g of each precursor and the solution was dispersed by emulsification in 30 ml of an aqueous 15% gelatin solution containing 10 ml of an aqueous solution of 5% sodium dodecylbenzenesulfonate.

The color photographic papers were exposed by a sensitometer (1 second, 500 CMS) and processed as follows.

| Processing Step | Temperature | Time |
|---|---|---|
| Development by Activator Bath | 50° C. | 1 min |
| Blix | " | 90 sec |
| Wash | " | 2 min |
| Stabilization | " | 1 min |

The composition of the processing solutions were as follows:

| Activator Solution: | |
|---|---|
| Benzyl Alcohol | 14 ml |
| Sodium Sulfite | 2 g |
| Potassium Bromide | 0.5 g |
| Sodium Carbonate (monohydrate) | 30 g |
| Water to make | 1,000 ml |
| pH | 11.0 |
| (The pH was adjusted by sodium hydroxide or diluted sulfuric acid.) | |
| Blix Solution: | |
| Ammonium Thiosulfate (70 wt %) | 150 ml |
| Sodium Sulfite | 5 g |
| Na[Fe (III) (EDTA)] | 40 g |
| EDTA | 4 g |
| Water to make | 1,000 ml |
| (EDTA: Ethylenediaminetetraacetic acid) | |
| Stabilization Solution: | |
| Glacial Acetic Acid | 10 ml |
| Sodium Acetate | 5 g |
| Formalin (37 wt %) | 5 ml |
| Water to make | 1,000 ml |

The results obtained are shown in Table 7.

TABLE 7

| Sample | Yellow Dmax | Magenta Dmax | Cyan Dmax |
|---|---|---|---|
| (S) | 1.25 | 1.30 | 0.90 |
| (T) | 1.15 | 1.25 | 0.75 |

Sample (S): Sample of the present invention
Sample (T): Comparative sample

As is apparent from the above results, it can be seen that the maximum densities (Dmax) of yellow, magenta and cyan are high in Sample (S) using the color developing precursor of the present invention as compared with Comparative Sample (T):

EXAMPLE 8

In the example, a core/shell type silver iodobromide emulsion, an organic silver salt dispersion, a dye providing material dispersion, and a reducing agent dispersion were prepared and heat developable light-sensitive materials (Sample No.(U) and Sample No. (V)) were prepared by using these compositions. Also, in this application, the present invention was also applied for a transfer type heat developable light-sensitive material and thus an image receiving member for such a light-sensitive material was formed as explained below.

(1) Preparation of CoreShell Type Silver Iodobromide Emulsion

A core/shell type Emulsion Em-1 having a silver iodobromide content of 1 mol% and a mean grain size of 0.3 μm was prepared by the following method.

To 1,000 ml of Aqueous Solution (A) having dissolved therein 20 g of ossein gelatin, 0.2 mol of ammonia, and 0.0385 mol of a silver iodobromide seed emulsion (mean grain size: 0.1 μm, silver iodide content: 2 mol%) were simultaneously added Aqueous Solution (B-1) containing 0.04 mol/liter of potassium iodide and 1.94 mol/liter of potassium bromide and 500 ml of Aqueous Solution (C) containing 1 mol of silver nitrate and 2 mols of ammonia at the allowable maximum speeds of not forming small grains during the addition while keeping a constant pAg using a mixing stirrer described in JP-A-57-92523 and JP-A-57-92524 to prepare core portions. It was confirmed that the emulsion was in a state of a monodispersed emulsion in this stage. After finishing the addition of Solution (B-1), Aqueous Solution (B-2) containing 1.98 mol/liter of potassium bromide was added to the emulsion together with Solution (C) to form a shell. The pH of the system during the addition thereof was kept at 9.0 and the pAg at 9.8. The pH and pAg were controlled with an aqueous 50% acetic acid solution and an aqueous solution of 25% potassium bromide, respectively. Thus, a core/shell type Silver Halide Emulsion Em-1 having a grain of regular octahedron, a mean grain size of 0.3 μm, a grain size distribution of 13%, a silver iodide content of 2 mol% in the core portion, 0 mol% in the shell portion, and 1 mol% in the total average, and a shell thickness of 0.031 μm was prepared.

Emulsion Em-1 was washed and desalted, and after adding thereto an aqueous solution of ossein gelatin (30 g of gelatin) and dispersing the emulsion in the solution, the volume of the mixture was adjusted to 800 ml with distilled water.

(2) Preparation of Organic Silver Salt Dispersion-1:

After dispersing 28.8 g of 5-methylbenzotriazole silver obtained by reacting 5-methylbenzotriazole and silver nitrate in a mixture of water and alcohol, 16.0 g of poly(N-vinylpyrrolidone), and 1.33 g of 4-sulfobenzotriazole sodium salt by an alumina ball mill, the pH and the volume of the dispersion were adjusted to 5.5 and 200 ml, respectively.

(3) Preparation of Liqht-Sensitive Silver Halide Dispersion

By applying a chemical sensitization and a spectral sensitization to each Silver Halide Emulsion Em-1 prepared as above using the following sensitizers, each of red-snsitive, green-sensitive and blue-sensitive silver halide emulsion dispersions was prepared.

(a) Preparation of Red-Sensitive Silver Iodobromide Emulsion:

The aforesaid Silver Halide Emulsion Em-1 (200 ml) was mixed with the following components:

| | |
|---|---|
| Sodium Thiosulfate | 3.0 mg |
| Chloroauric Acid | 0.4 mg |
| Ammonium Thiocyanate | 10 mg |
| Methanol Solution of 1 wt % Sensitizing Dye (a) Shown Below: | 12 ml |

Sensitizing Dye (a):

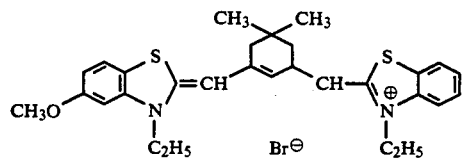

(b) Preparation of Green-Sensitive Silver Iodobromide Emulsion:

The aforesaid Silver Halide Emulsion Em-1 (200 ml) was mixed with the following components:

| | |
|---|---|
| Sodium Thiosulfate | 4.0 mg |
| Chloroauric Acid | 0.4 mg |
| Ammonium Thiocyanate | 10 mg |
| Methanol Solution of 1 wt % Sensitizing Dye (b) Shown Below | 12 ml |

Sensitizing Dye (b):

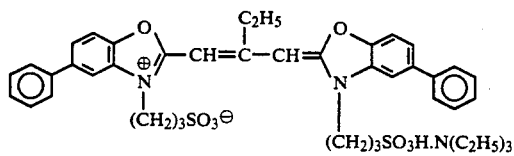

(c) Preparation of Blue-Sensitive Silver Iodobromide Emulsion:

The aforesaid Silver Halide Emulsion Em-1 (200 ml) was mixed with the following components:

| | |
|---|---|
| Sodium Thiosulfate | 3.0 mg |
| Chloroauric Acid | 0.4 mg |
| Ammonium Thiocyanate | 10 mg |
| Methanol Solution of 1 wt % Sensitizing Dye (c) Shown Below | 12 ml |

Sensitizing Dye (c):

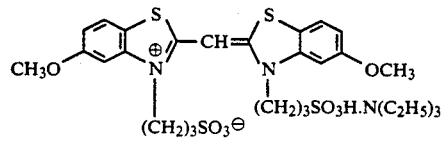

(4) Preparation of Dye Providing Material Dispersion-1

In 200 ml of ethyl acetate were dissolved 83 g of the following Dye Providing Material (1), 5.0 g of the following hydroquinone compound, and 0.5 g of the following antifoggant and the solution was mixed with 124 ml of a 5 wt % aqueous solution of Alkanol XC (trade name, made by E.I. Du Pont de Nemours & Co.) and 720 ml of an aqueous gelatin solution containing 30.5 g of phenylcarbamoylated gelatin (Type 17819PC, trade name, made by ROUSSELOT Co.). The mixture wa dispersed using an ultrasonic homogenizer and after distilling off ethyl acetate, the pH and the volume of the mixture were adjusted to 5.5 and 795 ml, respectively.

Dye Providing Material (1) (yellow dye providing material)

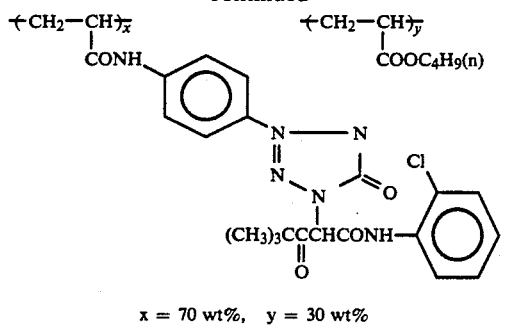

$x = 70$ wt%, $y = 30$ wt%

Hydroquinone Compound

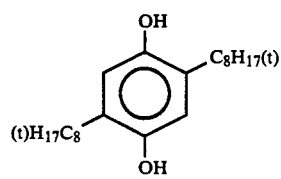

Antifoggant

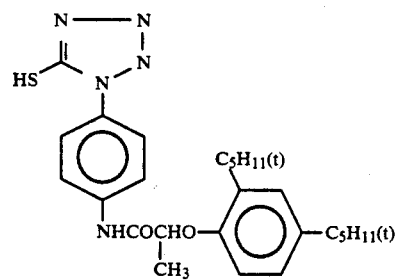

(5) Preparation of Developing Agent Dispersions U and V

After dissolving 70 mmols of each color developing agent shown below, 1.10 g of the development accelerator shown below, 14.6 g of poly(n-vinylpyrrolidone), and 0.50 g of the fluorine series surface active agent shown below in water, the pH and the volume of the solution were adjusted to 5.5 and 250 ml, respectively, to provide Developing Agent Dispersions U and V.

Development Accelerator

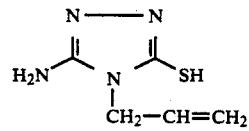

Color Developing Agent

Dispersion U:

Compound (46) of the present invention

Comparative Dispersion V:

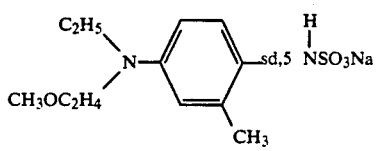

Surface Active Agent

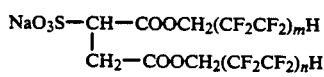

(m and n is 2 or 3)

(6) Preparation of Heat Developable Light-Sensitive Materials (U) and (V)

Samples of heat developable light-sensitive material were prepared as follows.

That is, 12.5 ml of Organic Silver Salt Dispersion-1 prepared above, 10 ml of the aforesaid blue-sensitive silver halide emulsion (using the aforesaid Emulsion Em-1), 2.0 g of gelatin, 39.8 ml of the aforesaid Dye Providing Material Dispersion-1, 12.5 ml of the aforesaid Developing Agent Dispersion U or V, and $5.0 \times 10^{-2}$ mol (per mol of silver halide) of the compound shown below were mixed and, after further adding thereto 2.50 ml of a hardening agent solvent (the solvent obtained by dissolving a reaction product of tetra(vinylsulfonylmethyl)methane and taurine as 1/1 by weight ratio in an aqueous solution of 1 wt % phenylcarbamoylated gelatin such that the content of tetra(vinylsulfonylmethyl)methane became 3% by weight) and 3.80 g of polyethylene glycol 300 (made by Kanto Kagaku K.K.) as heat solvent, the resultant mixture was coated on a polyethylene terephthalate film of 180 μm in thickness having a subbing layer at a silver coverage of 1.76 g/m² and also a protective layer composed of a mixture of the aforesaid phenylcarbamoylated gelatin and poly(N-vinylpyrrolidone) was formed thereon to provide Heat Developable Light-Sensitive Materials (U) and (V).

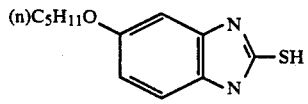

(7) Preparation of Image Receiving Member-1

A baryta-coated paper for photography was coated with a tetrahydrofuran solution of polyvinyl chloride (n=1,100, name by Wako Junyaku K.K.) at a polyvinyl chloride coverage of 12 g/m².

Each of the aforesaid heat developable light-sensitive materials was exposed to blue light through a step wedge, the aforesaid image receiving member was superposed on the light-sensitive material, and after applying thereto a heat development for 1 minute at 150° C. by a heat developing machine (Developer Module 277, trade name, made by Minnesota Mining & Manufacturing Company), the heat developable light-sensitive material was quickly separated from the image receiving member, whereby yellow negative images of the step wedge were obtained on the polyvinyl chloride surface of the image receiving member.

The maximum densities of the yellow transferred images obtained by the heat development are shown in Table 8.

TABLE 8

| Sample | Maximum Density |
|---|---|
| (U) | 2.00 |

TABLE 8-continued

| Sample | Maximum Density |
|---|---|
| (V) | 1.81 |

As is apparent from the results shown in Table 8, it can be seen that Sample (U) using the developing agent precursor of the present invention shows the higher maximum density as compared with Comparative Sample (V).

EXAMPLE 9

A transparent polyester terephthalate film of 180 μm in thickness having a subbing layer was coated with a coating composition for light-sensitive layer having the same composition as that of Sample (U) or (V) in Example 8 except that the following Dye Providing Material Dispersion (b) was used in place of the dye providing material dispersion in Example 8 and also the red-sensitive silver iodobromide emulsion described in Example 8 was used as the silver halide emulsion at a wet thickness of 70 μm and dried to form a first light-sensitive layer.

Dye Providing Material Dispersion (b)

The dye providing material dispersion was prepared by the same manner as in Example 8 except that the following Dye Providing Material (3) (amount: 90 g) was used in place of the dye providing material in Example 8.

Dye Providing Material (3) (cyan dye providing material)

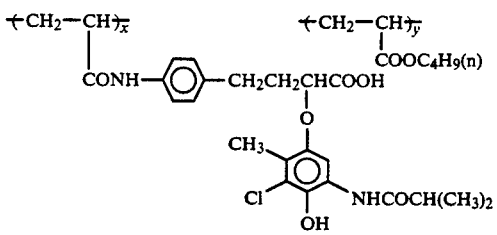

x = 60 wt%, y = 40 wt%

Then, a first interlayer having the following composition was formed on the first light-sensitive layer.

| | |
|---|---|
| Gelatin | 0.6 g/m² |
| Polyvinylpyrrolidone | 0.3 g/m² |
| Compound Shown Below | 0.25 g/m² |
| Methylbenzotriazole Silver | 0.6 g/m² |
| p-Butoxybenzamido-2,4-dichloro-6- | 20 mg/m² |

-continued hydroxy-s-triazine Sodium

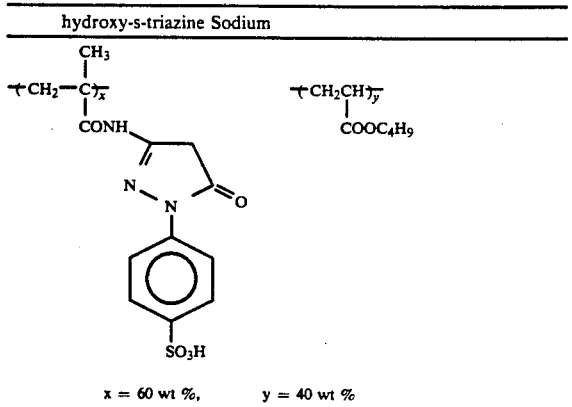

x = 60 wt %,  y = 40 wt %

Then, the same coating composition for the first light-sensitive layer as described above, except that the following dye providing material dispersion was used and also the aforesaid green-sensitive silver halide emulsion was used as the silver halide emulsion, was coated on the first interlayer to form a second light-sensitive layer.

The dye providing material dispersion was the same as the aforesaid Dye Providing Material Dispersion-1 except that 35.5 g of the following Dye Providing Material (2) was used.

Dye Providing Material (2) (magenta dye providing material)

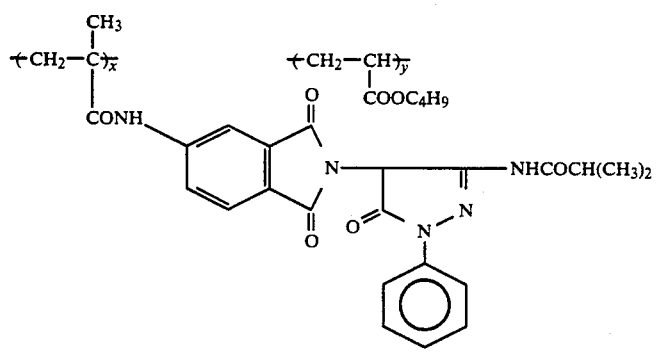

x = 40 wt%,  y = 60 wt%

Then, to the composition for the first interlayer was further added the following yellow filter dye (0.2 g/m²), and the resulting composition was coated on the second light-sensitive layer to form a second interlayer.

Yellow Filter Dye

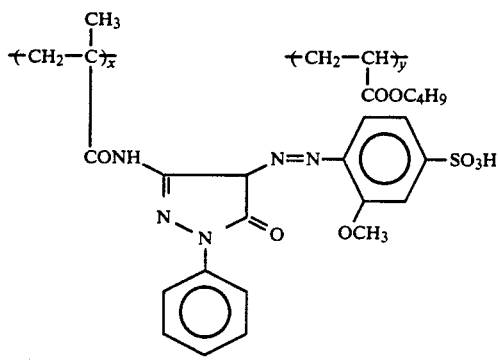

x = 55 wt%,  y = 45 wt%

Furthermore, the same coating composition for the light-sensitive layer as the composition for Sample (U) or (V) in Example 8 was coated on the second interlayer at a wet thickness of 80 μm to form a third light-sensitive layer.

Then, a protective layer having the following composition was formed on the third light-sensitive layer to provide a multilayer light-sensitive material (Sample (W) or (X)).

| | |
|---|---|
| Gelatin | 0.28 g/m² |
| Polyvinylpyrrolidone | 0.14 g/m² |
| SiO₂ | 0.36 g/m² |
| Saflon | 1.0 g/m² |
| p-Butoxybenzamide | 0.42 g/m² |

Each of Heat Developable Light-Sensitive Materials ((W) and (X)) was exposed to red light, green light, and blue light at 800 CMS and subjected to the heat development as in Example 7. The maximum densities of the transferred dyes of cyan, magenta, and yellow thus formed were measured.

The results are shown in Table 9.

TABLE 9

| Sample | Yellow Dmax | Magenta Dmax | Cyan Dmax |
|---|---|---|---|
| (W) | 1.95 | 2.05 | 1.95 |
| (X) | 1.81 | 1.94 | 1.83 |

Sample (W): Sample of the present invention
Sample (X): Comparative sample

As is apparent from the above results, it can be seen that Sample (W) using the color developing agent precursor of the present invention is excellent in the maximum densities as compared with Comparative Sample (X).

While the invention has been described in detail and with reference to specific embodiments thereof, it will be apparent to one skilled in the art that various changes and modifications can be made therein without departing from the spirit and scope thereof.

What is claimed is:

1. A color developing composition comprising a p-phenylenediamine series color developing agent or a precursor thereof represented by formula (I):

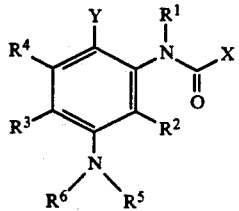 (I)

wherein R¹ represents a hydrogen atom or an alkyl group and x represents —O—R⁷ or

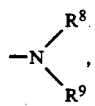

wherein R⁷ represents an alkyl group, an aryl group, or a heterocyclic ring and R⁸ and R⁹, which may be the same or different, each represents a hydrogen atom, an alkyl group, an aryl group, or a heterocyclic ring, R⁸ and R⁹ may combine with each other to form a heterocyclic ring, R², R³ and R⁴, which may be the same or different, each represents a hydrogen atom, an alkyl group, an amino group, a hydtoxy group, an alkoxy group, an acylamino group, a sulfonamide group, an alkoxycarbonylamino group, an aminocarbonylamino group, a sulfonyl group, a carbamoyl group, a sulfamoyl group, a cyano group, a halogen atom, an alkoxycarbonyl group, an acyl group, an acyloxy group, a sulfo group, or a carboxy group; R⁵ and R⁶ each represents an alkyl group, R⁵ and R⁶, R³ and R⁶, and/or R² and R⁵ may combine with each other to form a ring structure, and R² and X may combine with each other to form a heterocyclic ring;

Y represents

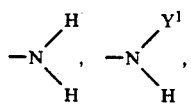

or —N=Y², wherein Y¹ represents —SO₃H, —SO₃Na, —SO₂R¹¹,

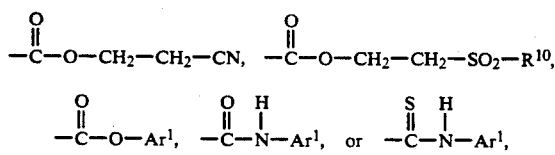

wherein R¹⁰ and R¹¹ each represents an alkyl group or an aryl group which may be substituted, and Ar¹ represents an aryl group which may be substituted and Y² represents

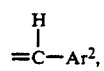

wherein Ar² represents an aryl group which may be substituted.

2. The color developing composition as in claim 1, wherein said color developing agent or a precursor thereof is present in said developing composition in an amount of from $1 \times 10^{-3}$ to $1 \times 10^{-1}$ mol/liter.

3. The color developing composition as in claim 1, wherein said color developing agent or a precursor thereof is present in said color developing composition in an amount of from $1 \times 10^{-3}$ to $1 \times 10^{-1}$ mol/liter, and R¹ represents a hydrogen atom.

4. The color developing composition as in claim 1, wherein said color developing agent or a precursor thereof is present in said color developing composition in an amount of from $1 \times 10^{-3}$ to $1 \times 10^{-1}$ mol/liter, and R², R³ and R⁴ each represents a hydrogen atom or an alkyl group having 1 to 2 carbon atoms.

5. The color developing composition as in claim 1, wherein when X represents

R⁸ and R⁹ each represents an alkyl group having 1 to 4 carbon atoms; and when X represents —O—R⁷, R⁷ represents an alkyl group having 1 to 4 carbon atoms.

6. The color developing composition as in claim 1, wherein R², R³ and R⁴ each represents a hydrogen atom or an alkyl group having 1 to 2 carbon atoms.

7. The color developing composition as in claim 1, wherein R⁵ and R⁶ each represents an alkyl group having 1 to 6 carbon atoms.

8. A color developing composition comprising a p-phenylenediamine series color developing agent or a precursor thereof represented by formula (I):

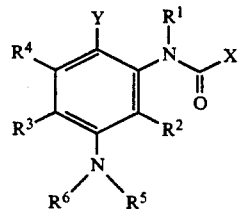 (I)

wherein R¹ represents a hydrogen atom;
X represents —O—R⁷ wherein R⁷ represents an alkyl group, or X represents

wherein R⁸ and R⁹ each represents an alkyl group;
R², R³ and R⁴ each represents a hydrogen atom or an alkyl group;
R⁵ and R⁶ each represents an alkyl group; and
R⁵ and R⁶ may combine with each other to form a ring structure;
Y represents

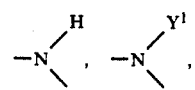

or —N=Y², wherein Y¹ represents —SO₃H, —SO₃Na, —SO₂R¹¹,

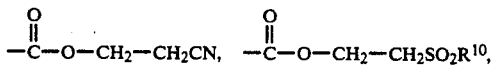

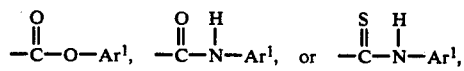

wherein R¹⁰ and R¹¹ each represents an alkyl group or an aryl group which may be substituted, and Ar¹ represents an aryl group which may be substituted and Y² represents

wherein Ar² represents an aryl group which may be substituted.

9. The color developing composition as in claim 8, wherein Y represents —NH₂.

10. The color developing composition as in claim 9, wherein R⁷ represents an alkyl group having 1 to 4 carbon atoms; R⁸ and R⁹ each represents an alkyl group having 1 to 4 carbon atoms; R², R³ and R⁴ each represents a hydrogen atom or an alkyl group having 1 to 2 carbon atoms; and R⁵ and R⁶ each represents an alkyl group having 1 to 6 carbon atoms.

11. The color developing composition as in claim 10, wherein R², R³ and R⁴ each represents a hydrogen atom.

12. The color developing composition as in claim 10, wherein X represents —O—R⁷ wherein R⁷ represents an alkyl group having 1 to 4 carbon atoms.

13. The color developing composition as in claim 10, wherein R², R³ and R⁴ each represents a hydrogen atom; and X represents —O—R⁷ wherein R⁷ represents an alkyl group having 1 to 4 carbon atoms.

14. A compound represented by formula (I):

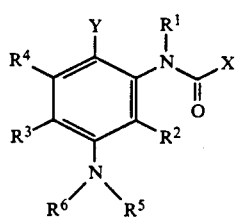

wherein R¹ represents a hydrogen atom;
X represent —O—R⁷ wherein R⁷ represents an alkyl group having 1 to 4 carbon atoms;
R², R³ and R⁴ each represents a hydrogen atom or an alkyl group having 1 to 2 carbon atoms;
R⁵ and R⁶ each represents an alkyl group having 1 to 6 carbon atoms; and
Y represents

15. The compound as in claim 14, wherein R², R³ and R⁴ each represents a hydrogen atom.

16. A color photographic material comprising a color coupler and a p-phenylenediamine series color developing agent or a precursor thereof represented by formula (I):

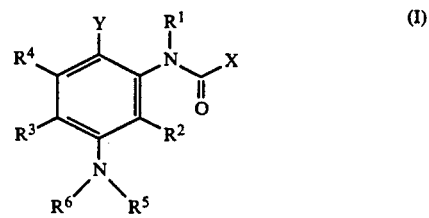

wherein R¹ represents a hydrogen atom and X represents —O—R⁷, wherein R⁷ represents an alkyl group having 1 to 4 carbon atoms,
R², R³ and R⁴, which may be the same or different, each represents a hydrogen atom, or an alkyl group having 1 to 2 carbon atoms,
R⁵ and R⁶ each represents an alkyl group,
R⁵ and R⁶ may combine with each other to form a ring structure; Y represents

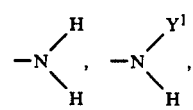

or —N=Y², wherein Y¹ represents —SO₃H, —SO₃Na, —SO₂R¹¹,

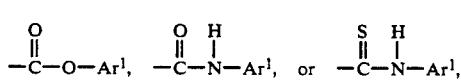

wherein R¹⁰ and R¹¹ each represents an alkyl group or an aryl group which may be substituted, and Ar¹ represents an aryl group which may be substituted and Y² represents

wherein Ar² represents an aryl group which may be substituted.

17. The color photographic material as in claim 16, wherein R², R³ and R⁴ each represents a hydrogen atom; and R⁵ and R⁶ each represents an alkyl group having 1 to 6 carbon atoms.

18. The color photographic material as in claim 16, wherein said color photographic material contains a silver salt oxidizing agent, and wherein the amount of the color developing agent or a precursor thereof is from 0.05 mol to 10 mol per mol of the silver salt oxidizing agent.

* * * * *